(12) United States Patent
Kirshner

(10) Patent No.: US 6,322,504 B1
(45) Date of Patent: Nov. 27, 2001

(54) COMPUTERIZED INTERACTIVE METHOD AND SYSTEM FOR DETERMINING A RISK OF DEVELOPING A DISEASE AND THE CONSEQUENCES OF DEVELOPING THE DISEASE

(75) Inventor: Ronald Kirshner, Rochester, NY (US)

(73) Assignee: R and T, LLC, Rochester, NY (US)

( * ) Notice: Subject to any disclaimer, the term of this patent is extended or adjusted under 35 U.S.C. 154(b) by 0 days.

(21) Appl. No.: 09/535,689

(22) Filed: Mar. 27, 2000

(51) Int. Cl.$^7$ ..................................................... A61B 5/00
(52) U.S. Cl. ............................. 600/300; 705/2; 128/904; 128/920
(58) Field of Search ..................... 600/300–301; 128/903–904, 920–925; 703/2–3; 707/104

(56) References Cited

U.S. PATENT DOCUMENTS

| | | |
|---|---|---|
| 4,733,354 | 3/1988 | Potter et al. . |
| 5,255,187 | 10/1993 | Sorensen . |
| 5,594,637 | 1/1997 | Eisenberg et al. . |
| 5,724,580 | 3/1998 | Levin et al. . |
| 5,746,204 | 5/1998 | Schauss . |
| 5,796,759 | 8/1998 | Eisenberg et al. . |
| 5,800,347 | 9/1998 | Skates et al. . |
| 5,911,132 | 6/1999 | Sloane . |
| 5,935,060 | 8/1999 | Iliff . |
| 5,937,387 * | 8/1999 | Summerell et al. .................. 600/301 |
| 5,974,124 | 10/1999 | Schlueter, Jr. et al. . |
| 5,976,082 | 11/1999 | Wong et al. . |
| 5,993,386 | 11/1999 | Ericsson . |
| 5,997,476 | 12/1999 | Brown . |
| 6,022,315 | 2/2000 | Iliff . |
| 6,024,699 | 2/2000 | Surwit et al. . |
| 6,110,109 * | 8/2000 | Hu et al. ............................... 600/300 |
| 6,139,494 * | 10/2000 | Cairnes ................................. 600/300 |
| 6,206,829 * | 3/2001 | Iliff ....................................... 600/301 |

OTHER PUBLICATIONS

Dayton et al., CS, "Evaluation of an Internet–Based Decision–Support System for Applying the ATS/CDC Guidelines for Tuberculosis Preventive Therapy," Med. Decis. Making, vol. 20, No. 1, Jan.–Mar. 2000.* English Abstract Provided.

Baehring et al, TU, "Using the World Wide Web—A New Approach to Risk Identification of Diabetes Mellitus," Int. J. Med. Inf., vol. 46, No. 1, Aug. 1997.* English Abstract Provided.

Hayes et al., KA, "The Interactive Patient: A Multimedia Interactive Educational Tool on the World Wide Web," MD Comput., vol. 13, No. 4 Jul.–Aug. 1996.* English Abstract Provided.

(List continued on next page.)

Primary Examiner—John P. Lacyk
Assistant Examiner—Michael Astorino
(74) Attorney, Agent, or Firm—Kenyon & Kenyon

(57) ABSTRACT

An interactive computerized method and system for determining the risk of developing a disease, consequences of the disease, providing ways of modifying the risk, and tracking the progress of an individual as his or her risk factors change or remain the same. The method includes:

transmitting questions to the individual pertaining to risk factors for the disease via a processor;

receiving responses to the questions from the individual via the processor;

transmitting contemporaneous feedback to the responses via the processor;

determining the risk of the individual developing the disease or the associated consequences of having the disease using at least one of the responses and practice guidelines for the disease;

transmitting a summary of positive risk factors and risk modification information to the individual via the processor; and tracking changes in the responses and the positive risk factors of the individual over time.

The system includes a processor executing a program that performs the method.

15 Claims, 74 Drawing Sheets

OTHER PUBLICATIONS

Peltz et al., JE, "A Comprehensive and Cost–Effective Preparticipation Exam Implemented On the World Wide Web," Med. Sci. Sports Exerc., vol. 31, No. 12, Dec. 1999.* English Abstract Provided.

Ishida et al., H., "Computer–Assisted Education of Laboratory Medicine Based on Common Disease Database and Electric RCPC System Using Internet Technology,", Rinsho Byori, vol. 46, No.11, Nov. 1998.* English Abstract Provided.

Duvauferrier et al., R., "The Virtual University in Medicine. Context, Concepts, Specifications, Users' Manual," J. Radiol., vol. 79, No. 9, Sep. 1998.* English Abstract Provided.

Tong et al., D.A. "A Client/Server System for Remote Diagnosis of Cardiac Arrhythmias," Proc. Annu Symp. Comput. Appl. Med. Care. 1995.* English Abstract Provided.

Biro et al., G., "Dr. Quiz: A Program of Medical Question-Data Bank with Access to Internet," Orv Hetil, vol. 140, No. 33, Aug. 1999.* English Abstract Provided.

Sato et al., H., "Interactive 3–D Presentation of Medical Images on Network Using VRML," Proceedings of the $20^{th}$ Annual International Conference of the IEEE Engineering in Medicine and Biology Society, 1998.* English Abstract Provided.

Atalay et al., B., "A WWW–Based HIV Patient Care Expert System," Proceedings $12^{th}$ IEEE Symposium On Computer–Based Medical Systems, Jun. 1999.* English Abstract Provided.

Vissers et al., M.C., "Building a Flexible Protocol Information System with 'Ready for Use' Web–Technology," International Journal of medical Informatics, vol. 53, Nos. 2–3, Feb.–Mar. 1999.* English Abstract Provided.

Gibbons et al., Raymond J., "ACC/AHA/ACP–ASIM Guidelines for the Management of Patients with Chronic Stable Angina," Journal of the American College of Cardiology, vol. 33, No. 7, Jun. 1999.

Fuster et al., Valentin, "$27^{th}$ Bethesda Conference: Matching the Intensity of Risk Factor Management with the Hazard for Coronary Disease Events," Journal of the American College of Cardiology, vol. 27, No. 5, Apr. 1996.

Eagle, Kim A. et al., "ACC/AHA Guidelines for Coronary Artery Bypass Graft Surgery," Journal of the American College of Cardiology, vol. 34, No. 4, Oct. 1999.

Ryan et al., Thomas J., "ACC/AHA Guidelines for the Management of Patients with Acute Myocardial Infarction," Journal of the American College of Cardiology, vol. 34, No. 3, Sep. 1999.

Clinical Practice Guideline No. 10, Unstable Angina: Diagnosis and Management, U.S. Department of Health and Human Services Public Health Service.

Grundy et al., Scott M., "Assessment of Cardiovascular Risk by Use of Multiple–Risk–Factor Assessment Equations," Journal of the American Heart Association, vol. 100, No. 13, Sep. 1999.

Martinez, R., et al., "Multimedia Consultation Session Recording And Playback Using Java–based Browser in Global PACs", Proceedings of the SPIE—The International Society for Optical Engineering, vol. 3339, 1998.* English Abstract Provided.

Tong, D.A., et al., "A Client/Server System For Remote Diagnosis of Cardiac Arrhythmias", Proceedings of Nineteenth Annual Symposium on Computer Applications in Medical Care, 1995.* English Abstract Provided.

Costaridou, L., "Distance Learning In Mammographic Digital Image Processing", British Journal of Radiology, vol. 71, No. 842, 1998.* English Abstract Provided.

Immunomedics Launches a New Interactive Web Site for Patients With Colorectal Cancer and Medical Professionals, 1999.* English Abstract Provided.

NexData Solutions, Inc. Develops A Clinical Interactive Internet Site For Medical Information Systems, Inc., 1998.* English Abstract Provided.

Foran, D.J., et al., "A Distributed Health Information Network For Consultative Services In Surgical Pathology", 1995 IEEE Engineering in Medicine and Biology $17^{th}$ Annual Conference and 21 Canadian Medical and Biological Engineering Conference, Part vol. 1, 1997.* English Abstract Provided.

Barker, T.M., and Young, J., "Design of A Web Interface for Anatomical Images", Australasian Physical & Engineering Sciences in Medicine, vol. 20, No. 1, Mar. 1997*English Abstract Provided.

Horino, M., et al., "Development of Remote Medical Imaging System", Shimadzu Review, vol. 53, No. 2, 1996.* English Abstract Provided.

Boone, J.M., Chavez, A.E., "Comparison of X–ray Cross Sections for Diagnostic And Therapeutic Medical Physics", Medical Physics, vol. 23, No. 12, Dec. 1996.* English Abstract Provided.

* cited by examiner

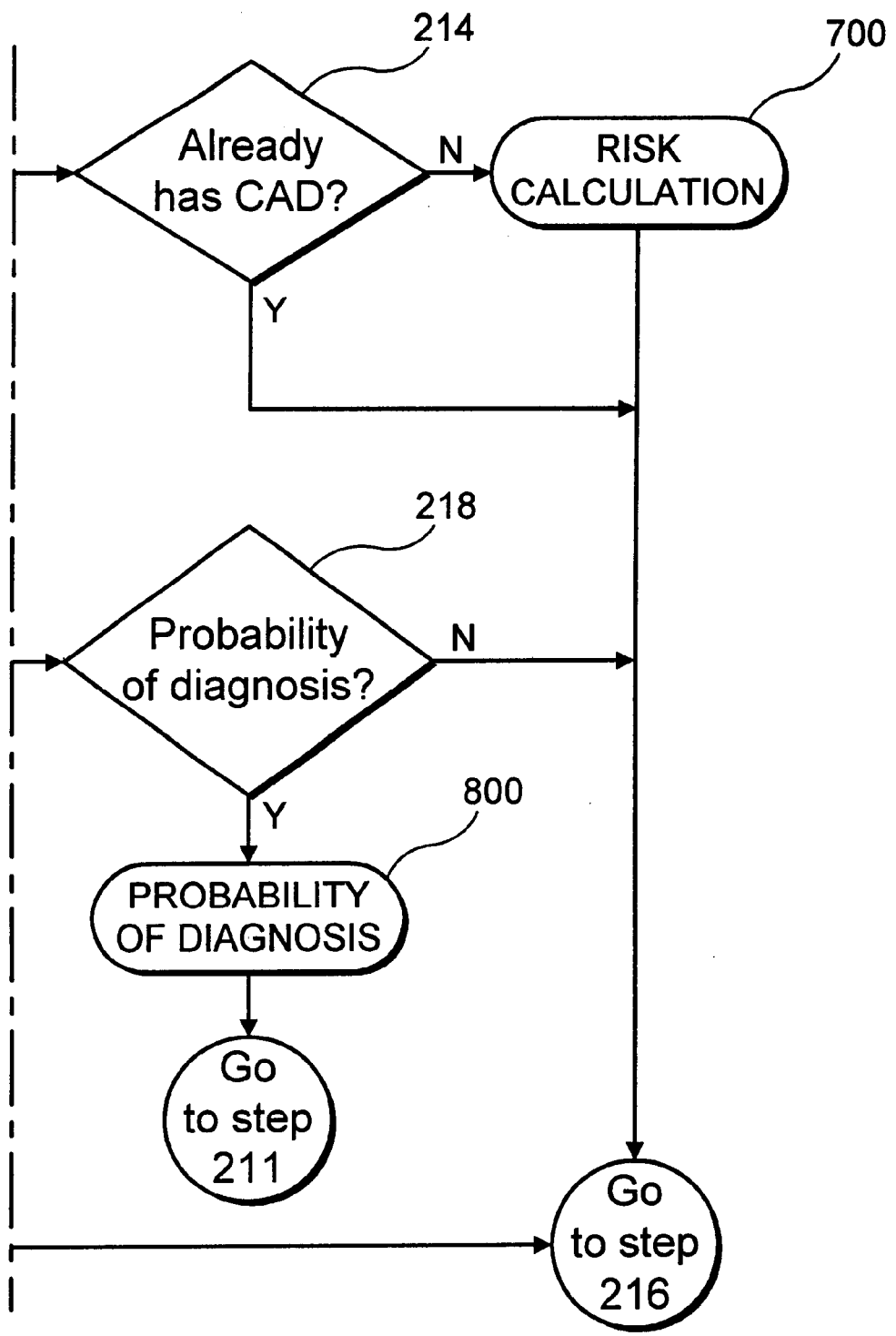
F I G. 2C

Account Registration

Please create User ID for yourself :
*must be 4-16 characters long with no spaces*

303a

Please create a password :
*must be 4-8 characters long with no spaces*

303b

Please confirm your password :

303c

In the event that you forget your password, please enter a question that we can ask to help you remember it (example: enter "What is your mother's maiden name?" In this field if the answer to that question to that question is your password) :

303d

Are you male or female ?

○ MALE   ○ FEMALE

310a

What is your date of birth ?

MONTH  DAY  YEAR 310b  310c  310d

*optional - What is your race?*

310e

*optional - Please tell us your occupation :*

*optional - Please tell us your zip code :*

WWW.CARDIACDOC.COM

HOW TO USE CARDIACDOC

DISCLAIMER/TERMS & CONDITIONS

DICTIONARY OF TERMS

YOUR FEEDBACK/QUESTIONS

 MemberWare
www.memberware.com
Last Previewed : 3/3/2000

FIG. 3B

| Do you ever have chest pain that you think could be related to your heart, or do you have known coronary heart disease ?     No | ⎯ 401, 402 |

| You can probably lower your risk of cardiac problems. Would you like to learn how?<br><br>⦿ Yes    ◯ No   ▷ | ⎯ 205 |

[END THIS SESSION]

F I G. 4A

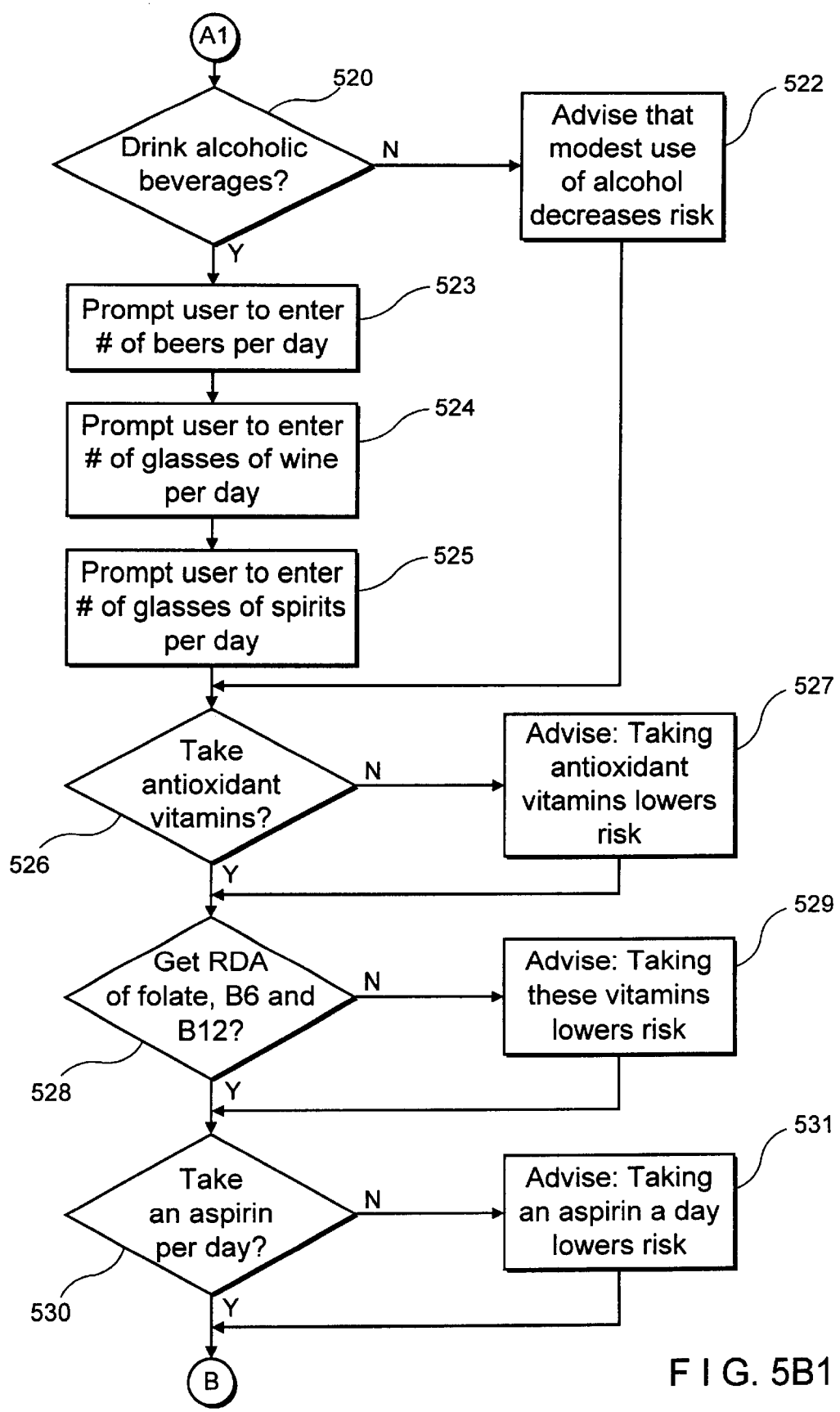
FIG. 5B1

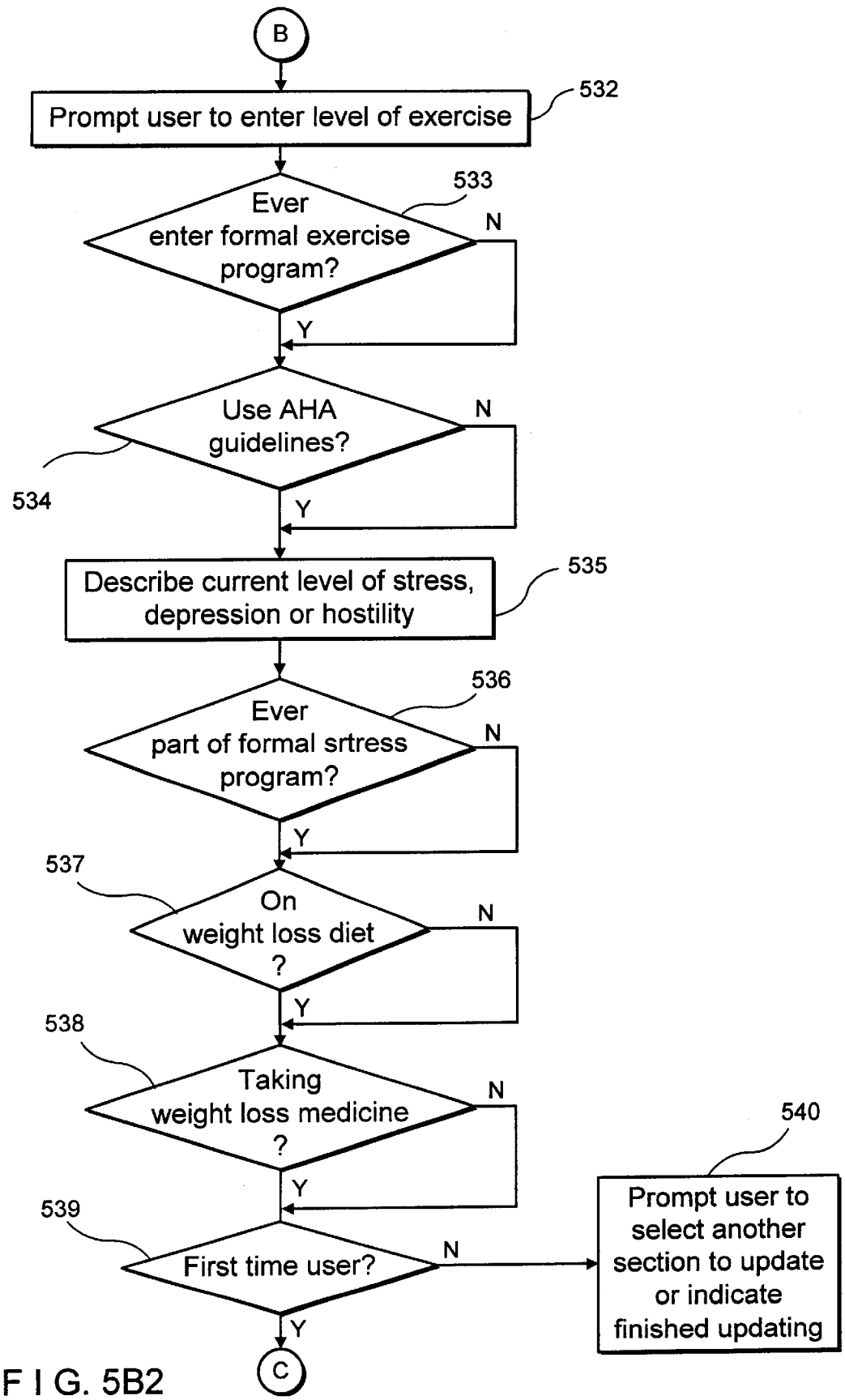
FIG. 5B2

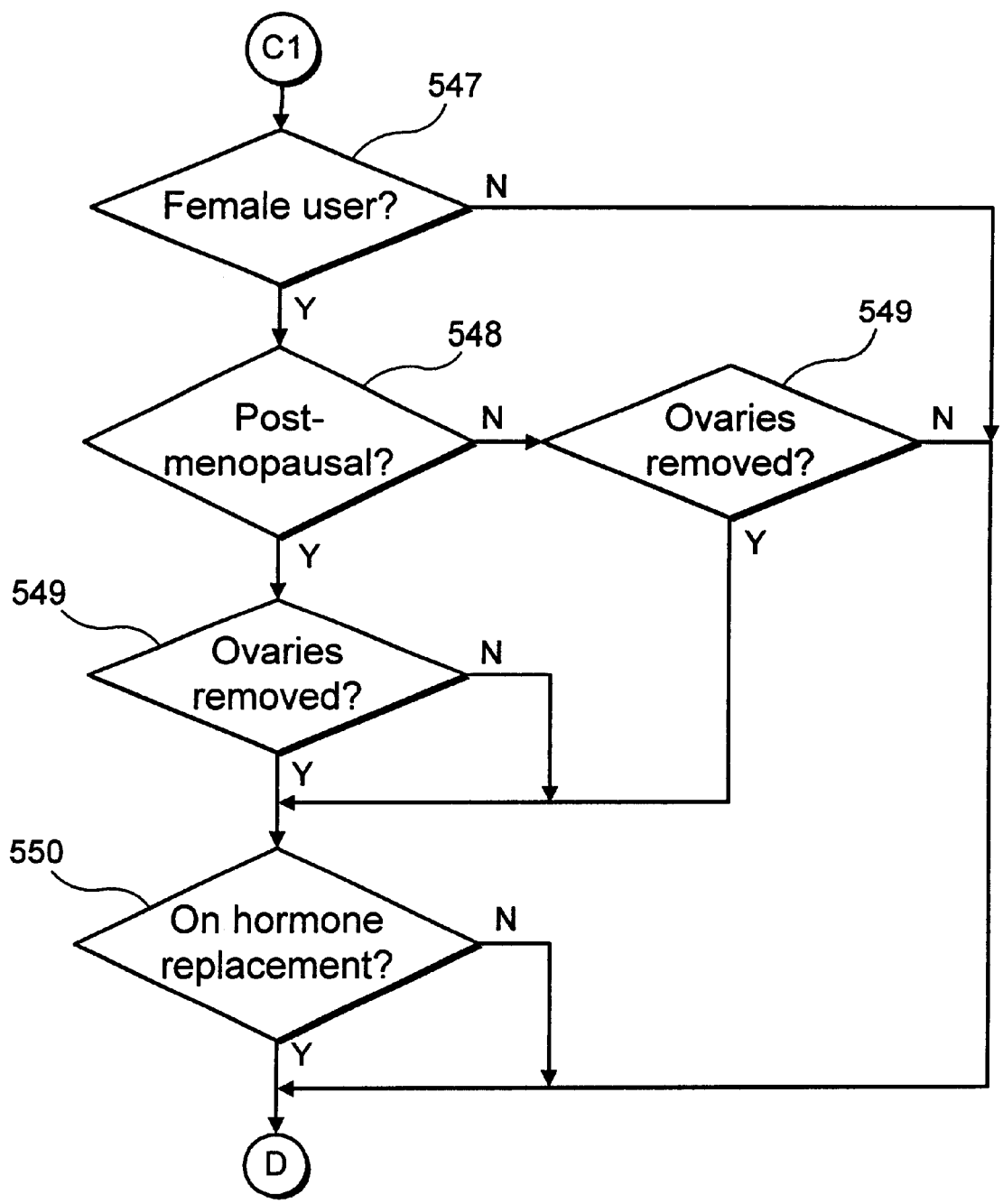
FIG. 5C1

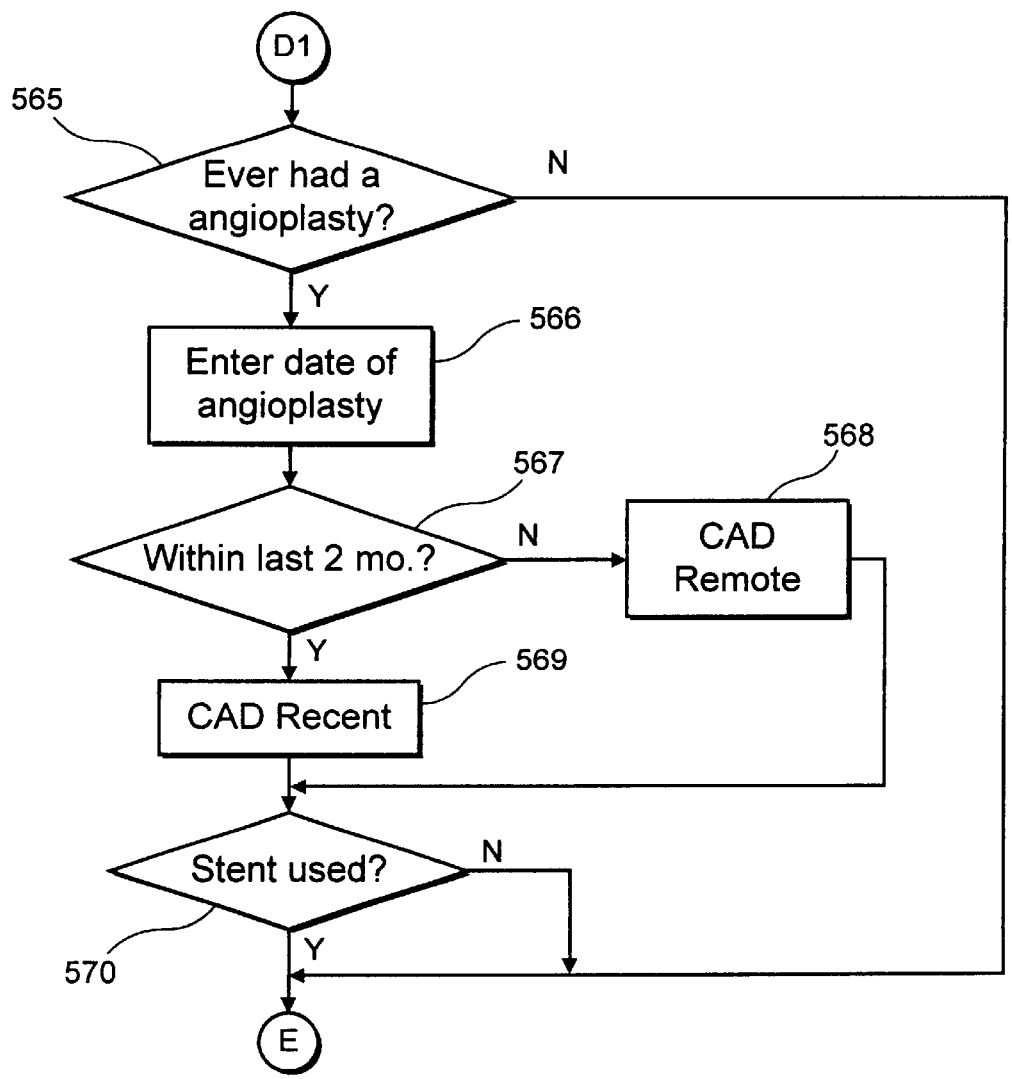
FIG. 5D1

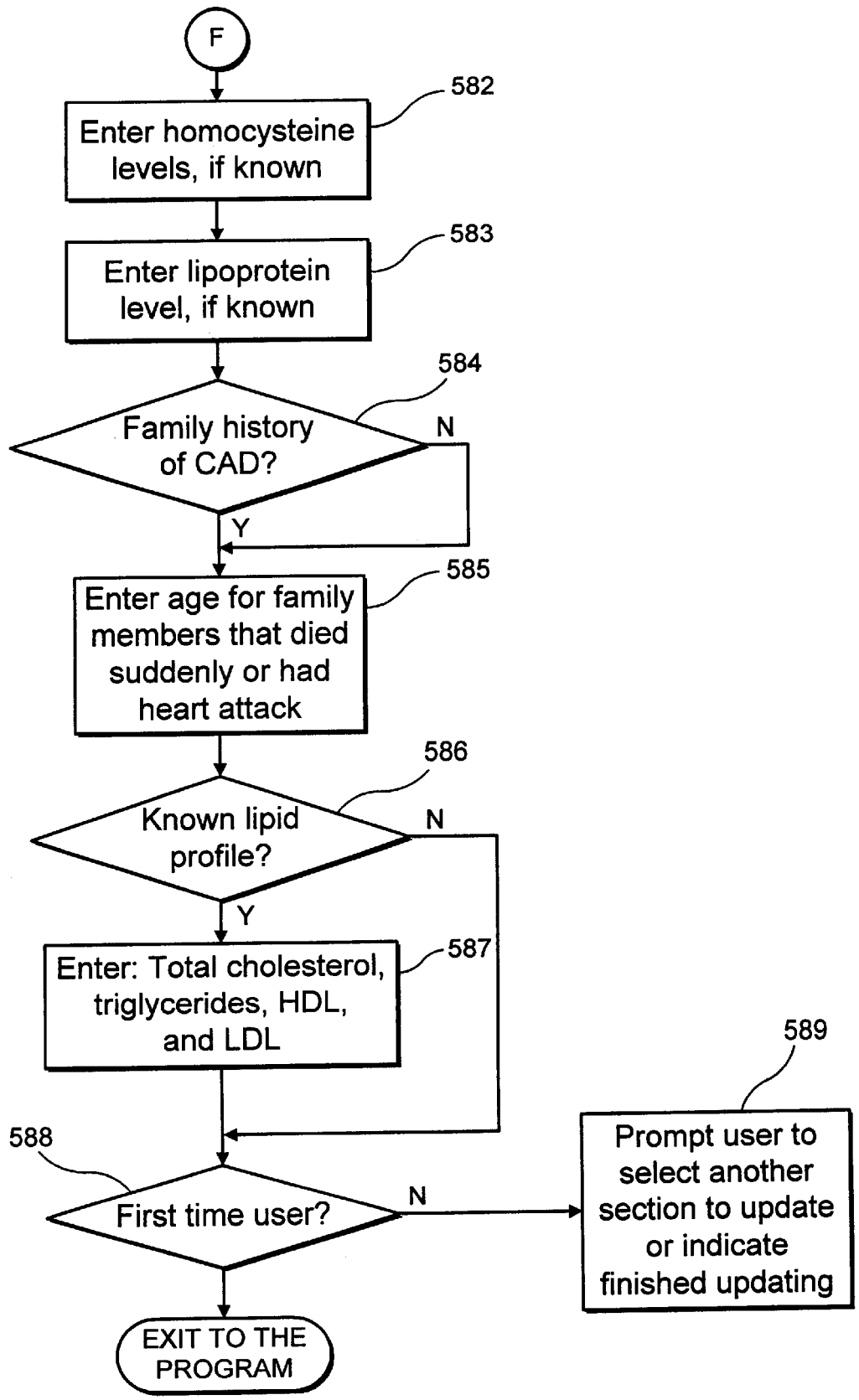
FIG. 5E1

Do you ever have chest pain that you think could be related to your heart, or do you have known coronary heart disease ? No

Risk factor modification section

Your risk for coronary artery disease has to do with your lifestyle, your general health, and your medical history. The next section asks you questions about each of those things. Be sure to answer every question, and be as accurate as you can. The more accurate you are, the more helpful this tool is to you.

Proceed 

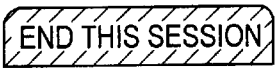
END THIS SESSION

FIG. 5F

Physical Characteristics :

How tall are you ?

| 5 | feet | 09 | inches    OR    [ ] Centimeters |

505a                                              505b

How much do you weigh ?

| 135 | expressed in   ◉ pounds   ○ kilograms

506a

Calculate Body Mass Index   [🖩]  — 508

[END THIS SESSION]

F I G. 5G

| Do you ever have chest pain that you think could be related to your heart, or do you have known coronary heart disease ? | Yes |
|---|---|
| Are you having chest pain right now ? | N |

| How tall are you ? | 69 inches |
|---|---|
| How much do you weigh ? | 160 pounds |
| Your Body Mass Index (BMI) is : | 23.7 |

| Do you currently smoke? | Yes | — 514 |

---

Are you in a smoking cessation class ? — 517
○ Yes   ⦿ No

Are you using smoking cessation medicine ? — 518
○ Yes   ⦿ No

How many years have you smoked ? — 519
[ 4 ]  years

How many packs per day do you smoke ? — 520
[ 1 ]  packs per d  ▷  END THIS SESSION

FIG. 5H

| Your Personal Risk Factor Summary | Now | A Month Ago |
|---|---|---|
| Smoking                       601 | At Risk | At Risk |
| High LDL Cholesterol | Not at Risk | Not at Risk |
| Hypertension | Not at Risk | Not at Risk |
| Enlarged Heart | Not at Risk | Not at Risk |
| No Daily Aspirin              603 | Not at Risk | At Risk |
| Diabetes | Not at Risk | Not at Risk |
| Low LDL Cholesterol | Not at Risk | Not at Risk |
| Obesity | Not at Risk | Not at Risk |
| Lack of Physical Activity | Not at Risk | At Risk |
| Menopause | Not at Risk | Not at Risk |
| Level of Stress | Not at Risk | Not at Risk |
| High Lipids (Triglycerides) | Not at Risk | Not at Risk |
| Excessive Lipoprotein (A) Level | Not at Risk | Not at Risk |
| Excessive Homocysteine Level / Low | Not at Risk | Not at Risk |
| Folate | Not at Risk | At Risk |
| Lack of Anti-oxidant Vitamin | Not at Risk | At Risk |
| Low Alcohol consumption | Not at Risk | Not at Risk |
| Advanced Age | Not at Risk | Not at Risk |
| Family History | Not at Risk | Not at Risk |
| Known Coronary Disease<br>Known Peripheral Vascular Disease | Not at Risk | Not at Risk |

FIG. 6A

Watch out! Cigarette smoking is unhealthy and a risk for getting heart disease. Please ask your doctor about methods for quitting.

516

You should know: Taking anti-oxidan vitamins could lower your nsk of getting coronary artery disease.

527

No exercise: If you start exercising for thirty minutes or more at least three times every week, you will lower your risk of getting Coronary Artery Disease. Ask your doctor about good exercises to try.

532

Watch out! Your high blood pressure puts you at risk for developing Coronary Artery Disease. Ask your doctor for help in reducing your blood pressure.

542

Studies show that even a modest daily consumption of alcoholic beverages will help prevent Coronary Artery Disease.

522

Did you know: Doctors agree that taking daily aspirin could significantly reduce your chances of heart trouble.

530

Watch out! Feeling even a moderat amount of stress adds to your risk of Coronary Artery Disease. Ask your doctor for ideas about reducing stress.

535

Homocysteine and heart disease:
Homocysteine is an amino acid in your blood. People who have higher than normal levels of homocysteine in their blood are at a higher risk for heart disease. Even if you do not have a higher than normal level of homocysteine, it is a good idea to get the RDA of folate - because folate (in vitamins B6, B12, and folic acid) can help keep homocystaine at a healthy level. If you aren't sure what your level of homocystaine is, you need to ask your doctor. Please also talk to your doctor about getting enough folic acid.

| SMOKING CESSATION |
|---|
| CIGARETTE SMOKING MAY BE THE MOST IMPORTANT, PREVENTABLE CAUSE OF ILLNESS AND DEATH IN THE UNITED STATES. THE DEPARTMENT OF HEALTH AND HUMAN SERVICES AGENCY FOR HEALTHCARE POLICY AND RESEARCH (AHCPR) AND THE NATIONAL INSTITUTE OF HEALTHCARE (NIH) BOTH HAVE WEBSITES WITH VALUABLE INFORMATION CONCERNING SMOKING CESSATION.<br><br>ALL VALID GUIDELINES STRESS THAT FIRST AND FOREMOST SMOKING CESSATION NEEDS TO BE IDENTIFIED BY THE SMOKER AS A CRITICAL GOAL. SMOKERS NEED TO HAVE SUPPORT FROM FAMILY, FRIENDS AND CO-WORKERS. THESE INDIVIDUALS NEED TO BE COMMITTED TO SMOKING CESSATION. THE GOAL NEEDS TO BE COMPLETE CESSATION OF ALL TOBACCO USE. STUDIES HAVE SHOWN THAT THE GREATEST CHANCE OF SUCCESS OCCURS WHEN STRUCTURED PROGRAMS ARE USED. THERE ARE MANY ORGANIZATIONS THAT HAVE WEBSITES THAT MAY BE HELPFUL E.G. AMERICAN HEART ASSOCIATION AND NIH. |

FIG. 6C

| DYSLIPIDEMIA |
|---|
| DYSLIPIDEMIA MEANS AN ABNORMALITY OF ONE'S LIPID LEVELS. LIPID LEVELS ARE USUALLY BROKEN DOWN INTO FOUR COMPONENTS:<br>    1. TOTAL CHOLESTEROL<br>    2. LDL (LOW DENSITY LIPOPROTEIN)<br>    3. HDL (HIGH DENSITY LIPOPROTEIN)<br>    4. TRIGLYCERIDES<br>TARGET LEVELS FOR TOTAL CHOLESTEROL AND LDL ARE BASED ON ONE'S RISK FACTOR HISTORY. INDIVIDUALS WHO HAVE KNOWN CORONARY ARTERY DISEASE SUCH AS THOSE WHO HAVE HAD A HEART ATTACK, HEART SURGERY OR ANGIOPLASTY ARE URGED TO KEEP THEIR TOTAL CHOLESTEROL BELOW 180 AND THEIR LDL BELOW 100. CLINICAL TRIALS HAVE PROVEN THAT KEEPING ONE'S LEVELS AS LOW AS POSSIBLE, CERTAINLY AT THE LEVELS SUGGESTED WILL REDUCE THE RISK OF FUTURE EVENTS SUCH AS MYOCARDIAL INFARCTION AND DEATH. IN PEOPLE WHO HAVE KNOWN CORONARY ARTERY DISEASE, IF ONE'S BASELINE LDL LEVEL IS LESS THAN 130, IT IS POSSIBLE THAT WITH DIET, EXERCISE, AND WEIGHT CONTROL ONE COULD BRING ONE'S LDL LEVEL DOWN TO THE TARGET RANGE. IF, HOWEVER BASELINE LDL IS ABOVE 130 IT IS UNLIKELY THAT DIET ALONE WILL WORK. AT THIS POINT, MEDICATION IS USUALLY ADDED. YOU WILL NEED TO DISCUSS THIS WITH YOUR PHYSICIAN. INDIVIDUALS WHO DO NOT HAVE KNOWN CORONARY DISEASE OR DIABETES SHOULD CONSIDER CHOLESTEROL LEVELS BETWEEN 200 AND 240 AND LDL LEVELS BETWEEN 130 AND 160 TO BE BORDERLINE HIGH AND CERTAINLY ANY NUMBERS ABOVE THIS SHOULD BE TREATED UNDER THE CARE OF A HEALTHCARE PROFESSIONAL. INDIVIDUALS WHO HAVE A COMBINATION OF RISK FACTORS INCLUDING: ADVANCED AGE, HYPERTENSION, SMOKING OR POSITIVE FAMILY HISTORY SHOULD CONSIDER AS UPPER ACCEPTABLE LEVELS OF TOTAL CHOLESTEROL OF 200 AND LDL LEVELS OF 130 mg ldl. IN GENERAL, THE LOWER TOTAL CHOLESTEROL LEVEL AND THE LOWER LDL LEVEL, THE LOWER THE RISK OF FUTURE EVENTS SUCH AS HEART ATTACK OR STROKE. THIS IS TRUE EITHER IN THE PRIMARY PREVENTION MODE OR SECONDARY PREVENTION RISK ONCE CORONARY ARTERY DISEASE IS ALREADY KNOWN TO EXIST. HDL IS ANOTHER TYPE OF CHOLESTEROL. ANY LEVEL ABOVE 35 mg ldl IS CONSIDERED ABNORMAL AND SHOULD BE TREATED UNDER THE CARE OF A HEALTHCARE PROFESSIONAL. TRIGLYCERIDES IS ANOTHER FORM OF LIPIDS. LEVELS BETWEEN 200 mg PER DECILITER ARE CONSIDERED BORDERLINE HIGH, 400 - 1000 mg PER DECILITER ARE CONSIDERED HIGH AND OVER 1000 ARE CONSIDERED DANGEROUSLY HIGH. TREATMENT TO BRING LIPID LEVELS UNDER CONTROL USUALLY ENTAILS A COMBINATION OF DIET, EXERCISE, AND MEDICATION. DIET USUALLY INVOLVES SOME SORT OF A STEP 2 AHA DIET. THIS INVOLVES REDUCTION OF SATURATED FAT. MEDICATIONS CAN ALSO BE TAKEN TO DECREASE LIPID LEVELS. MEDICATIONS THEY USE TODAY MOSTLY INCLUDE THE STATINS. YOU WILL NEED TO DISCUSS THIS WITH YOUR PHYSICIAN. |

FIG. 6D(1)

TWO ADDITIONAL NOTES:
1. THE SOY BEAN INDUSTRY RECENTLY RECEIVED GOOD NEWS FROM THE FOOD AND DRUG ADMINISTRATION. EFFECTIVE OCTOBER 26, 1999 THE FDA WILL ALLOW FOODS CONTAINING SOY TO CLAIM THAT THEY ARE HEART HEALTHY.
THE SCIENCE BEHIND THIS IS THAT IT HAS BEEN CONCLUDED THAT A DIET CONTAINING 25 GRAMS OF SOY PROTEIN PER DAY IN ASSOCIATION WITH AN OTHERWISE LOW FAT DIET MAY REDUCE LDL CHOLESTEROL. LDL CHOLESTEROL IS THAT PORTION OF CHOLESTEROL THAT IS KNOWN TO BE SIGNIFICANT IN CAUSING CARDIOVASCULAR DISEASE.
IT IS REPORTED THAT A PRODUCT MUST CONTAIN AT LEAST 6.25 GRAMS OF SOY PROTEIN PER SERVING IN ORDER TO CARRY THE HEART HEALTHY LABEL. IT APPEARS THAT THERE WILL NOW BE A FRENZY OF FOOD PRODUCERS USING SOY AND TOUTING THEIR PRODUCT AS HEART HEALTHY. LIKEWISE, HEALTH CONSCIENTIOUS CONSUMERS ARE EXPECTED TO GRAVITATE TOWARDS THESE PRODUCTS. THE SOYBEAN INDUSTRY HAS ALSO PETITIONED THE FDA TO ACCEPT THE ARGUMENT THAT SOYBEAN PLANT CHEMICALS CALLED ISOFLAVONES LIKEWISE DECREASE THE RISK OF HEART DISEASE.
IT IS EXPECTED THAT THE FDA WILL DECIDE ON THIS ARGUMENT IN THE NEAR FUTURE.
IT SHOULD BE POINTED OUT THAT THE CHEMICALS CALLED ISOFLAVONES
ARE ALSO PRESENT IN LARGE CONCENTRATIONS IN GRAPE SEED EXTRACT.
2. RECENT RESEARCH HAS FOUND THAT PEOPLE WITH MILD TO MODERATE ELEVATED CHOLESTEROL CAN REDUCE THESE LEVELS BY CONSUMING SOLUBLE FIBER AND ADHERING TO THE AMERICAN HEART ASSOCIATION STEP 1 DIET. CHOLESTEROL LEVELS MAY FALL AS MUCH AS 10%. THE MOST COMMON FORM OF SOLUBLE FIBER STUDIED IS PSYLLIUM. THIS IS A NATURALLY OCCURRING SUBSTANCE DERIVED FROM THE PSYLLIUM SEED.

FIG. 6D(2)

| HYPERTENSION (HIGH BLOOD PRESSURE) |
|---|
| HYPERTENSION IS A MAJOR RISK FACTOR FOR CORONARY ARTERY DISEASE. HIGH BLOOD PRESSURE PROMOTES THE ATHEROSCLEROTIC PROCESS RESPONSIBLE FOR PLAQUES IN CORONARY ARTERIES.<br><br>RECENTLY THE WORLD HEALTH ORGANIZATION (WHO) AND THE INTERNATIONAL SOCIETY OF HYPERTENSION (ISH) PUBLISHED GUIDELINES FOR THE MANAGEMENT OF HYPERTENSION. THESE ORGANIZATIONS DEFINE HYPERTENSION AS A SYSTOLIC BLOOD PRESSURE OF 140 mm hg OR GREATER AND/OR DIASTOLIC BLOOD PRESSURE OF 90 mm hg OR GREATER. THESE VALUES ARE FOR PEOPLE WHO ARE NOT TAKING ANTI-HYPERTENSIVE MEDICATIONS.<br><br>CO-EXISTING RISK FACTORS MUST ALSO BE TAKEN INTO ACCOUNT WHEN DETERMINING THE SEVERITY OF HYPERTENSION. INDIVIDUALS WHO HAVE CO-EXISTING RISK FACTORS SUCH AS DIABETES, HEART FAILURE OR RENAL FAILURE SHOULD HAVE TREATMENT AIMED AT BRINGING THE SYSTOLIC BLOOD PRESSURE TO LESS THAN 130 mm hg AND DIASTOLIC PRESSURE TO LESS THAN 85 mm hg.<br><br>IT SHOULD ALSO BE NOTED THAT THERE IS NOT A "THRESHOLD" EFFECT IN THE INTERACTION OF BLOOD PRESSURE AS IT RELATES TO THE DEVELOPMENT OF CORONARY ARTERY DISEASE. THAT IS TO SAY WHILE 140/90 IS A NUMBER TO CONSIDER FOR CLASSIFYING ONE AS HYPERTENSIVE, SYSTOLIC OF 130 TO 140 AND DIASTOLIC PRESSURES OF 80 TO 90 ARE ALSO CONSIDERED BORDERLINE HIGH AND SHOULD BE TAKEN SERIOUSLY. IN THIS SAME LIGHT, AS BLOOD PRESSURE INCREASES TO HIGHER LEVELS, ABOVE 140/90, THE RISK FOR ATHEROSCLEROSIS AND END ORGAN DETRIMENTAL EFFECTS INCREASES. AGAIN, THIS BECOMES MARKEDLY SO WHEN ADDITIONAL FACTORS ARE PRESENT.<br><br>THERE ARE MANY DIFFERENT DRUGS AVAILABLE TO TREAT HYPERTENSION. THE DIAGNOSIS AND TREATMENT OF HYPERTENSION IS A COMPLEX AREA AND ABSOLUTELY NEEDS TO BE UNDER THE GUIDANCE OF A HEALTHCARE PROFESSIONAL. |

FIG. 6E

| LEFT VENTRICULAR HYPERTROPHY |
|---|
| LEFT VENTRICULAR HYPERTROPHY IS ENLARGEMENT OF THE HEART, USUALLY A CONSEQUENCE OF HYPERTENSION (HIGH BLOOD PRESSURE). THIS IS ASSOCIATED WITH INCREASED RISK OF ADVERSE CARDIOVASCULAR EVENTS SUCH AS HEART ATTACK, SUDDEN DEATH AND HEART FAILURE. |

FIG. 6F

| ANTI-PLATELET/ANTI-THROMBOTIC AGENTS (ASPIRIN) |
|---|
| ASPIRIN WORKS BY INHIBITING PLATELETS. THIS RESULTS IN AN ANTI-THROMBOTIC (ANTI-CLOTTING) EFFECT. OTHER AGENTS HAVE BEEN USED BUT THEY EITHER DO NOT HAVE THE DESIRED EFFECT OR HAVE INCREASED COMPLICATIONS.<br><br>INDIVIDUALS WHO HAVE CHRONIC STABLE ANGINA EXPERIENCE SIGNIFICANT DECREASE IN ADVERSE CARDIOVASCULAR EVENTS IF THEY USE ASPIRIN.<br><br>IF AN INDIVIDUAL IS SUFFERING FROM UNSTABLE ANGINA, ASPIRIN SIGNIFICANTLY DECREASES THE RISK OF HEART ATTACK AND DEATH.<br><br>THIS IS CALLED SECONDARY PREVENTION. IN PATIENTS WITH KNOWN CORONARY ARTERY DISEASE, ASPIRIN IS RECOMMENDED IN A DOSE OF 75 TO 325 mg DAILY. THERE ARE RISKS AND CONTRAINDICATIONS TO THIS TREATMENT, THEREFORE THIS SHOULD BE DISCUSSED WITH YOUR HEALTHCARE PROFESSIONAL.<br><br>THE ISSUE CONCERNING USING ASPIRIN IN INDIVIDUALS WITHOUT KNOWN CORONARY ARTERY DISEASE OR WITH NO ANGINA (PRIMARY PREVENTION) IS STILL AN OPEN QUESTION. MEN OVER THE AGE 50 WITH OTHER RISK FACTORS FOR THE DEVELOPMENT OF CORONARY DISEASE APPEAR TO HAVE THE GREATEST BENEFIT. THE GREATER THE RISK FACTOR ANALYSIS THE MORE LIKELY ASPIRIN WOULD BE TO THEIR ADVANTAGE.<br><br>BLEEDING IS A RISK WHEN ONE TAKES ASPIRIN. THIS IS PARTICULARLY SO WITH HYPERTENSION (HIGH BLOOD PRESSURE). THEREFORE, ASPIRIN USE AS PRIMARY PREVENTION SHOULD ONLY BE UNDER THE GUIDANCE OF A HEALTHCARE PROFESSIONAL. |

FIG. 6G

| DIABETES |
|---|
| THERE IS STRONG OBSERVATIONAL DATA THAT THE DIABETES MELLITUS, BOTH TYPE I (INSULIN DEPENDENT) AND TYPE II (NON-INSULIN DEPENDENT) ARE STRONG RISK FACTORS FOR THE DEVELOPMENT OF CORONARY ARTERY DISEASE. THERE IS NOT YET CONVINCING DATA THAT BETTER GLUCOSE CONTROL WILL REDUCE THE INCIDENCE OF CORONARY DISEASE OR ALTER ITS MANIFESTATIONS OF ANGINA, HEART ATTACK OR DEATH. IT IS STILL HIGHLY RECOMMENDED BY THE AMERICAN HEART ASSOCIATION THAT GLUCOSE IN DIABETICS BE HELD UNDER TIGHT CONTROL. |

FIG. 6H

| OBESITY |
|---|
| THE OCTOBER 27, 1999 ISSUE OF THE JOURNAL OF AMERICAN HEART ASSOCIATION CLEARLY SHOWS THAT INCREASING BMI (BODY MASS INDEX, A MEASURE OF OBESITY) IS RELATED TO INCREASED RISK OF CORONARY ARTERY DISEASE AND INCREASED RISK OF DEATH.<br><br>OBESITY HAS A STRONG INTERACTION WITH OTHER MAJOR RISK FACTORS FOR CORONARY ARTERY DISEASE SUCH AS HYPERTENSION, GLUCOSE INTOLERANCE (DIABETES MELLITUS), LOW HDL AND ELEVATED TRIGLYCERIDES. IT IS PRIMARILY THROUGH THESE ASSOCIATIONS THAT OBESITY MEDIATES SUCH A DETRIMENTAL EFFECT. VISCERAL OR CENTRAL ABDOMINAL OBESITY MARKEDLY INCREASES THIS RISK. THIS IS MEASURED BY THE WAIST CIRCUMFERENCE OR WAIST TO HIP RATIO.<br><br>STUDIES HAVE SHOWN A MARKED INCREASE IN THE NUMBER OF OBESE INDIVIDUALS IN OUR SOCIETY. IN FACT, OBESITY IS NOW CONSIDERED A MAJOR PUBLIC HEALTH PROBLEM IN ALL REGIONS OF THE UNITED STATES.<br><br>WEIGHT REDUCTION TO IDEAL BODY WEIGHT IS RECOMMENDED AND THIS SHOULD BE DONE UNDER THE DIRECTION OF YOUR HEALTHCARE PROFESSIONAL. |

FIG. 6I

CARDIOVASCULAR HEALTH AND PHYSICAL ACTIVITY

THE NATIONAL INSTITUTE OF HEALTH ISSUED A CONSENSUS STATEMENT CONCERNING PHYSICAL ACTIVITY AS IT RELATES TO CARDIOVASCULAR HEALTH. THEY SET AS A GOAL TO ACCUMULATE AT LEAST 30 MINUTES OF MODERATELY INTENSE PHYSICAL ACTIVITY ON MOST, IF NOT ALL DAYS OF THE WEEK.

WHAT EXACTLY DOES THIS MEAN? FIRST OF ALL, ONE NEEDS TO DEFINE PHYSICAL ACTIVITY AS IT RELATES TO THE CONCEPT OF EXERCISE. PHYSICAL ACTIVITY IS DEFINED AS "BODILY MOVEMENT PRODUCED BY SKELETAL MUSCLE THAT REQUIRES ENERGY EXPENDITURE". EXERCISE ON THE OTHER HAND IS "A PLANNED, STRUCTURED AND REPETITIVE BODILY MOVEMENT DONE TO IMPROVE OR MAINTAIN ONE OR MORE COMPONENTS OF PHYSICAL FITNESS". THESE DEFINITIONS ARE BASED ON NIH GUIDELINES.

THEREFORE, TO SATISFY THE NIH GUIDELINES, AMERICANS NEED TO INCREASE THEIR LEVELS OF PHYSICAL ACTIVITY TO 30 MINUTES A DAY. THIS COULD TAKE MANY FORMS SUCH AS BRISK WALKING, CYCLING, YARD WORK OR HOME REPAIR, ALL COULD BE CLASSIFIED AS PHYSICAL ACTIVITY. TO MEET NIH GUIDELINES THIS ACTIVITY SHOULD BE DONE WITH MODERATE EXERTION. CLIMBING STAIRS RATHER THAN TAKING THE ELEVATOR, WALKING BRISKLY FROM A PARKED CAR IN A PARKING LOT VS. USING VALET PARKING AND CARRYING ITEMS RATHER THAN USING A CART, ALL WOULD ALSO QUALIFY.

EXERCISE USUALLY INVOLVES A MORE STRUCTURED PROGRAM OF PHYSICAL ACTIVITY. THESE PROGRAMS LIKEWISE WOULD QUALIFY ACCORDING TO NIH GUIDELINES, IF DONE FOR 30 MINUTES AT MODERATE INTENSITY.

WHAT SPECIFICALLY ARE THE ADVANTAGES OF PHYSICAL ACTIVITY AS THEY RELATE TO CARDIOVASCULAR HEALTH?
1. PEOPLE THAT ARE MORE PHYSICALLY ACTIVE HAVE BETTER INDICES OF OBESITY.
2. HDL CHOLESTEROL LEVELS APPEAR TO BE HIGHER IN PEOPLE WHO ARE PHYSICALLY ACTIVE.
3. DIABETES CONTROL USUALLY IS BETTER IN MORE PHYSICALLY ACTIVE PEOPLE. HIGH BLOOD PRESSURE IS ALSO EASIER TO CONTROL IN THE ACTIVE PERSON.

WHAT ARE THE ANTICIPATED BENEFITS OF PHYSICAL ACTIVITY IN PEOPLE WITH CARDIOVASCULAR DISEASE?

STUDIES SHOW THAT PEOPLE WITH KNOWN CORONARY ARTERY DISEASE TEND TO SHOW A REDUCTION IN HEART ATTACK RATES, REDUCTION IN DEATH RATES AND INCREASE IN EXERCISE CAPACITY. THESE BENEFITS MAY ALSO HOLD TRUE FOR PEOPLE THAT DO NOT HAVE KNOWN CORONARY ARTERY DISEASE.

FIG.6J(1)

OTHER POINTS THAT NEED TO BE CONSIDERED:
1. A STRUCTURED EXERCISE PROGRAM IS NOT NECESSARILY REQUIRED TO GAIN THE BENEFIT OF PHYSICAL ACTIVITY, HOWEVER REGULAR SUSTAINED ACTIVITY OF MODERATE INTENSITY IS REQUIRED.
2. THIS PHYSICAL ACTIVITY MUST BE DONE ON A REGULAR, FREQUENT BASIS IN ORDER TO MAINTAIN THE BENEFITS.
3. PEOPLE WITH CARDIOVASCULAR DISEASE SHOULD ABSOLUTELY BE UNDER THE CARE OF A PHYSICIAN BEFORE THEY START A PROGRAM OF INCREASED PHYSICAL ACTIVITY. THERE ARE MANY PROGRAMS IN MOST COMMUNITIES TO ACCOMPLISH THIS. PEOPLE IN THIS CATEGORY SHOULD BE URGED TO TALK TO THEIR PHYSICIANS. BELOW ARE A NUMBER OF ACTIVITIES AND AN INDEX OF THEIR CALORIC EXPENDITURE FOR AN AVERAGE 150 lb PERSON ACCORDING TO THE AMERICAN HEART ASSOCIATION.

FIG. 6J(2)

| CARDIOVASCULAR HEALTH AND PHYSICAL ACTIVITY |
|---|

OTHER POINTS THAT NEED TO BE CONSIDERED:
1. A STRUCTURED EXERCISE PROGRAM IS NOT NECESSARILY REQUIRED TO GAIN THE BENEFIT OF PHYSICAL ACTIVITY, HOWEVER REGULAR SUSTAINED ACTIVITY OF MODERATE INTENSITY IS REQUIRED.
2. THIS PHYSICAL ACTIVITY MUST BE DONE ON A REGULAR, FREQUENT BASIS IN ORDER TO MAINTAIN THE BENEFITS.
3. PEOPLE WITH CARDIOVASCULAR DISEASE SHOULD ABSOLUTELY BE UNDER THE CARE OF A PHYSICIAN BEFORE THEY START A PROGRAM OF INCREASED PHYSICAL ACTIVITY. THERE ARE MANY PROGRAMS IN MOST COMMUNITIES TO ACCOMPLISH THIS. PEOPLE IN THIS CATEGORY SHOULD BE URGED TO TALK TO TEIR PHYSICIANS. BELOW ARE A NUMBER OF ACTIVITIES AND AN INDEX OF THEIR CALORIC EXPENDITURE FOR AN AVERAGE 150 lb PERSON ACCORDING TO THE AMERICAN HEART ASSOCIATION.

| ACTIVITY | | CALORIES |
|---|---|---|
| WALKING | 3 mph | 320 |
| SWIMMING | 50 yds/min | 500 |
| RUNNING | 7 mph | 920 |
| JUMP ROPE | | 750 |
| BICYCLING | 12 mph | 410 |

FIG. 6K

HORMONE REPLACEMENT THERAPY (HRT) IN POST-MENOPAUSAL WOMEN

THE AMERICAN HEART ASSOCIATION'S PUBLICATION (2000 HEART AND STROKE STATISTICAL UPDATE) SHOWS THAT WOMEN HAVE SIGNIFICANT RISK FOR CORONARY ARTERY DISEASE AND ITS CONSEQUENCES. APPROXIMATELY 230,000 WOMEN DIE EACH YEAR FROM CORONARY ARTERY DISEASE. THIS IS THE #1 CAUSE OF DEATH IN AMERICAN WOMEN. CLEARLY, CORONARY ARTERY DISEASE IS A MAJOR HEALTH RISK FOR WOMEN. HOWEVER, IN GENERAL THE ONSET OF CORONARY DISEASE IN WOMEN APPEARS TO BE 10 - 15 YEARS LATER THAN IN MEN. ALTHOUGH NOT COMPLETELY UNDERSTOOD, THIS IS PRESUMABLY DUE TO THE PROTECTIVE EFFECT OF THE SEX HORMONE ESTROGEN PRESENT IN PRE-MENOPAUSAL WOMEN. THUS, WOMEN WHO ARE POST-MENOPAUSAL OR LACK ESTROGEN DUE TO OVARY REMOVAL DEVELOP THE SAME RISK AS MEN AS IT RELATES TO THE DEVELOPMENT OF CORONARY ARTERY DISEASE. THIS HAS PROMPTED THE USE OF HRT TO COMBAT THIS RISK.

RECENT DISCUSSION IN THE JANUARY 26TH ISSUE OF THE JOURNAL OF AMERICAN MEDICAL ASSOCIATION RAISES A RED FLAG CONCERNING HRT IN POST-MENOPAUSAL WOMEN. COMBINED ESTROGEN AND PROGESTERONE USED LONG TERM SIGNIFICANTLY INCREASES THE RISK OF DEVELOPING BREAST CANCER BEYOND THE RISK OF ESTROGEN USED ALONE. THE AMERICAN HEART ASSOCIATION STRONGLY SUGGESTS THAT RISK FACTOR MANAGEMENT SUCH AS SMOKING CESSATION, BLOOD PRESSURE CONTROL AND LIPID MANAGEMENT SHOULD BE FIRST LINE MANAGEMENT PRIOR TO HRT AS IT RELATES TO CARDIOVASCULAR RISK FACTOR CONTROL.

THERE ARE RISKS AND BENEFITS OF HRT AND THERE ARE DIFFERENT TYPES OF HRT. THEREFORE, THIS MODALITY SHOULD ONLY BE USED UNDER THE STRICT GUIDANCE AND CONTROL OF YOUR HEALTHCARE PROFESSIONAL.

FIG.6L

| ANGER AND STRESS AFFECT THE CARDIOVASCULAR SYSTEM |
|---|
| MORE AND MORE DATA IS BECOMING AVAILABLE SHOWING THAT FEELINGS OF ANGER AND HOSTILITY AND FEELINGS OF DEPRESSION CAN NEGATIVELY IMPACT ONE'S CARDIOVASCULAR HEALTH. IT IS NOT KNOWN FOR SURE, BUT IT APPEARS THESE FEELINGS OF ANGER AND STRESS SET OFF PHYSIOLOGIC RESPONSES IN THE BODY THAT CAN RESULT IN MYOCARDIAL ISCHEMIA. THIS CAN TAKE THE FORM OF EITHER ANGINA OR ACTUALLY A HEART ATTACK. STUDIES HAVE SHOWN THAT SHORTLY AFTER HAVING AN ARGUMENT OR DEVELOPING FEELINGS OF ANGER DUE TO OTHER CONFLICTS, SUCH AS WITH FAMILY OR IN THE WORKPLACE, CAN RESULT IN CARDIOVASCULAR MANIFESTATIONS. INTERESTINGLY, IT APPEARS THAT TAKING AN ASPIRIN PRIOR TO THESE EVENTS CAN PROTECT AGAINST THESE EFFECTS. SIMILARLY, FEELINGS OF DEPRESSION APPEAR TO BE A STRONG PREDICTOR OF CARDIOVASCULAR DISEASE.<br><br>THERE IS SOME RECENT DATA DEMONSTRATING THAT COUNSELING AND BEHAVIOR MODIFICATION AS IT RELATES TO ANGER AND DEPRESSION MAY IMPROVE ONE'S CARDIOVASCULAR HEALTH. |

FIG. 6M

| LIPOPROTEIN (A) |
|---|
| RETROSPECTIVE STUDIES OF POPULATIONS OF PEOPLE INDICATE THAT HIGH LEVELS OF LIPOPROTEIN (A) ARE ASSOCIATED WITH INCREASED RISK OF PREMATURE CORONARY ARTERY DISEASE. CURRENTLY ONLY THE DRUG NIACIN IS KNOWN TO REDUCE LIPOPROTEIN LEVELS. IT IS NOT KNOWN WHETHER THIS REDUCTION IN LIPOPROTEIN (A) LEVELS CAN DECREASE THE INSTANCES OF CORONARY ARTERY DISEASE. PROSPECTIVE CLINICAL STUDIES WILL BE REQUIRED. |

FIG. 6N

HOMOCYSTEINE

THERE ARE MANY RISK FACTORS INFLUENCING THE DEVELOPMENT OF ATHEROSCLEROTIC VASCULAR DISEASE. ANOTHER RELATIVELY NEWLY RECOGNIZED RISK FACTOR FOR CORONARY DISEASE IS ELEVATED BLOOD LEVELS OF HOMOCYSTEINE. HOMOCYSTEINE IS AN AMINO ACID IN THE BLOODSTREAM. IT HAS BEEN KNOWN FOR YEARS THAT THERE IS A CONGENITAL DISEASE RESULTING IN EXTREMELY HIGH LEVELS OF HOMOCYSTEINE. THESE PEOPLE ARE KNOWN TO BE AT A VERY HIGH RISK FOR CORONARY DISEASE. MORE RECENTLY IT HAS BEEN RECOGNIZED THAT EVEN MINOR ELEVATIONS OF HOMOCYSTEINE MAY ALSO INCREASE ONE'S RISK OF CORONARY ARTERY DISEASE. THIS IS PARTICULARLY SO WITH PATIENTS WHO HAVE OTHER POSITIVE RISK FACTORS FOR DEVELOPING THIS DISEASE. A HYPOTHESIS IS THAT HOMOCYSTEINE DAMAGES ARTERIAL WALLS MAKING THEM MORE LIKELY TO BECOME TARGETS FOR THE DEVELOPMENT OF CORONARY ARTERY DISEASE.

THERE IS ONE ESTIMATE THAT 20 MILLION AMERICANS HAVE ELEVATED LEVELS OF HOMOCYSTEINE. THE GOOD NEWS IS THAT THERE ARE WAYS TO LOWER ONE'S HOMOCYSTEINE LEVELS. THIS INVOLVES THE INGESTION OF FOLIC ACID, VITAMIN B6 AND B12. ONE WAY TO ACCOMPLISH THIS IS BY EATING LEAFY GREEN VEGETABLES, FRUIT, AND LEGUMES. ANOTHER VERY EFFECTIVE WAY IS TO EAT A FORTIFIED CEREAL. IN FACT THE ONLY FOOD THAT CONTAINS ALL THREE VITAMINS IS A READY TO EAT, FORTIFIED CEREAL.

WHAT IS FOLIC ACID? FOLIC ACID IS ONE OF THE B VITAMINS. IT IS FOUND IN GREEN LEAFY VEGETABLES. THE BODY USES FOLIC ACID TO BUILD NEW CELLS AND REPAIR DAMAGED CELLS. IN ADDITION, IT IS ALSO ESSENTIAL FOR CONSTRUCTION BY THE BODY OF DNA. THE DAILY RECOMMENDED VALUE OF FOLIC ACID IS 400 MICROGRAMS. AS MENTIONED ABOVE, GREEN LEAFY VEGETABLES HAVE LARGE AMOUNTS OF FOLIC ACID. OTHER SOURCES INCLUDE: NUTS, LEGUMES, CERTAIN FRUIT AND GRAIN FOODS.

IF ONE WISHES TO OBTAIN THESE VITAMINS (FOLIC ACID, VITAMIN B6, VITAMIN B12) BY EATING VEGETABLES, FRUIT AND LEGUMES, IT IS IMPORTANT TO UNDERSTAND THAT PROLONGED HEATING OR BOILING OF THESE SUBSTANCES OR MICROWAVE HEATING MAY REDUCE LEVELS OF THESE VITAMINS.

INDIVIDUALS WHO INGEST THESE THREE IMPORTANT VITAMINS ARE USUALLY WELL PROTECTED AND THEREFORE ACTUALLY MEASURING BLOOD LEVELS IS NOT REQUIRED. A RECENTLY PERFORMED STUDY PUBLISHED IN THE NEW ENGLAND JOURNAL OF MEDICINE SHOWED AN AVERAGE OF 11% DECREASE IN HOMOCYSTEINE LEVELS WITH A 15 WEEK COURSE OF EATING 3/4 CUP OF TOTAL CEREAL PER DAY. IT SHOULD BE NOTED HOWEVER THAT THERE ARE NO WELL CONTROLLED STUDIES CONCLUSIVELY SHOWING THAT DECREASING HOMOCYSTEINE LEVELS WILL RESULT IN A LOWER LEVEL OF CORONARY ARTERY DISEASE. THESE TYPES OF STUDIES ARE CURRENTLY ONGOING.

FIG. 6O

VITAMIN E AND OTHER ANTIOXIDANT VITAMINS MAY AFFECT CORONARY DISEASE

THERE IS MUCH EVIDENCE THAT CHOLESTEROL IS A MAJOR COMPONENT OF ATHEROSCLEROTIC PLAQUE BUILD-UP. CHOLESTEROL IS CARRIED TO THE PLAQUE IN THE FORM OF LDL CHOLESTEROL. THERE IS EVIDENCE THAT THIS CHOLESTEROL MUST FIRST BE OXIDIZED BEFORE IT ACTUALLY ENTERS THE PLAQUE AND PARTICIPATES IN PLAQUE BUILD-UP. THERE IS SPECULATION THAT ANTI-OXIDANT VITAMINS SUCH AS VITAMIN C, E, AND BETA-CAROTENE MAY PREVENT PLAQUE FORMATION BY INTERFERING WITH THIS OXIDATION. TO PUT IT ANOTHER WAY, IT IS POSSIBLE THAT ANTI-OXIDANT VITAMINS CAN PREVENT OR REDUCE CORONARY ARTERY DISEASE.

THE EVIDENCE FOR THIS IS STRONGEST FOR VITAMIN E. THERE ARE SOME STUDIES THAT SUGGEST THAT VITAMIN E TAKEN IN RELATIVELY LARGE DOSES AS A DIETARY SUPPLEMENT MAY FUNCTION TO INHIBIT THE ATHEROSCLEROTIC PROCESS. IT SHOULD BE NOTED THAT ONE CANNOT GET ENOUGH VITAMIN E FROM NORMAL DIETARY INTAKE TO BE EFFECTIVE, THEREFORE DIET SUPPLEMENTATION MUST BE USED. THE EVIDENCE FOR VITAMIN C AND BETA-CAROTENE FUNCTIONING IN THIS MODE IS QUITE A BIT LESS.

IT SHOULD BE NOTED THAT THERE ARE ONGOING STUDIES TRYING TO ESTABLISH WHETHER ANTI-OXIDANT VITAMINS, PARTICULARLY VITAMIN E, ARE IN FACT USEFUL FOR DECREASING CORONARY DISEASE. THERE IS CONFLICTING DATA IN THIS REGARD. IT SHOULD ALSO BE NOTED THAT THERE HAVE BEEN NO LONG-TERM STUDIES SHOWING THE SAFETY OF TAKING VITAMIN E IN RELATIVELY LARGE DOSES FOR LONG PERIODS OF TIME. YOUR HEALTHCARE PROFESSIONAL COULD HELP WITH THIS.

FIG. 6P

| ALCOHOL CONSUMPTION |
|---|
| A NUMBER OF STUDIES HAVE RECENTLY SHOWN THAT MODERATE ALCOHOL INTAKE (ABOUT 1- 3 DRINKS PER DAY) IS ASSOCIATED WITH A LOWER RISK OF CORONARY ARTERY DISEASE THAN IN THOSE WHO ARE ABSTINENT.<br><br>THERE IS STILL MUCH TO BE LEARNED ABOUT THIS ASSOCIATION. SOME STUDIES SUGGEST THAT IT IS THE ALCOHOL ALONE THAT CAUSES THIS EFFECT. THIS WOULD IMPLY THAT BEER, WINE OR SPIRITS ALL OFFER THE SAME PROTECTION. OTHER STUDIES STRONGLY SUGEGST THAT RED WINE OFFERS THE MOST PROTECTION. IT IS BELIEVED THAT SUBSTANCES CALLED FLAVINOIDES ARE THE RESPONSIBLE AGENT. THE WEBSITE WWW.ANTI-OXIDANT.COM CAN GIVE MORE INFORMATION ABOUT THIS.<br><br>ANOTHER AREA OF CONTROVERSY CONCERNS THE QUANTITY OF ALCOHOL REQUIRED FOR THIS BENEFIT. THESE STUDIES ARE STILL BEING DONE.<br><br>CAUTION!!<br><br>EXCESS ALCOHOL CONSUMPTION CAN BE HIGHLY DESTRUCTIVE TO PHYSICAL AND PSYCHOLOGICAL HEALTH. THEREFORE, THE ISSUE OF ALCOHOL CONSUMPTION AS IT RELATES TO CORONARY ARTERY DISEASE RISK SHOULD BE DISCUSSED WITH ONE'S HEALTHCARE PROFESSIONAL. |

FIG. 6Q

| AGE |
|---|
| IN AMERICA AND OTHER WESTERN POPULATIONS THE INCIDENCE OF CORONARY DISEASE INCREASES WITH ADVANCING AGE. MALES HAVE A HIGHER RATE OF DEVELOPING CORONARY DISEASE THAN FEMALES UNTIL ABOUT AGE 75, WHEN THE PREVALENCE OF CORONARY DISEASE IS ABOUT EQUAL BETWEEN THE SEXES. MALES LESS THAN 55 YEARS OF AGE DEVELOP CORONARY DISEASE AT A RATE OF 3-4 FOLD GREATER THAN FEMALES. HOWEVER AFTER AGE 55 THE RATE DECREASES FOR MEN AND INCREASES FOR WOMEN. |

FIG. 6R

| FAMILY HISTORY |
|---|
| POSITIVE FAMILY HISTORY, ACCORDING TO THE NATIONAL CHOLESTEROL EDUCATION PROGRAM IS DEFINED AS HAVING A FIRST DEGREE MALE RELATIVE DEVELOP A DEFINITE HEART ATTACK OR DIE SUDDENLY BEFORE THE AGE OF 55. THIS WOULD INCLUDE INDIVIDUALS SUCH AS A FATHER OR BROTHER. POSITIVE FAMILY HISTORY IS ALSO PRESENT IF A FIRST DEGREE FEMALE RELATIVE DEVELOPS A DEFINITE HEART ATTACK OR DIES SUDDENLY BEFORE THE AGE OF 65. |

FIG. 6S

| KNOWN CORONARY ARTERY DISEASE |
|---|
| INDIVIDUALS WHO HAVE KNOWN CORONARY ARTERY DISEASE SUCH AS ANGINA, HEART ATTACK, PREVIOUS CORONARY BYPASS SURGERY OR ANGIOPLASTY, ALL HAVE A HIGHER RISK OF DEVELOPING FUTURE CORONARY ARTERY EVENTS. |

| KNOWN VASCULAR DISEASE |
|---|
| INDIVIDUALS WHO HAVE BLOCKAGES IN ARTERIES GOING TO OTHER PARTS OF THE BODY SUCH AS THE BRAIN, LEGS OR ABDOMINAL ORGANS, HAVE AN INCREASED RISK OF DEVELOPING CORONARY ARTERY DISEASE. |

FIG. 6T

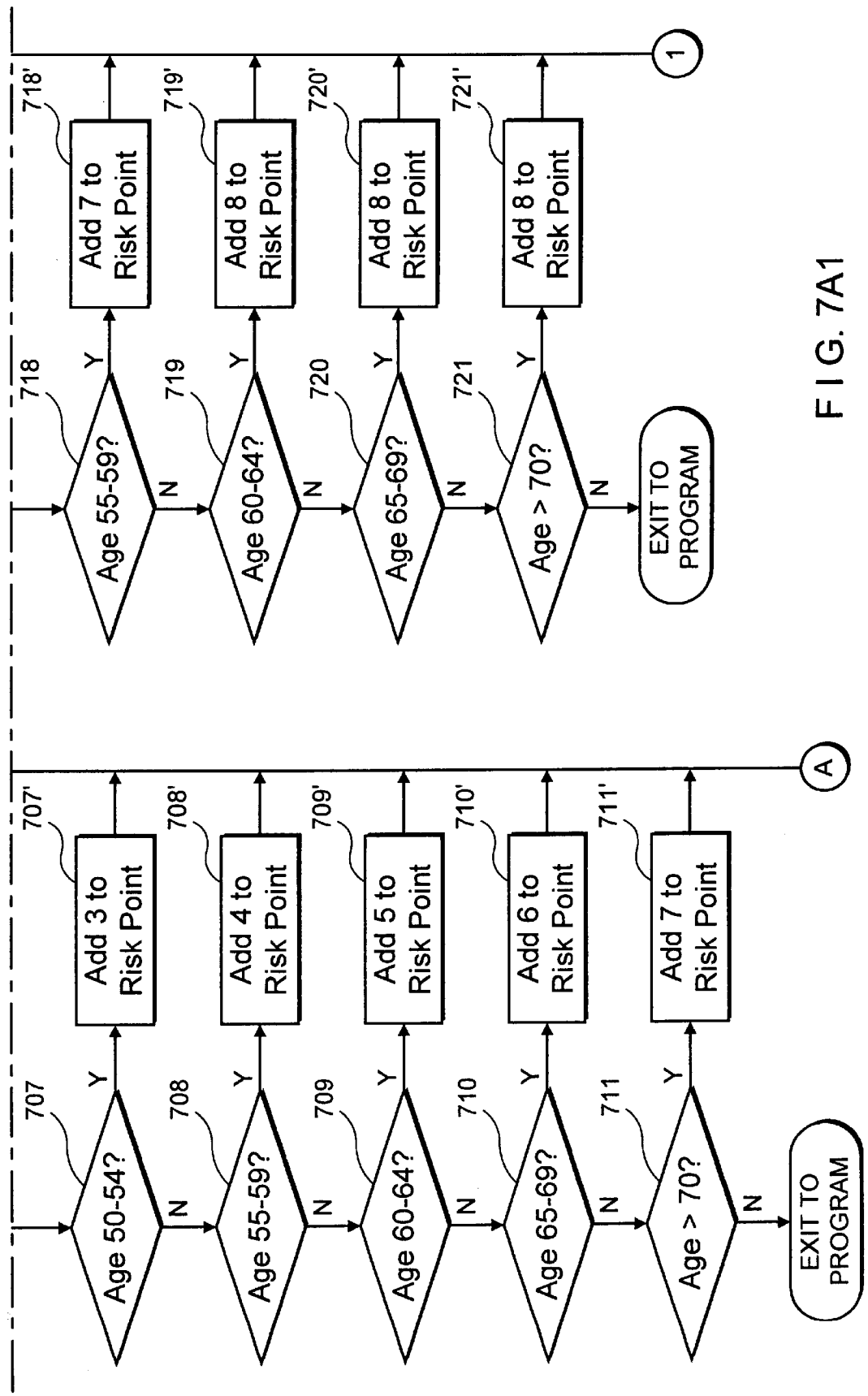
FIG. 7A1

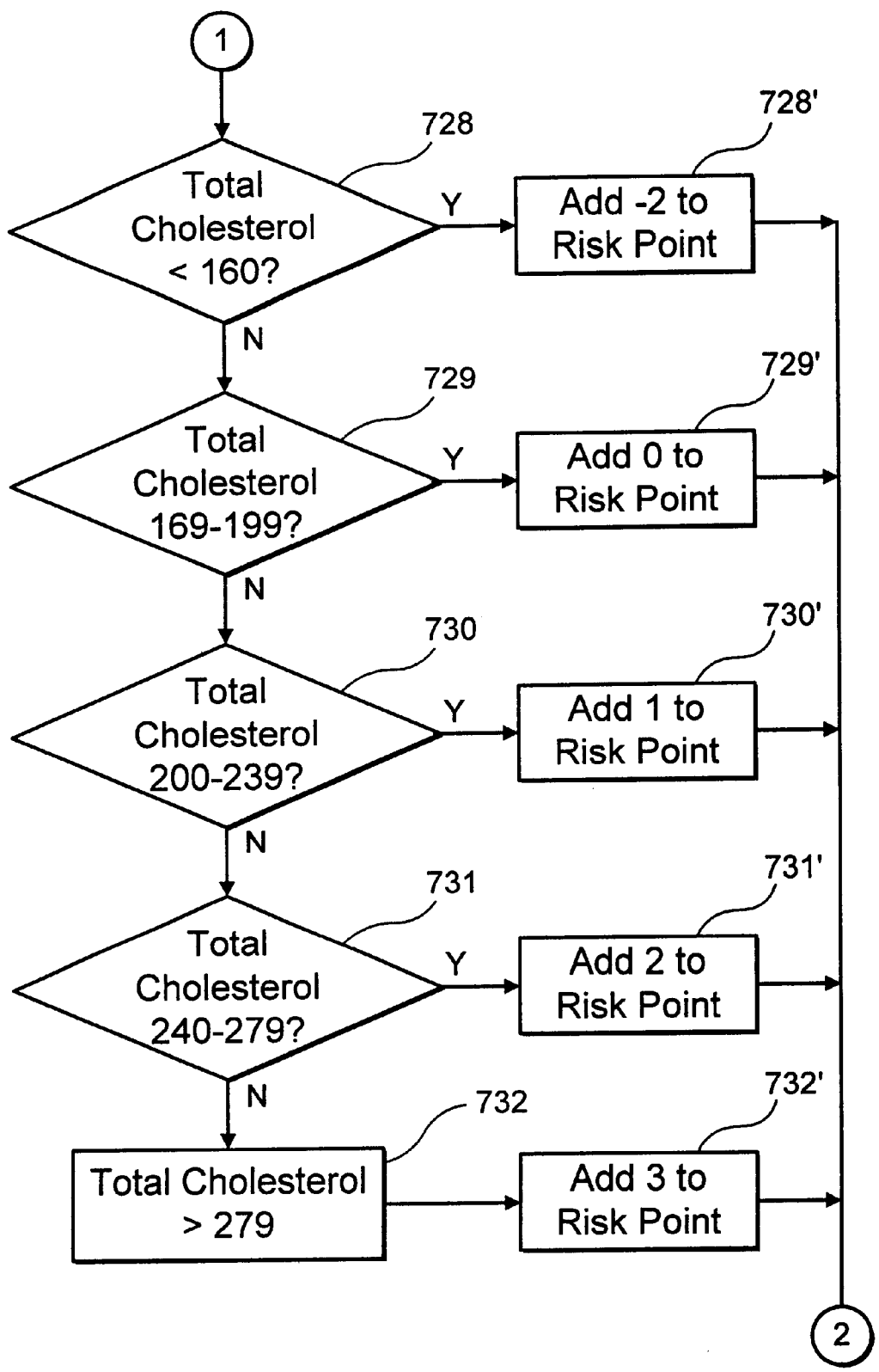
FIG. 7B1

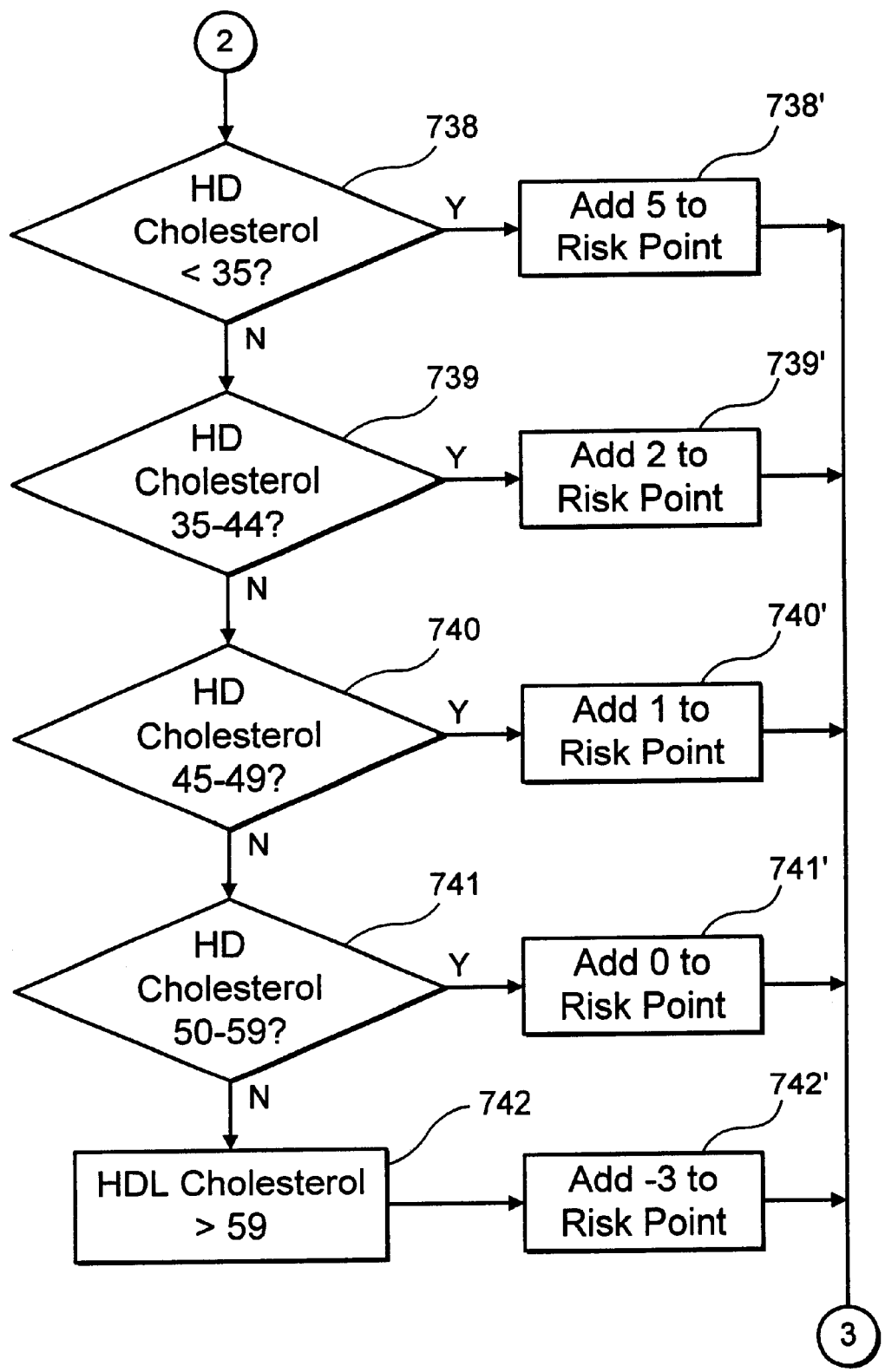
FIG. 7C1

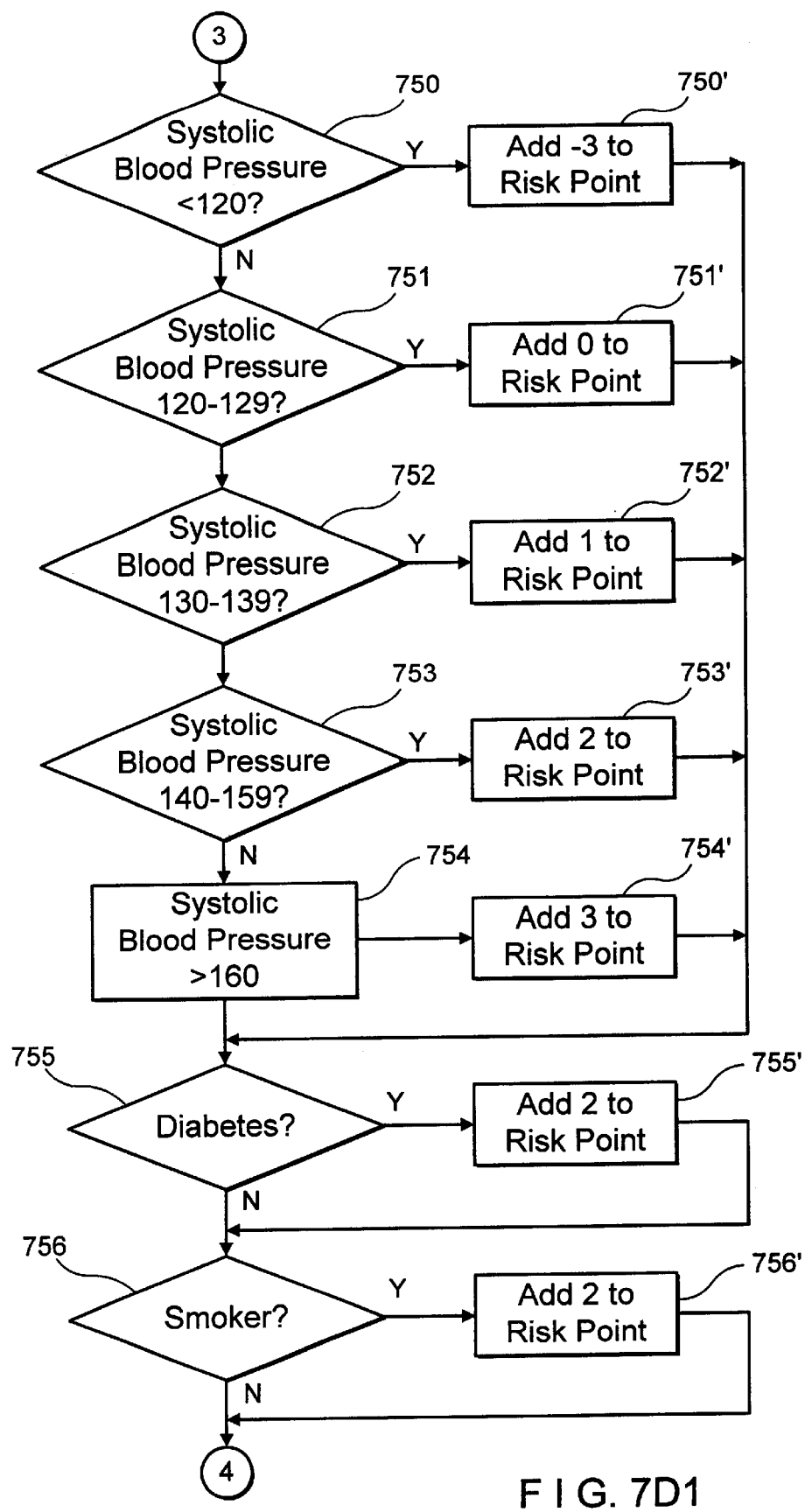
FIG. 7D1

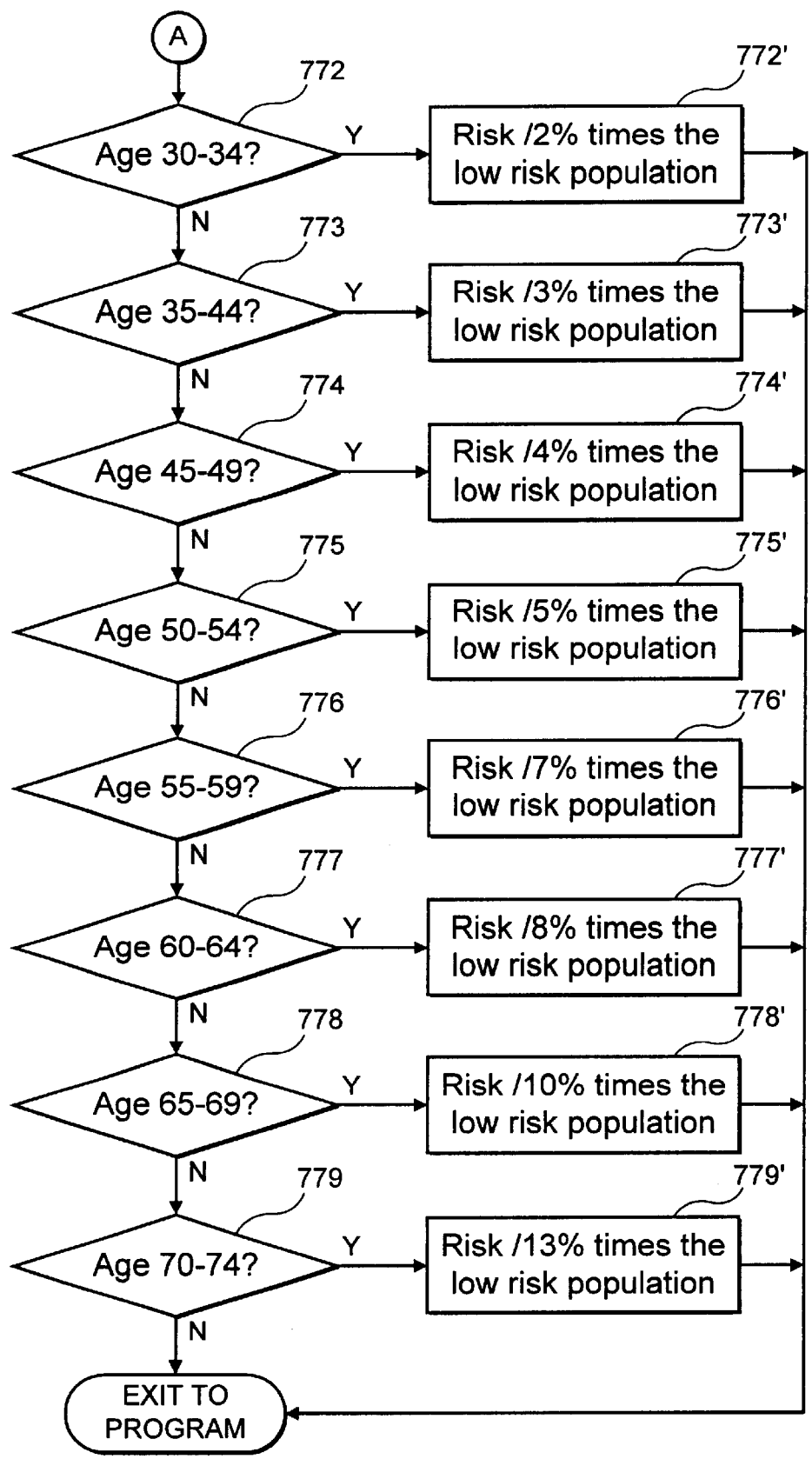
F I G. 7E1

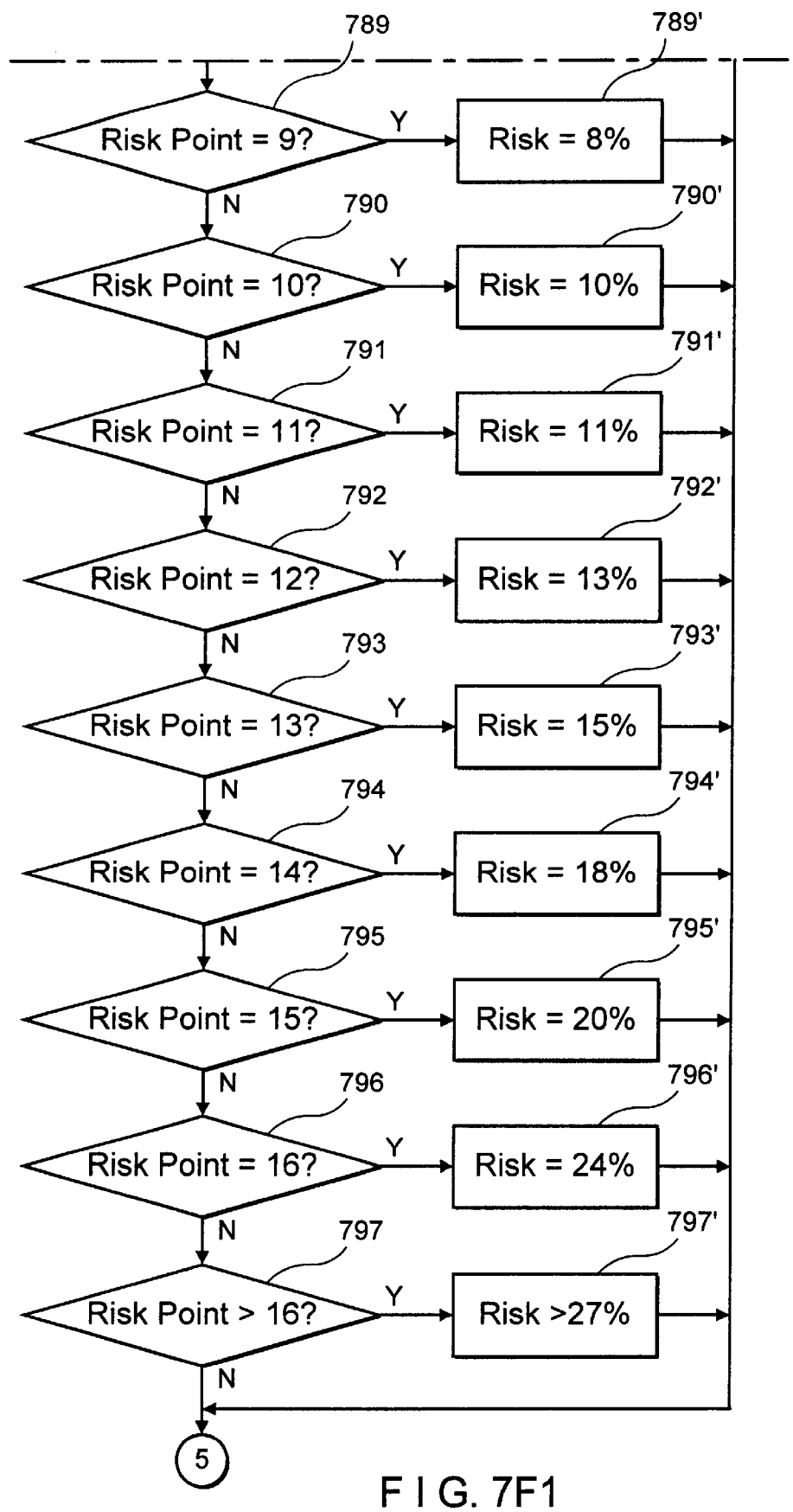
FIG. 7F1

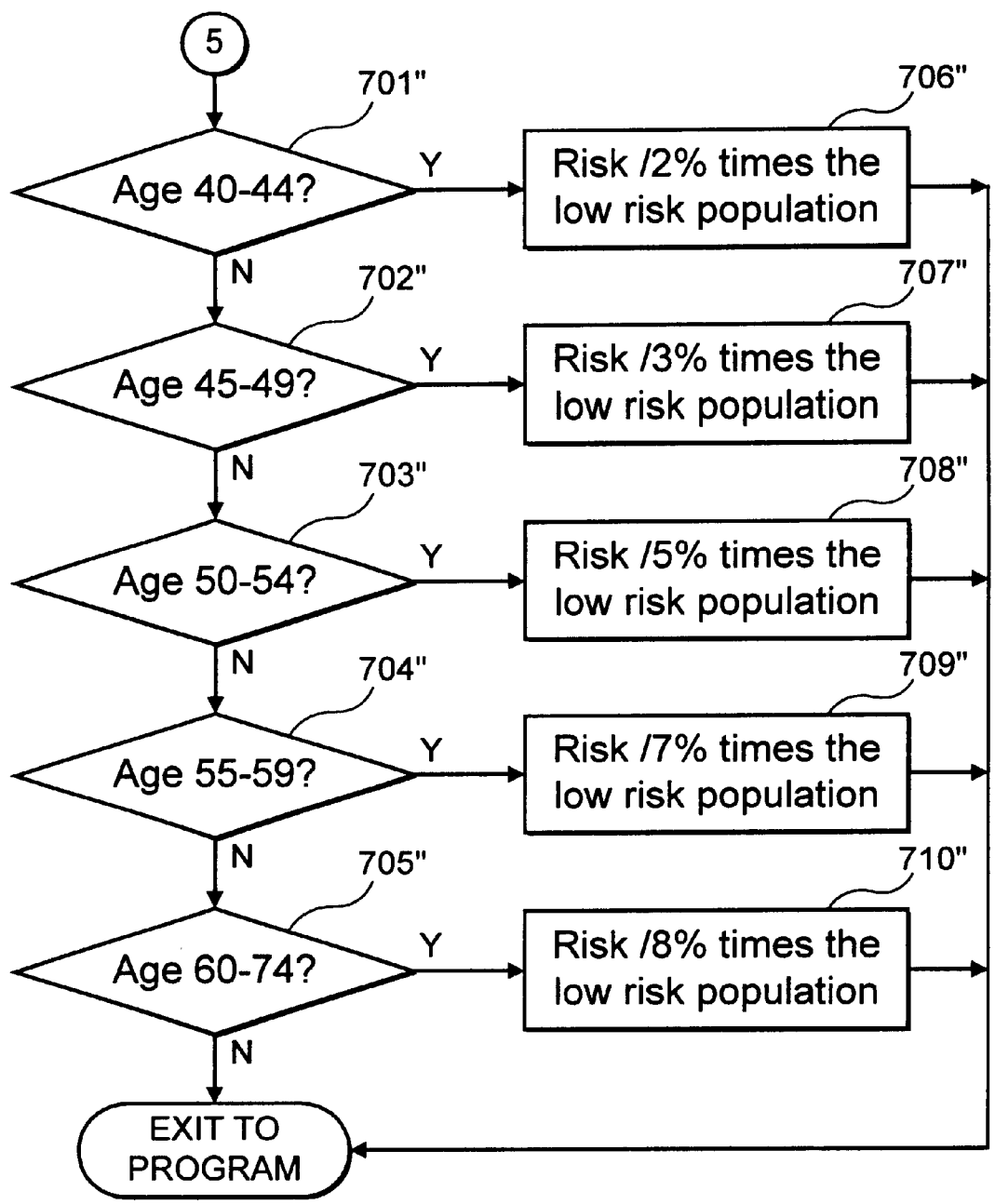
FIG. 7F2

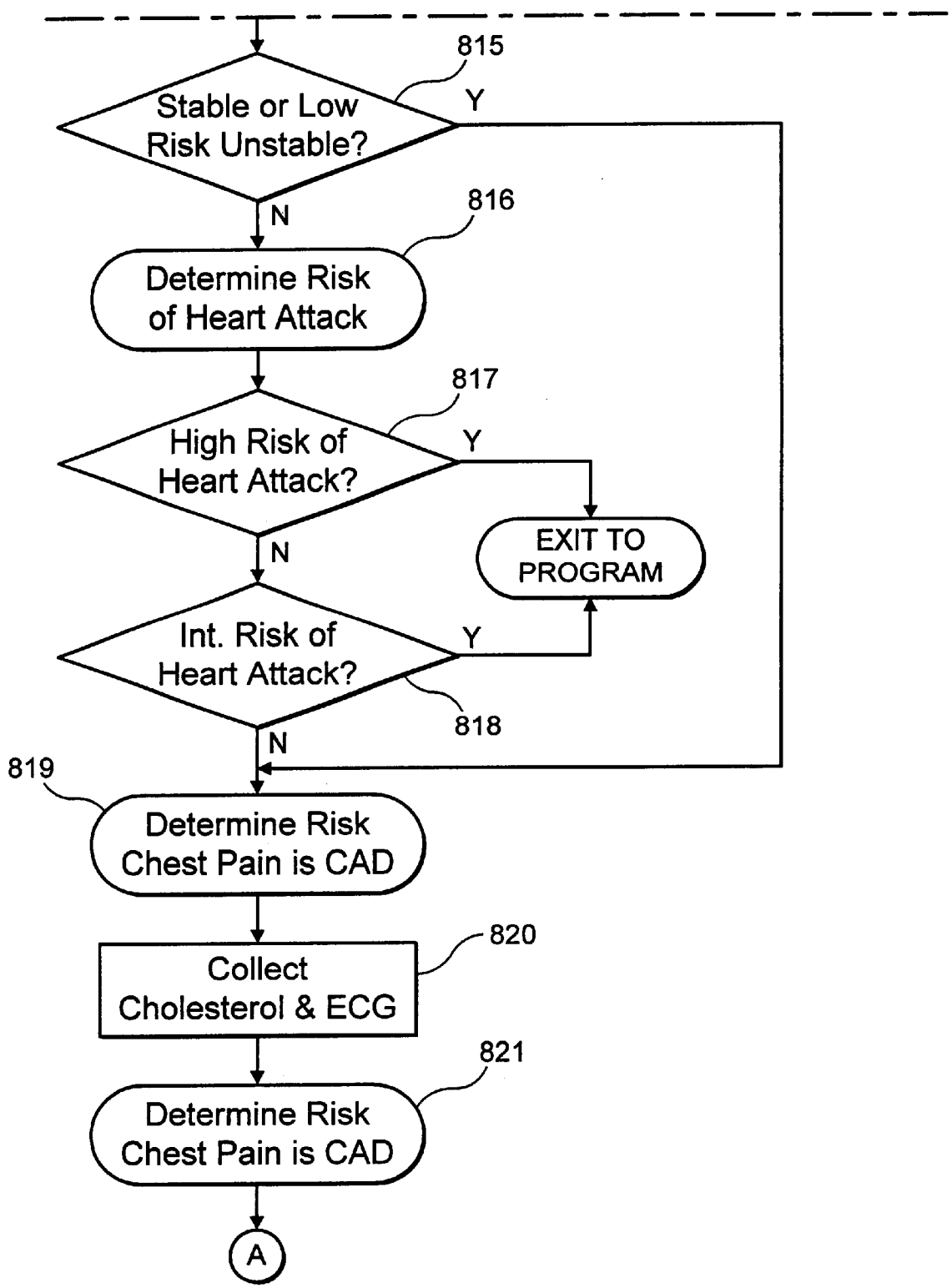
F I G. 8(2)

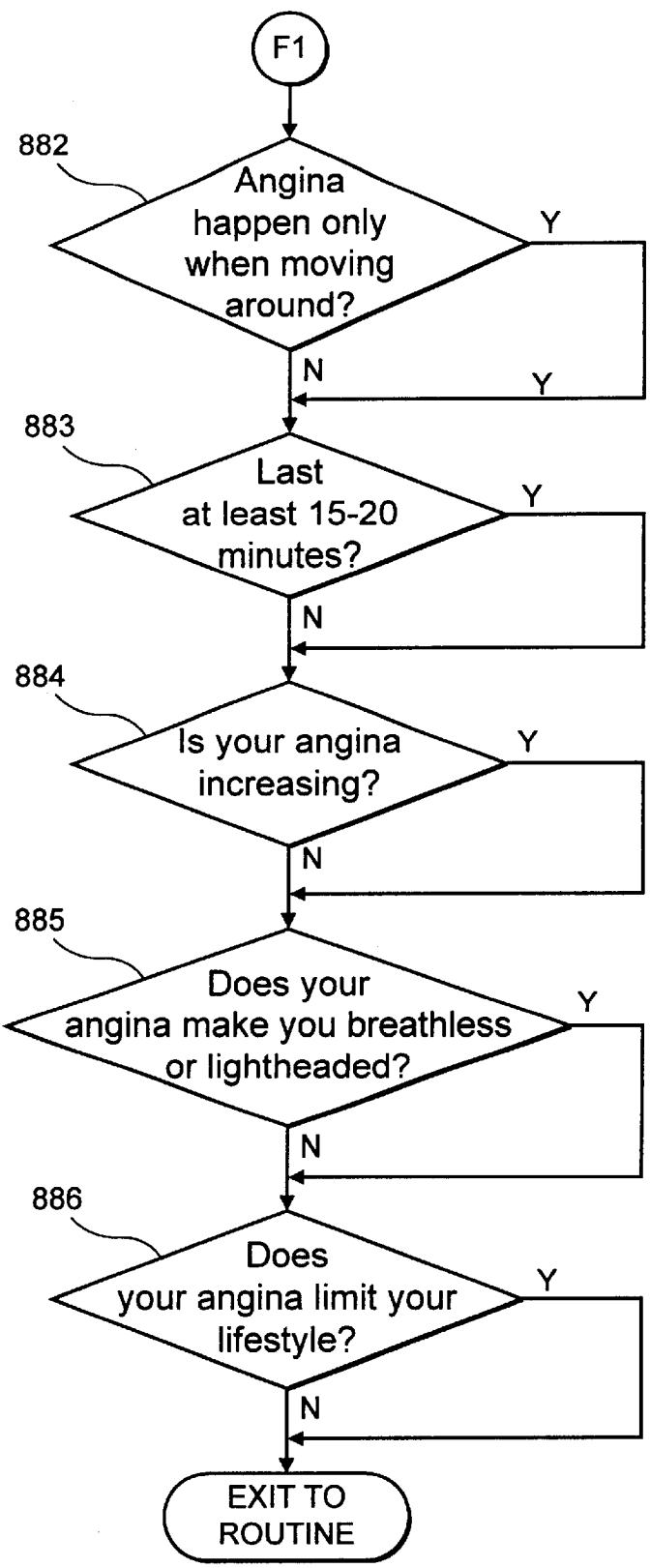
FIG. 8F1

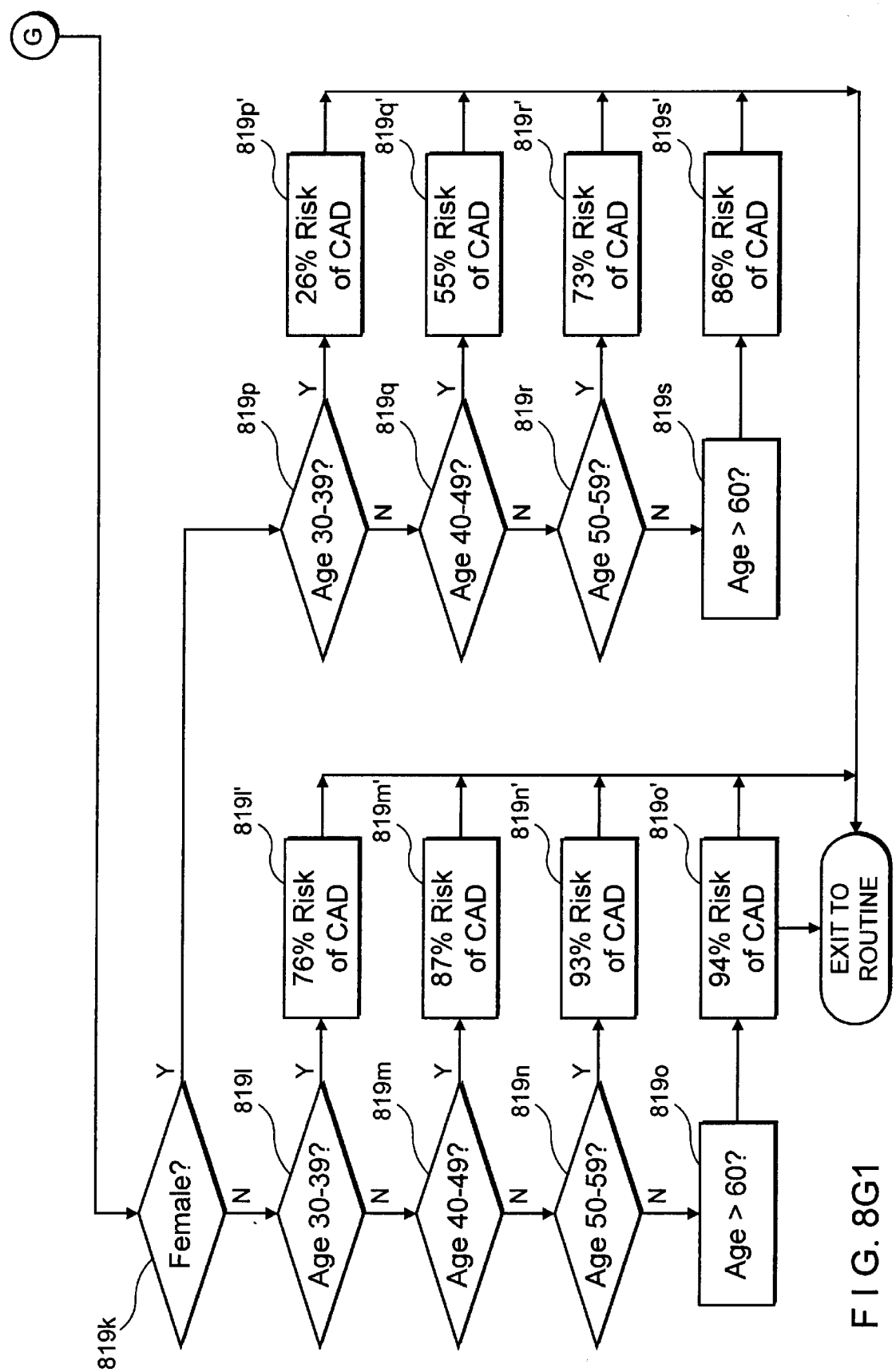
FIG. 8G1

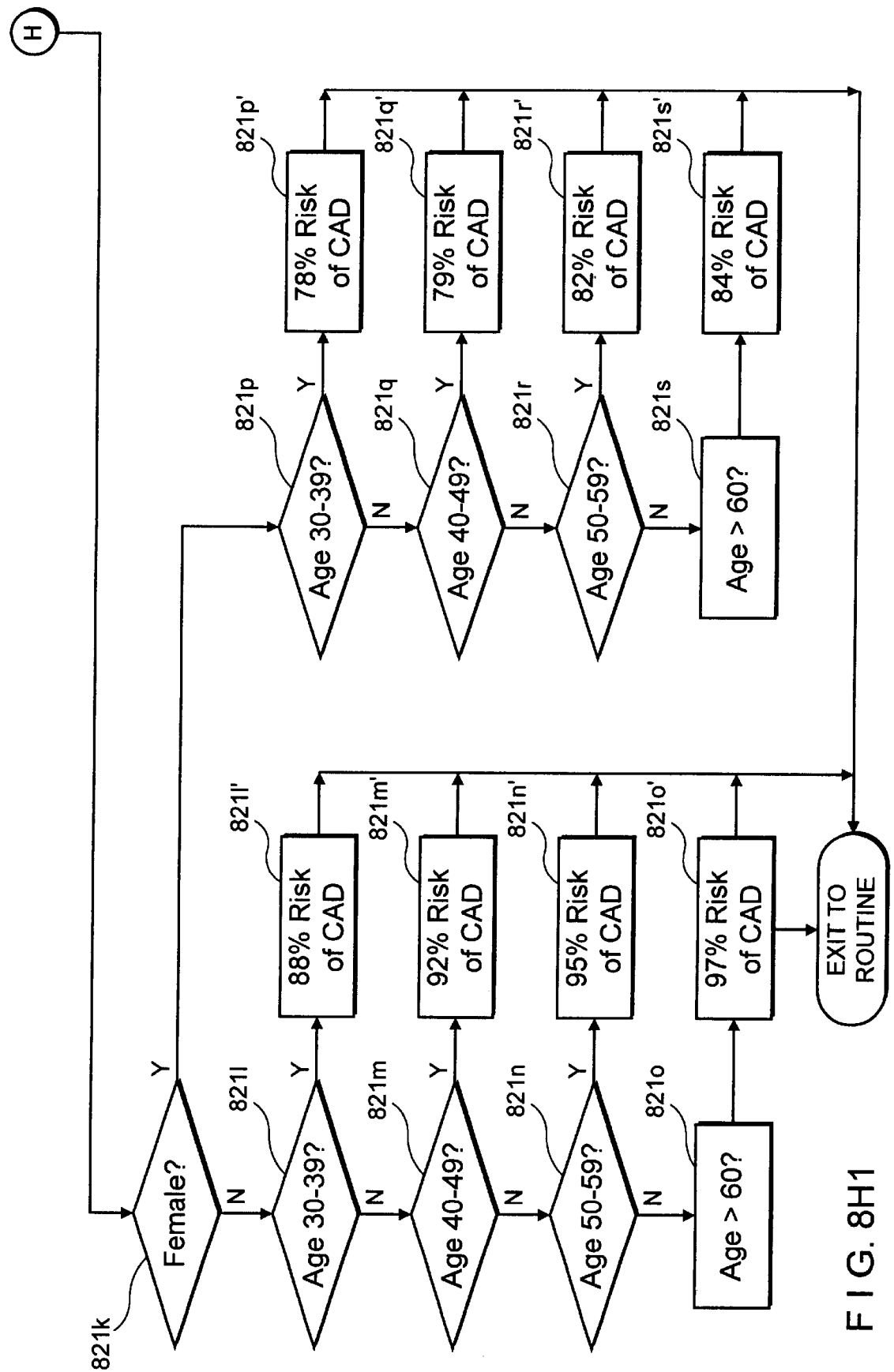
FIG. 8H1

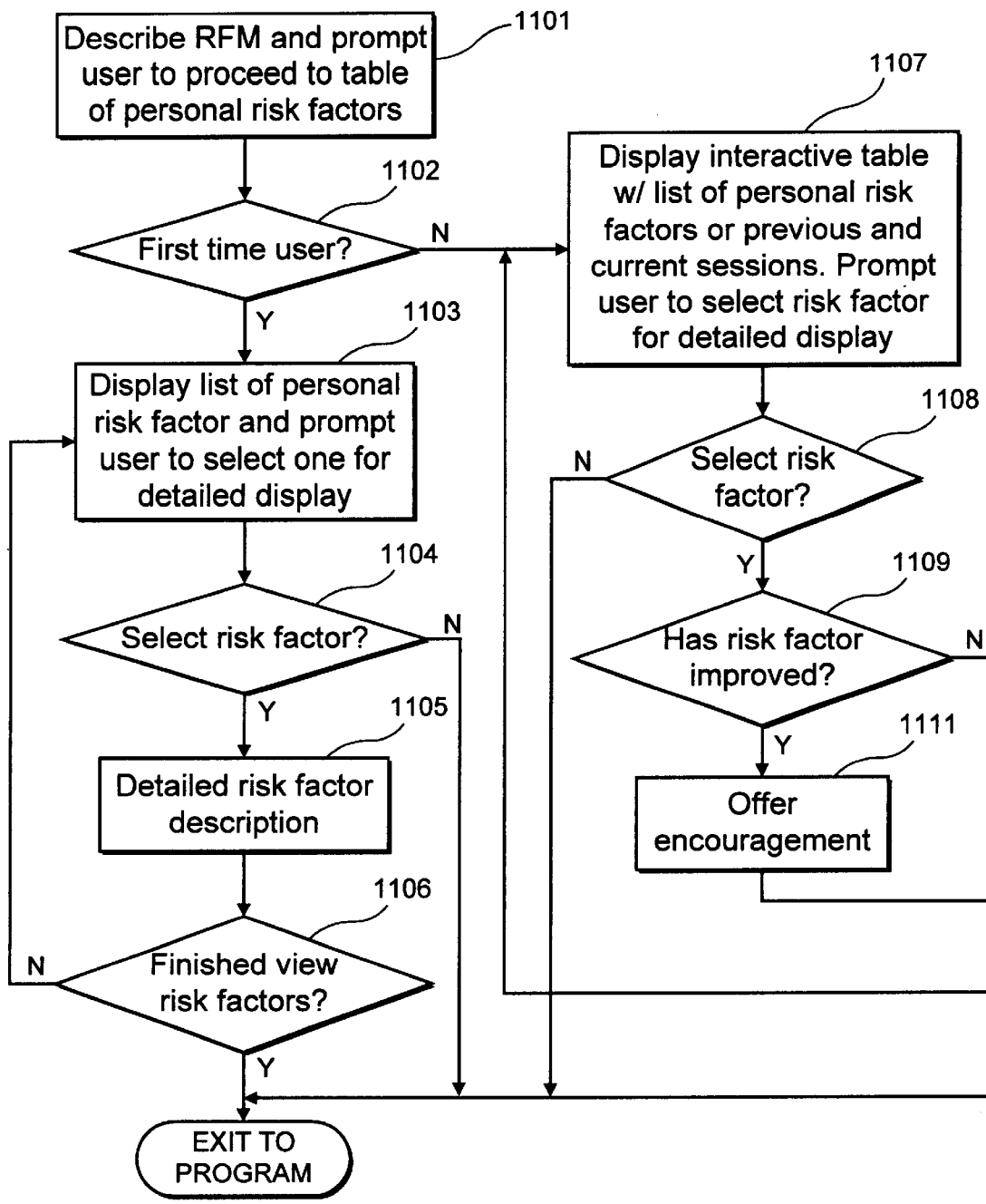
F I G. 11

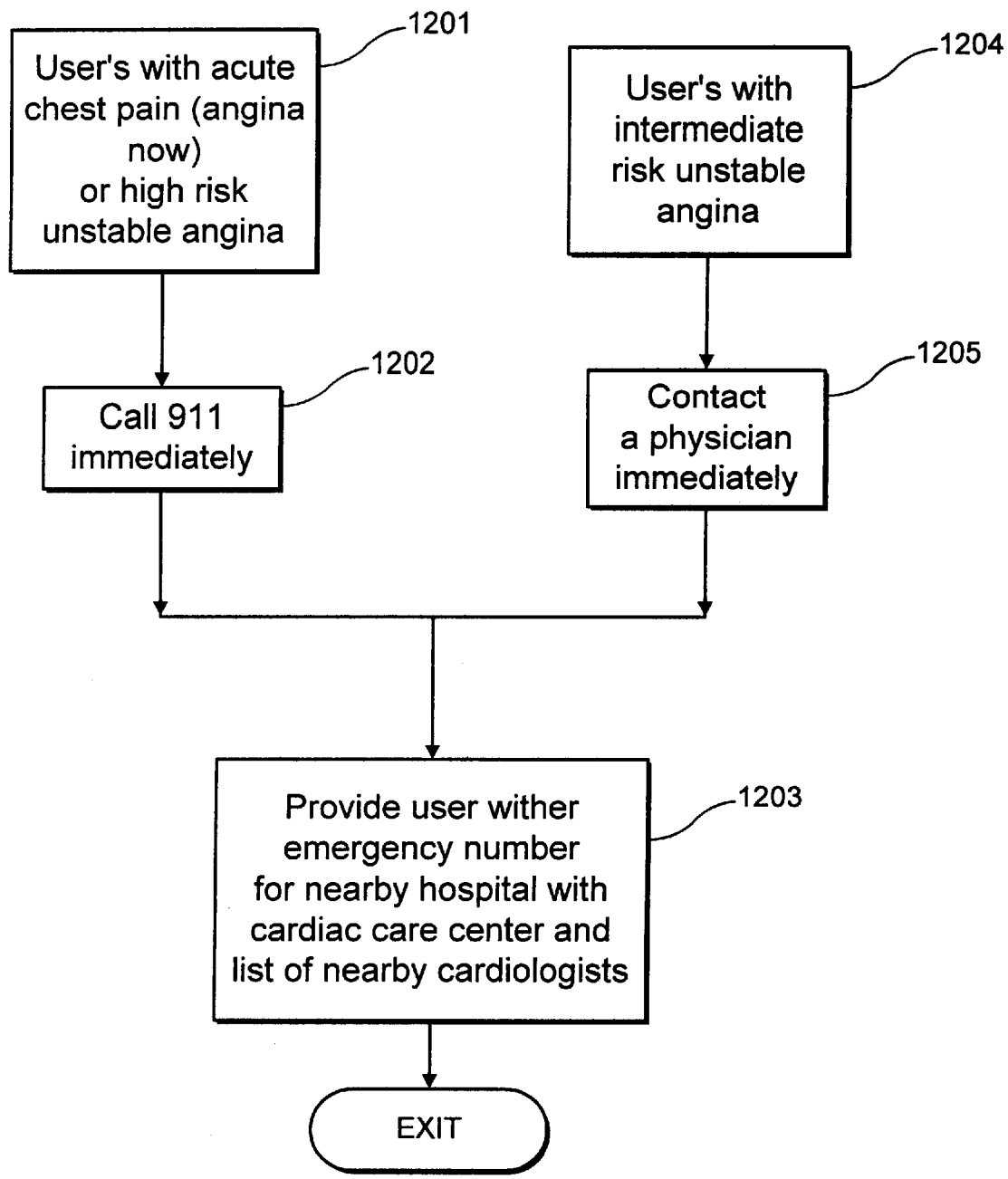
F I G. 12

COMPUTERIZED INTERACTIVE METHOD AND SYSTEM FOR DETERMINING A RISK OF DEVELOPING A DISEASE AND THE CONSEQUENCES OF DEVELOPING THE DISEASE

FIELD OF THE INVENTION

The present invention relates to a method and a system for determining a risk of developing a disease and the consequences of having the disease, in particular, an interactive computerized method and system for determining the risk of developing coronary artery disease and the consequences of having the disease.

BACKGROUND INFORMATION

Coronary artery disease (CAD) is the leading cause of death for Americans today. Approximately twenty percent (20%) of all American deaths are due to CAD. It is estimated that sixteen (16) million Americans per year are treated for CAD, and one million of these will suffer a heart attack.

Risk factor modification (RFM) and preventive medicine are becoming a major trend as it relates to modifying an individual's risk of developing a disease. For example, RFM for CAD encompasses many aspects of daily life such as smoking cessation, obesity reduction, exercise, lipid management, dietary modification and supplementation, and taking an aspirin a day. Individuals have recognized the importance of a healthy lifestyle. Indeed, physicians are under increasing pressure from the government, medical specialty organizations, managed care and patients to practice preventive medicine. Moreover, managed care and insurance companies have recognized that RFM is a very cost effective strategy. Unfortunately studies show that little progress has been made in the area of RFM and preventive medicine—especially with regard to cardiovascular health.

Practice guidelines have been developed and/or published by the American College of Cardiology and American Heart Association, the U.S. Department of Health and Human Services Agency for Healthcare Policy and Research (AHCPR), and the National Heart, Lung and Blood Institute. These guidelines provide algorithms for risk assessment and modification. The practice guidelines, however, are cumbersome, difficult to use, and not readily accessible to or understood by patients. Thus, there is a need to bring RFM to the forefront and simplify the information provided in the practice guidelines.

The Internet and world wide web (WWW) have become major factors in providing healthcare information and resources. Web sites such as, WebMD.com, Medscape.com, Dr.Koop.com, Realage.com and cardassoc.com, provide both physicians and users with valuable healthcare information. These web sites can be categorized into one of four types:

1. Informational,
2. E-mail,
3. Questionnaire, and
4. Combinational.

Informational type web sites typically provide encyclopedia-like healthcare information. Informational web sites, however, are generally difficult to navigate because they provide an individual with huge amounts of information, which must be sifted through. E-mail type web sites allow a user to type in questions that are answered by physicians at a host site. The users, however, are only provided with cursory answers to their questions. Questionnaire type web sites typically ask the user a series of questions to assess the user's health. None of these web sites provide the user with contemporaneous feedback regarding risk factors for a particular disease based on the information that is provided by the user. Finally, none of these web sites track the user's progress as his or her health status improves or deteriorates. Thus, it would be useful to provide an interactive web site that allows a user to provide detailed information regarding a disease, determines an individual's risk of developing the disease, determines the risks associated with the disease if the individual already has the disease, provides ways in which the individual can decrease his or her risk of developing the disease, and tracks the individual's progress with respect to modification of his or her risk factors.

SUMMARY OF THE INVENTION

The interactive computerized method and system according to the present invention determines an individual's risk of developing a disease, for example CAD, or the individual's risk associated with the disease if the individual already has the disease, and provides RFM information to the user. The method and system according to the present invention also tracks the individual's progress in modifying his or her risk factors. The computerized method and system is implemented via a computer operating either in a stand alone mode or in any conventional networking environment, such as the Internet, WWW or local area network (LAN). The computer accesses a program that implements the method according to the present invention. The program may be accessed by a user, for example, an individual providing his own information or another's information.

The program may be written in a conventional programming language, such as C++ or hypertext markup language. The program determines the individual's risk of developing the disease and provides ways for the individual to modify his or her risk.

The program implements several sections. One section determines the individual's risk for developing the disease. The user accesses this section of the program via a login routine. After logging in, the user is asked a series of questions regarding known risk factors for the disease, for example physical characteristics, lifestyle information and medical history. As the user answers the question, the user is advised if the user's response is a positive or negative risk factor with respect to the disease. Based on the information provided by the user, statistical models about risk significant events and practice guidelines for the disease, the individual's risk for developing that disease is determined, or if the individual already has the disease, the associated consequences of having the disease are determined.

Another section of the program deals with RFM. Once the individual's risk is assessed, the user is provided a summary of the individual's risk factors and may learn about ways for the individual to modify his or her risk of developing the disease.

A third section of the program is accessed on a user's subsequent visits to the program. In this section, the user's current responses are compared to the user's previous responses to provide feedback to the user and to monitor the individual's progress.

The information provided by individual's accessing the program may be used, for example, in future studies.

In the example embodiment, CAD is the disease for which the risk is determined and RFM is provided.

BRIEF DESCRIPTION OF THE DRAWINGS

FIG. 3B illustrates an example embodiment of a screen display for registration of first-time user of the program shown in FIG. 2.

FIG. 4A illustrates a screen display of a first portion of the preliminary assessment of chest pain section.

FIG. 5F shows an example embodiment of an opening screen display for the risk factor collection section or risk factor modification section modification section shown in FIG. 2.

FIG. 5G shows an example embodiment of a screen display for the collection of an individual's physical characteristics.

FIG. 5H shows an example embodiment of a first screen display for the collection of an individual's lifestyle information.

FIG. 5I shows an example embodiment of a second screen display for the collection of an individual's lifestyle information.

FIG. 6A illustrates an example embodiment of a screen display of a personal risk factor summary.

FIG. 6B illustrates various advisor screens indicating a positive risk factor.

FIG. 6C illustrates a screen display of information regarding smoking as a risk factor.

FIG. 6D illustrates a screen display of information regarding dyslipidemia as a risk factor.

FIG. 6E illustrates a screen display of information regarding hypertension as a risk factor.

FIG. 6F illustrates a screen display of information regarding left ventricular hypertrophy as a risk factor.

FIG. 6G illustrates a screen display of information regarding the non-use of aspirin as a risk factor.

FIG. 6H illustrates a screen display of information regarding diabetes as a risk factor.

FIG. 6I illustrates a screen display of information regarding obesity as a risk factor.

FIG. 6J illustrates a first screen display of information regarding lack of physical activity as a risk factor.

FIG. 6K illustrates a second screen display of information regarding lack of physical activity as a risk factor.

FIG. 6L illustrates a screen display of information regarding hormone replacement therapy as a risk factor.

FIG. 6M illustrates a screen display of information regarding anger and stress as a risk factor.

FIG. 6N illustrates a screen display of information regarding levels of lipoprotein as a risk factor.

FIG. 6O illustrates a screen display of information regarding levels of homocysteine as a risk factor.

FIG. 6P illustrates a screen display of information regarding non-use of antioxidant vitamins as a risk factor.

FIG. 6Q illustrates a screen display of information regarding alcohol consumption as a risk factor.

FIG. 6R illustrates a screen display of information regarding age as a risk factor.

FIG. 6S illustrates a screen display of information regarding family history as a risk factor.

FIG. 6T illustrates a first screen display of information regarding known coronary artery disease as a risk factor, and a second screen display of information regarding known vascular disease as a risk factor.

FIG. 12 illustrates a flow chart for the 911 section shown in FIG. 2.

DETAILED DESCRIPTION

System Overview

Figure 1:
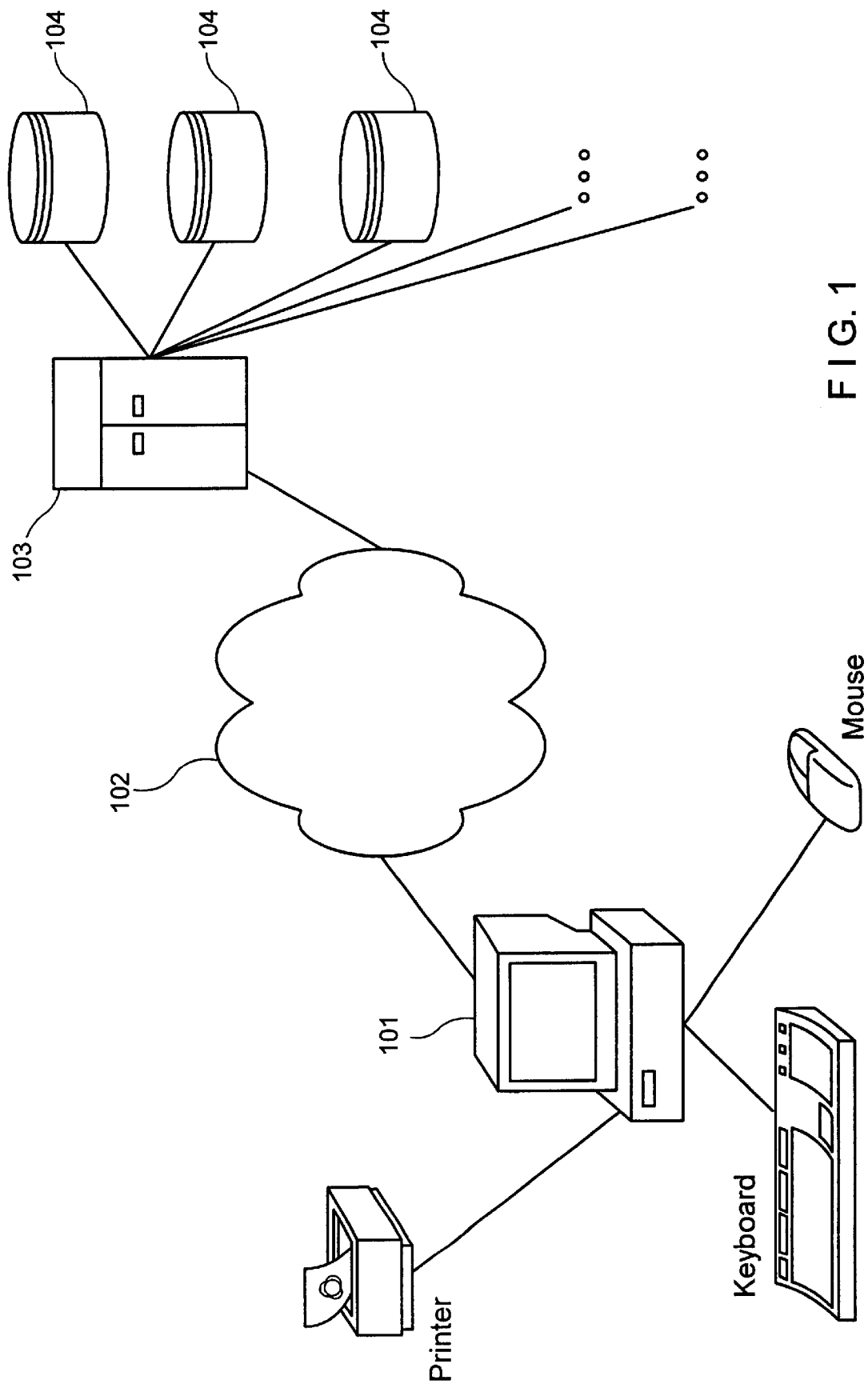
FIG. 1 illustrates a system in which a method according to the present invention may be implemented.

FIG. 1 illustrates a system in which a method according to the present invention may be implemented. The system illustrated is implemented as an Internet application; however, the present invention is compatible with any type of information network, public or private. Thus, the present invention may be implemented using a private Intranet, local area network (LAN), metropolitan area network (MAN), wide area network (WAN) or even a wireless network. The present invention may even be implemented in a stand alone mode.

The example system shown in FIG. 1 includes a user computer system, such as a personal computer system 101, and a server computer system 103. The personal computer includes a central processing unit (CPU) including memory and storage, input devices, and output devices. The CPU runs a conventional operating system, such as Microsoft Windows 2000, 1998 or NT, and a web browser such as Microsoft Internet Explorer or Netscape. The input devices include, for example, a keyboard, mouse, touch-screen, floppy drive and/or CD-ROM drive. The output devices include, for example, a monitor and/or printer.

The server computer system 103, like the personal computer system, includes a CPU, input devices, and output devices. The server computer system also includes memory and storage devices 104, which store, for example, databases. The server computer system 103 runs an operating system and a program implementing a method according to the present invention. The personal computer system 101 and the server computer system 103 communicate via a communications link 102, such as, a modem, T1 line or POTS line, the Internet, and a T1 line.

Overall System Flowchart

Figure 2A:
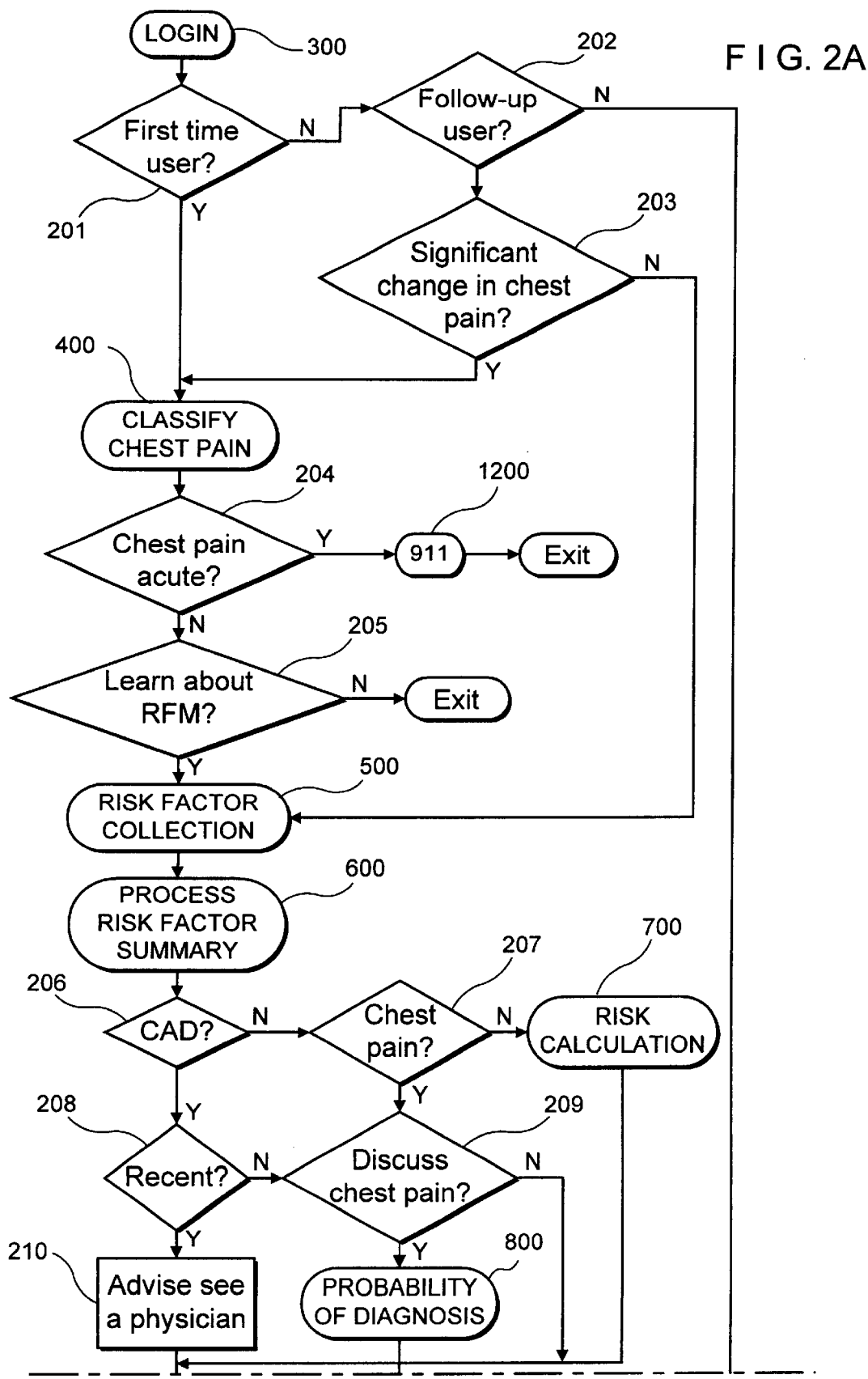
FIG. 2 illustrates a flow chart for a program for executing a method according to the present invention.
Figure 2B:
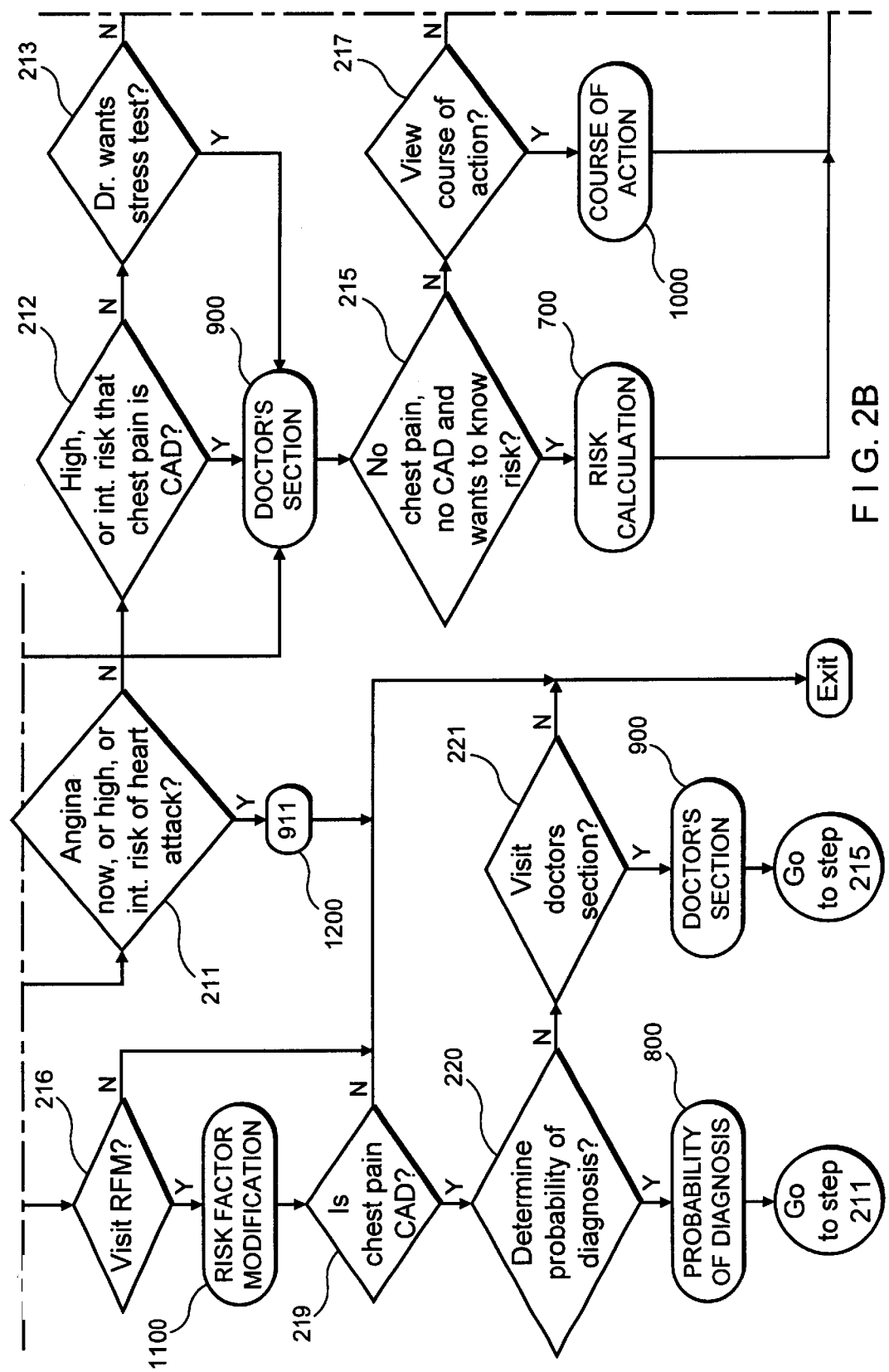

FIG. 2 illustrates a flow chart of a program for executing a method according to the present invention. In the example embodiment, the program determines the risk of developing CAD and ways to modify the risk of developing CAD. It should be noted that this program may be implemented for any disease for which there are known risk factors and practice guidelines. Once the program is accessed via the Internet, e.g., by a user using a browser, a login section, which is described in detail below (FIG. 3), is executed (step 300). The login section determines whether a user is a first time user, a registered follow-up user, or a doctor whose patient is a user that completed a probability of diagnosis section 800. If the user is a first time user (step 201), a preliminary assessment of chest pain section 400, which is described in detail below (FIG. 4), is executed. If the user is a registered follow-up user (step 202), the follow-up user is queried whether there has been a significant change in his or her symptoms since the last time the user accessed the program (step 203). If there has been a significant change in the follow-up user's symptoms, then the preliminary assessment of chest pain section 400 (FIG. 4) is executed. If there has not been a significant change in the follow-up user's symptoms, then the risk factor collection section 500 (FIGS. 5A–5E), which is described in detail below, is executed. If the user is a doctor whose patient has completed probability of diagnosis section 800 (FIG. 8), then doctor's section 900, which is described in detail below (FIG. 9), is executed.

Preliminary assessment of chest pain section 400, described in detail below (FIG. 4), assesses a user's experience with chest pain. If preliminary assessment of chest pain section 400 determines that an existing chest pain is acute (step 204), then 911 section 1200, which is described in detail below, is executed (see FIG. 3). If preliminary assessment of chest pain section 400 determines that there is no chest pain or the chest pain is not acute, and the user wants to learn about risk factor modification (RFM) (step 205), then risk factor collection section 500, which is described in detail below (FIG. 5), is executed. If the user does not want to learn about RFM, the user is invited to return and the program is ended.

Risk factor collection section 500 collects information on the user's physical characteristics, lifestyle and medical history. After risk factor collection section 500 is performed, risk factor summary section 600 is executed. The risk factor summary section 600 provides the user with a personal list of risk factors for developing CAD. If it is determined in risk factor collection section 500 that the user had recent coronary artery disease (CAD) (steps 206, 208), then the user is advised to see a physician (step 210) and queried if the user would like to learn about RFM (step 216). If the user wants to learn about RFM (step 216), a RFM section 1100, which is described in detail below (FIG. 11), is executed. If the user does not want to learn about RFM, the program is exited and the user is invited to return.

If risk factor collection section 500 determines that the user does not suffer from CAD and chest pain (steps 206, 207), then the user's risk of developing CAD is calculated in section 700. If risk factor collection section 500 determines that the user had a CAD event that was not recent (step 206, 208) and the user would like to discuss the chest pain (step 209), then probability of diagnosis section 800, which is described in detail below (FIG. 8), is executed. If the user has had a CAD recent event (step 208) and does not want to discuss his chest pain (step 209, then step 216 is executed as discussed above.

Probability of diagnosis section 800 determines whether the user chest pain is, for example, noncardiac, atypical angina, or typical angina. Probability of diagnosis section 800 also determines whether the angina is stable and the risk that the chest pain will lead to a heart attack and/or is CAD. If probability of diagnosis section 800 determines that the user is experiencing angina now or has a high or intermediate risk of having a heart attack (step 211), then 911 section 1200 is executed. If probability of diagnosis section 800 determines that there is a high or intermediate risk that the angina is CAD (step 212), then doctor's section 900 is executed. If the doctored wants a stress test (step 213), then doctor's section 900 is executed. If the user has CAD, the program proceeds to step 216 and continues as described above. If the user does not have a high or intermediate risk of having a heart attack (step 211), a high or intermediate risk that the angina will develop into CAD (step 212), and CAD (step 213), then risk calculation section 700 is executed. After the user's risk of developing CAD is calculated, the program executes step 216 and continues as described above.

In the doctor's section 900 information about left ventricular ejection fraction, stress imaging test results, exercise tolerance tests, and pattern of the CAD. After doctor's section 900, the user may either calculate his or her risk of developing CAD(700), view his or her course of action 1000, determine his or her probability of diagnosis 800, view the RFM section 1100, or exit the program. If the user has no chest pain and wants to view his or her risk of developing CAD (step 215), then risk calculation section 700 is executed. After risk calculation section 700, the program proceeds to step 216 and the program continues as described above. If the user wants to view his or her course of action (step 217), then course of action section 1000 is executed. After course of action section 1000, the program proceeds to step 216 and the program continues as described above. If the user wants to determine his or her probability of diagnosis (step 218), then probability of diagnosis section 800 is executed. After probability of diagnosis section 800, the program proceeds to step 211 and the program continues as described above. If the user wants to view the RFM section (step 216), then RFM section 1100 is executed. If the user wants to exit (step 216), then the user is invited to return and the program is ended.

After RFM section 1100, if the user chest pain is not CAD (219), the user is invited to return and the program is exited. If the user has CAD that could be coronary (step 219), then the user is queried whether the user would like to determine the probability of diagnosis (step 220). If the user would like to determine the probability of diagnosis, then probability of diagnosis section 800 is executed followed by step 211. If the user does not want to determine the user's probability of diagnosis (step 220), then the user is queried whether he would like to visit the doctor's section 900. If the user would like to visit the doctor's section (step 221), then doctor's section 900 is executed followed by step 215). If the user does not want to visit the doctor's section, then the user is invited to return and the program is exited.

Login Section

Figure 3:
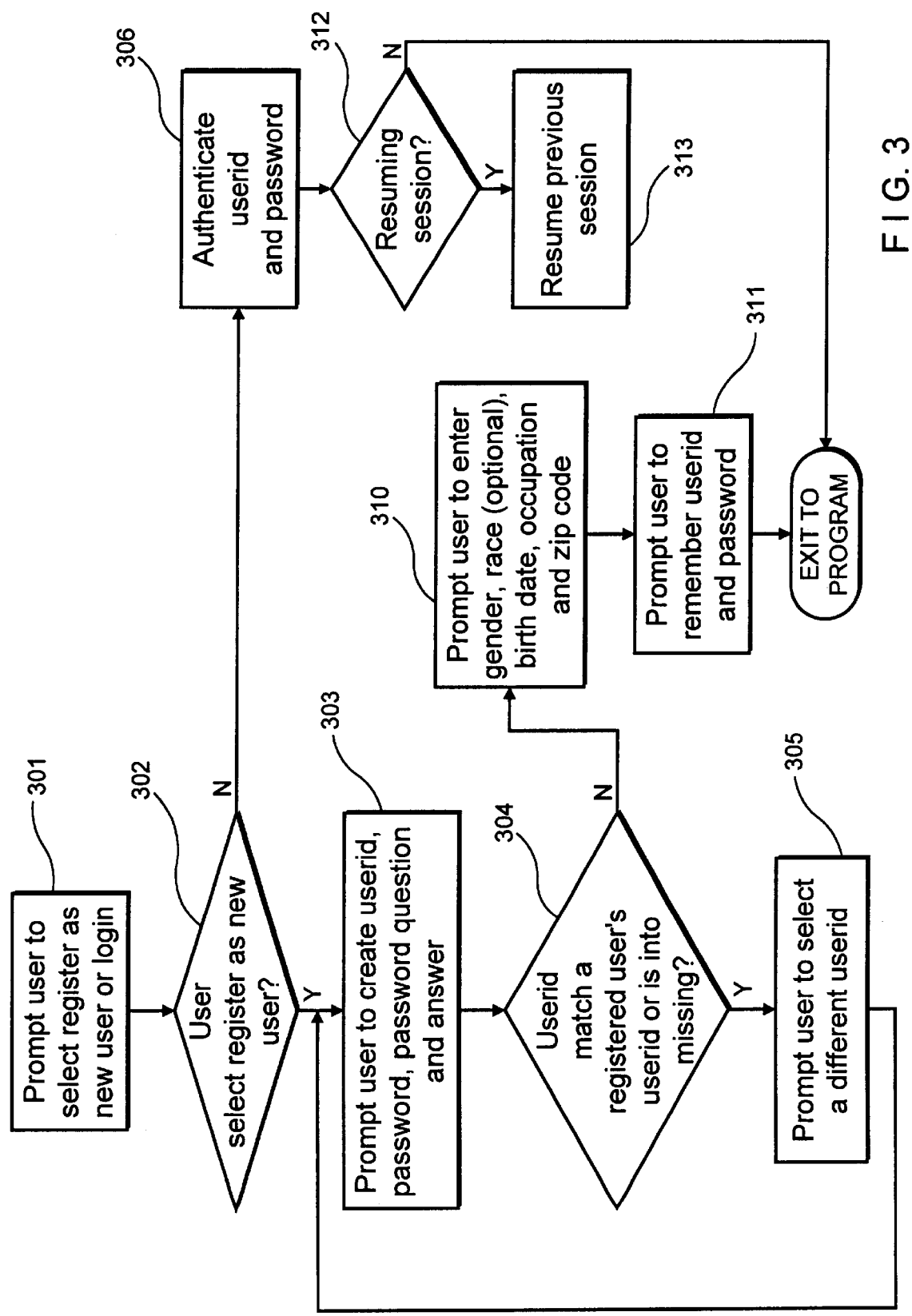
FIG. 3 illustrates a flow chart for the login section shown in FIG. 2.

FIG. 3 illustrates a flow chart for the login section shown in FIG. 2. The login section is executed when a user accesses the program. The user is instructed to either register as a new user or login (step 301). If the user is a follow-up user (step 302), for example, the user provides a userid and password, which are authenticated by the system (step 306). After step 306, if the follow-up user is resuming a session (step 312), then the program goes to the part of the program where the follow-up user exited the previous time (step 313). If the follow-up user is not resuming a session, then the login section is exited to the program as shown in FIG. 2.

If it is determined that the user is a first time user (step 302), then the new user is instructed to select a userid, password and password question and answer (step 303). The password question and answer are used when a user attempts to login but cannot remember his or her password. It is used to remind the user of his or her password. If the userid matches an existing userid or information is missing or invalid (step 304), then the new user is instructed to choose a different userid, supply missing information, and/or correct the invalid information (step 305). Once the new user has selected a userid that does not match an existing userid and/or provided valid information, then the new user is prompted to enter his or her gender, race (optionally), birth date, occupation and zip code (step 310). Next, the new user is instructed to remember his or her userid and password (step 311) and the login section is exited to the program.

Figure 3A:
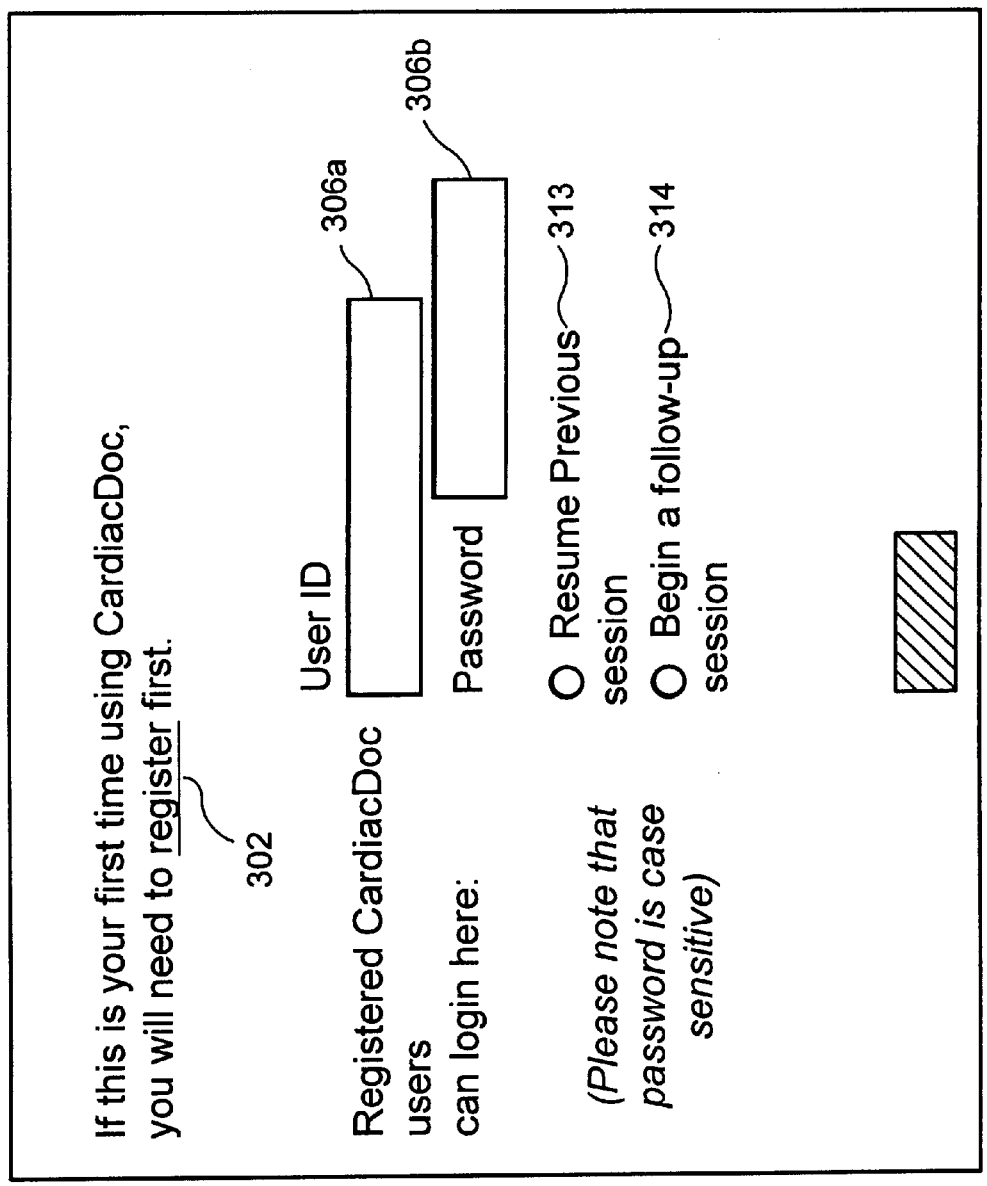
FIG. 3A illustrates an example embodiment of a screen display of the login section shown in FIG. 3.

FIG. 3A illustrates an example embodiment of a screen display for a portion of the login section. If the user is a first time user, the user is prompted to register first (302). Otherwise, the user is prompted to enter his or her userid (306a), password (306b), and either resume the previous session (313) or begin a follow-up session (314).

FIG. 3B illustrates an example embodiment of a screen display for an account registration portion of the login section. The first-time user is prompted to enter a userid and password (303a–b), confirm the password (303c), and enter a password question (303d). The first-time user is also prompted to enter his or her sex (310a), date of birth (310b), race (310c), occupation (310d), and zip code (310e).

Preliminary Assessment of Chest Pain Section

Figure 4:
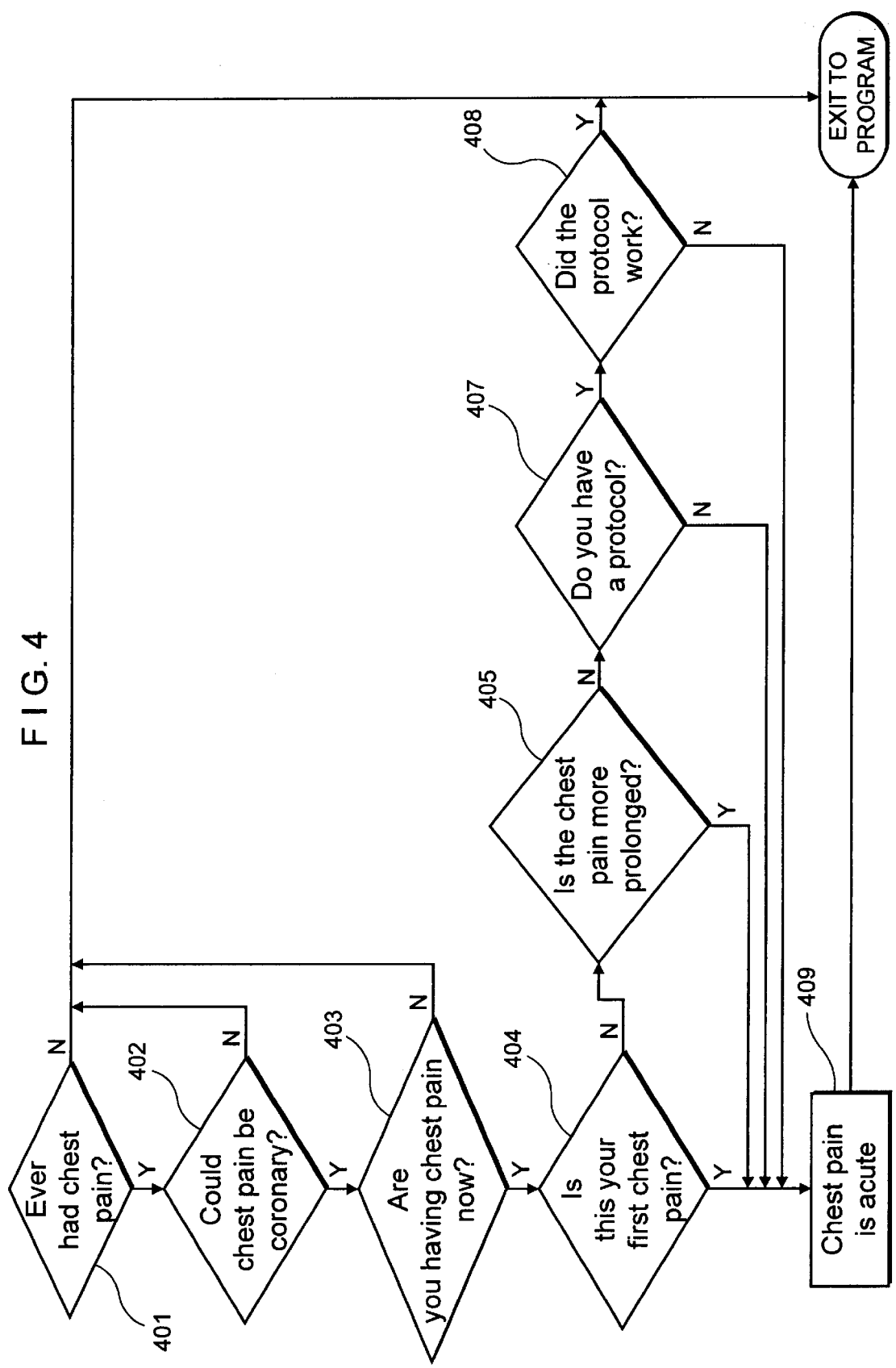
FIG. 4 illustrates a flow chart of the preliminary assessment of chest pain section shown in FIG. 2.

FIG. 4 illustrates a flow chart for the preliminary assessment of chest pain section shown in FIG. 2. The questions asked in the flow chart are just one example of the questions that may be asked to assess the user's chest pain. The user is queried if the user has ever had chest pain (step 401). If the user has had chest pain, the user is queried as to whether could be coronary (step 402). If so, the user is queried whether the user is experiencing chest pain now (step 403). If the user has never had chest pain (step 401), has had chest pain but it was not coronary (step 402), or has had coronary chest pain but not now (step 403), then the preliminary assessment of chest pain section is exited.

If the user is having chest pain now that could be coronary, then another series of question's are asked (step 404–408). If the chest pain is the user's first chest pain (step 404), then the chest pain is classified as acute (step 409) and the preliminary assessment of chest pain section is exited to the program. If the chest pain is not the user's first chest pain (step 404), but the chest pain is more prolonged than usual, then the preliminary assessment of chest pain section proceeds to step 409 as described above. If the chest pain is not the user's first chest pain (step 404), the chest pain is not more prolonged than usual (step 406), and the user does not have a protocol, then the preliminary assessment of chest pain section proceeds to step 409 as described above. If the chest pain is not the user's first chest pain (step 404), the chest pain is not more prolonged than usual (step 406), the user has a protocol that did not work (steps 407–408), then the preliminary assessment of chest pain section proceeds to step 409 as described above. If, however, the chest pain is not the user's first chest pain (step 404), the chest pain is not more prolonged than usual (step 406), the user has a protocol that worked (steps 407–408), then the preliminary assessment of chest pain section is exited to the program.

FIG. 4A illustrates an example embodiment of a screen display of a first portion of the preliminary assessment of chest pain section. FIG. 4A shows the user's response to the questions queried in steps 401–402 (whether the user has ever had coronary chest pain or CAD). FIG. 4A also shows step 205 querying the user whether the user would like to learn about RFM.

Figure 4B:
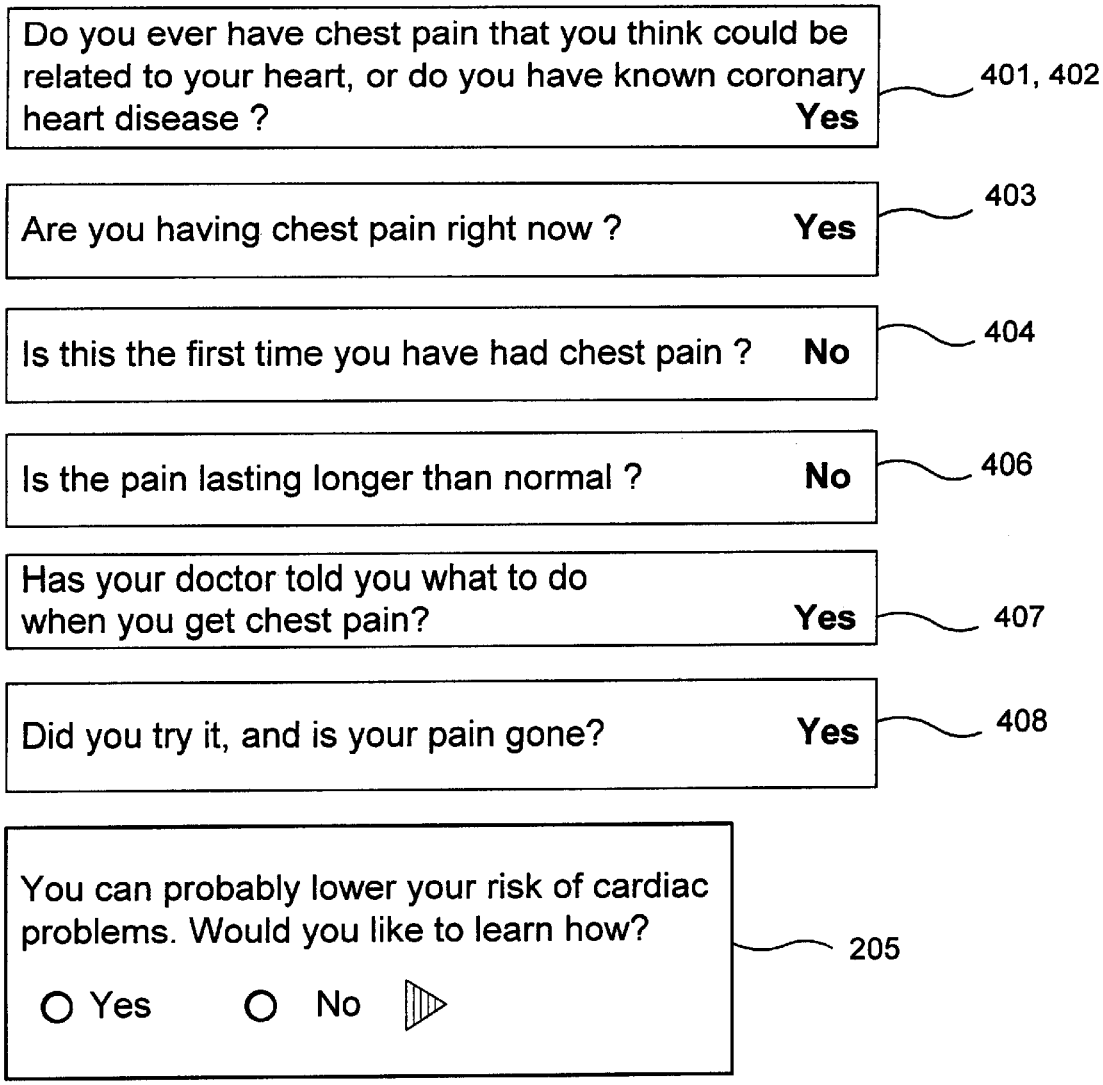
FIG. 4B illustrates a screen display of a second portion of the preliminary assessment of chest pain section.

FIG. 4B illustrates an example embodiment of a screen display of a second portion of the preliminary assessment of chest pain section. FIG. 4B shows the user's responses to the questions queried in steps 401–404, 406–408. FIG. 4B also shows step 205 querying the user whether the user would like to learn about RFM.

Risk Factor Collection Section

The risk factor collection section collects and stores information, for example, about the user's physical characteristics, lifestyle and medical history. As the user inputs information, the user is advised if it is a positive risk factor. If the user is a follow-up user, the user may choose which information he or she wishes to modify. In particular, the user may choose to modify a physical characteristics section, a lifestyle information section, etc., as described below. If, however, the user is a first time user, the user is prompted to enter information for each of the sections.

Figure 5A:
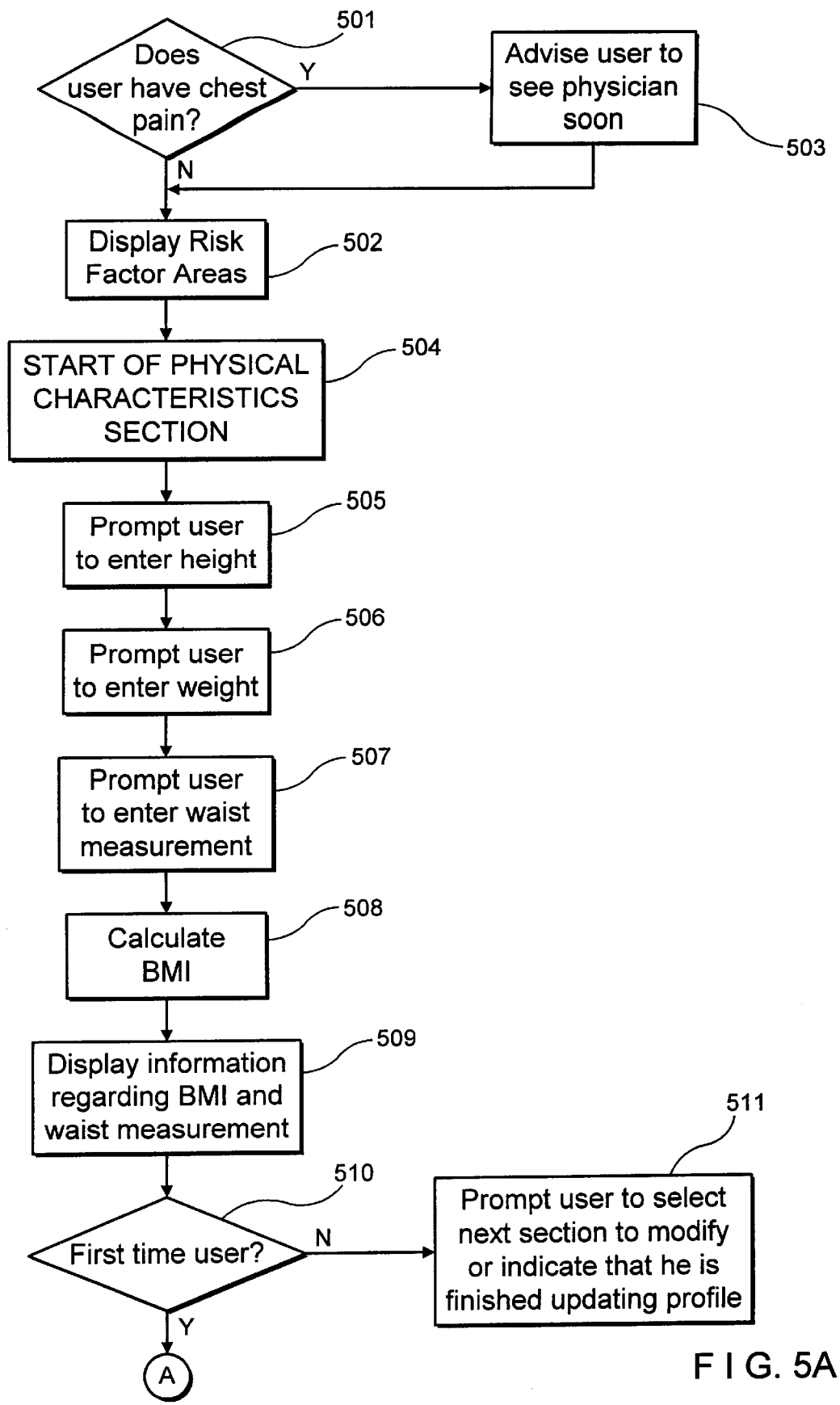
FIG. 5A illustrates a first section of a flow chart for the risk factor collection section shown in FIG. 2.

In FIG. 5A, the physical characteristics of the user are collected and stored in, for example, a physical characteristics database. These physical characteristics include, for example, height, weight, waist size, etc.

Initially, the user is asked if the user ever has chest pain (step 501). If the user has chest pain, then the user is advised that the user needs to see a doctor soon (step 503) and step 502 is executed. If the user does not have chest pain, then step 502 is executed.

In step 502, a list of general risk factor areas, for example physical characteristics, lifestyle, and medical history is displayed. The physical characteristics section is then started (step 504) and the user is prompted to enter his or her height (step 505), weight (step 506) and waist measurement (step 507).

A body mass index (BMI) is then calculated using the information provided by the user (step 508). The BMI is determined by dividing the weight (kg) by the height (m) squared. If the weight is in pounds and the height is in inches, then the BMI is multiplied by a factor of 704.5. Information regarding the user's BMI is displayed (step 509). This information includes, for example, whether the BMI is normal, overweight or obese. A normal BMI is, for example, 18.5–24.9. A BMI of 25–29.9 may indicate that the user is overweight. A BMI of, for example, 30–34.9 may, for example, indicate that the user is level one obese. A BMI from 35–35.9 indicates that the user is level two obese. A BMI greater than, for example, 40 indicates that the user is level three obese. In addition, a user whose BMI indicates that the user is obese is advised that the user's risk of developing CAD is augmented if the user's waist measurement is greater than, for example, 40 in. or 102 c.m, for a male, or the user's waist measurement is greater than, for example, 35 in. or 88 cm, for a female.

Figure 5B:
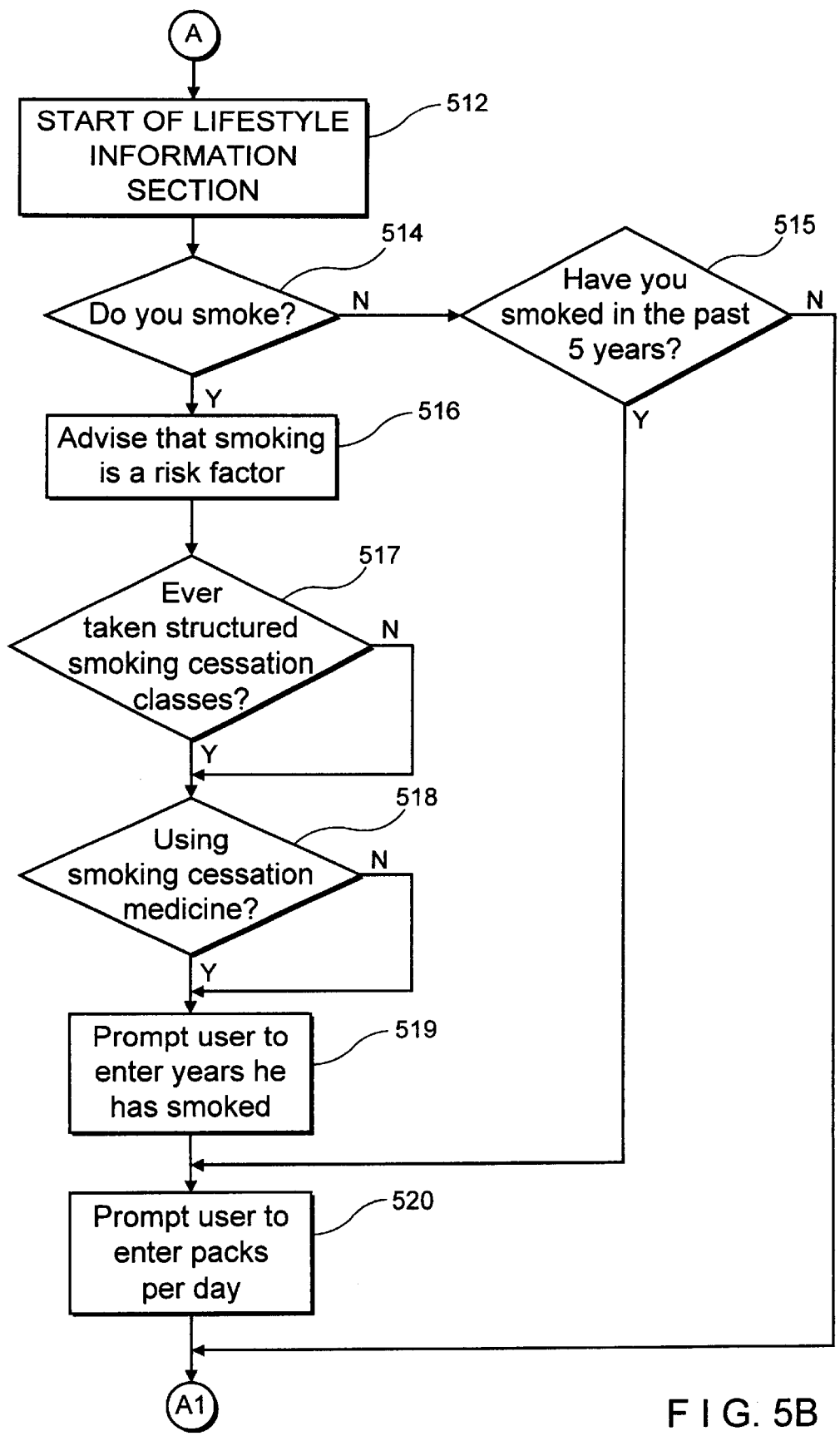
FIG. 5B illustrates a second section of a flow chart for the risk factor collection section shown in FIG. 2.

If the user is a first time user, then the lifestyle information is started (step 512 of FIG. 5B). If the user is a follow-up user, the user is queried to select another section to update or indicate that the user is finished updating (step 511).

The user's lifestyle information is collected and stored, for example, in a lifestyle information database. Note that a follow-up user proceeds to this section only if the user selects to update his or her lifestyle information. Referring to FIG. 5B, the user is queried whether the user currently smokes (step 514). If the user does smoke, the user is advised that smoking is a risk factor for CAD (step 516) and asked a series of questions regarding his or her smoking (steps 517–520). The smoking user is queried whether the user has ever taken a structured smoking cessation class (step 517). Next, the smoking user is queried whether the user is using smoking cessation medicine (step 518). The smoking user is prompted to enter the number of years the user has smoked (step 519). Finally, the smoking user is also prompted to enter the number of packs of cigarettes the user smokes per day (step 520).

If the user is not a smoker, the user is queried if the user has smoked in the past 5 years (step 515). If the user has smoked in the past 5 years, then step 520 is executed as described above. If the user has not smoked in the past 5 years, then step 521 is executed.

In step 521, the user is queried whether the user consumes alcoholic beverages. If the user does consume alcoholic beverages, then the user is prompted to enter the number of beers (step 523), glasses of wine (step 524), and/or glasses of spirits (step 525) the user consumes per day. If the user does not consume alcoholic beverages, the user is advised that it has be shown that modest consumption of alcoholic beverages has been shown to be linked to a decreased chance of developing CAD (step 522).

Next, the user is queried whether the user consumes antioxidant vitamins, such as vitamin E, C or beta carotene (step 526). If the user does not consume antioxidant vitamins, the user is advised that antioxidant vitamins may decrease a person's risk of developing CAD (step 527). The user is then queried whether the user gets his or her recommended daily allowance (RDA) of folate, vitamin B6, and vitamin B12 (step 528). If the user does not get the RDA of these vitamins, the user is advised that there is link between a decreased risk of developing CAD and these vitamins (step 529). The user is queried whether the user consumes an aspirin a day (step 530). If the user does not consume an aspirin a day, the user is advised of the benefits of taking an aspirin a day (531).

Next, the user is prompted to enter his or her level of exercise (step 532). The level of exercise is, for example, none, low, medium, or active. The user is then queried whether the user has entered a formal exercise program (step 533) and whether the user follows American Heart Association guidelines (step 534).

Next, the user is prompted to enter his or her current level of stress, depression or hostility (step 535). The level of stress is, for example, none, low, moderate or severe. Then, the user is queried whether the user has entered a formal stress reduction program (step 536).

The user is then queried if the user is on a weight loss diet (step 538) and taking weight loss medication (step 539). If the user is a first time user, the medical history section is implemented. If the user is a follow-up user, the user is prompted to select another section to update or indicate that the user is finished updating (step 540).

Figure 5C:
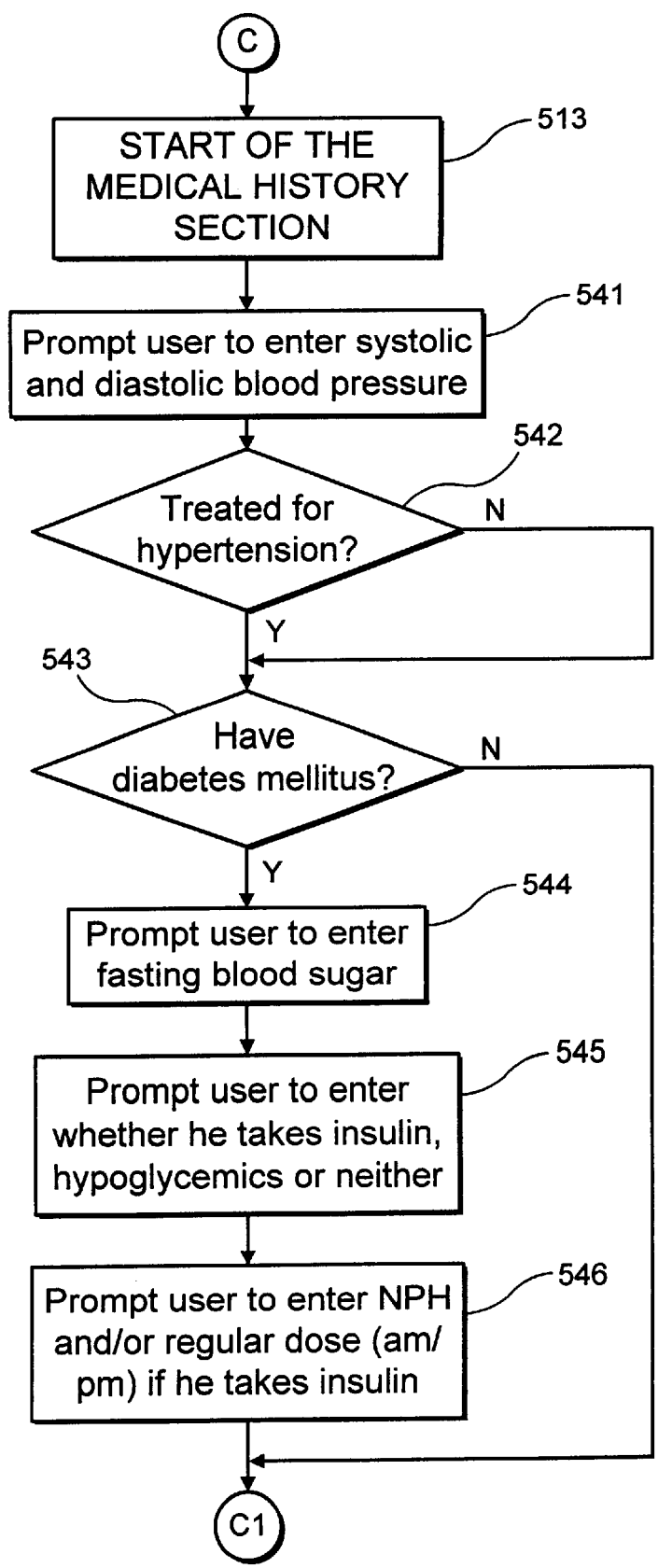
FIG. 5C illustrates a third section of a flow chart for the risk factor collection section shown in FIG. 2.

Next, the user's medical history is collected and stored, for example, in a medical history database. Referring to FIG. 5C, the user is prompted to enter his or her systolic and diastolic blood pressure and is advised whether his or her blood pressure is a risk factor (step 541). The user is also queried whether the user is being treated for hypertension (step 542). Next, the user is queried whether the user has diabetes mellitus (step 543). If the user has diabetes, then the user is prompted to enter, if known, his or her blood fasting sugar (step 544). Next the diabetic user is queried whether the user is taking insulin, hypoglycemics or neither insulin nor hypoglycemics (step 545). If the diabetic user is taking insulin the user is prompted to enter his or her NPH and/or regular dose (a.m. and p.m.) (Step 546).

Steps 547–551 are performed only for female users. The female user is queried whether she has finished menopause (step 548). The female user is also queried whether her ovaries have been removed (steps 549–550). If the female user has finished menopause and/or had her ovaries removed, then the user is queried whether she is receiving hormone replacement (step 551).

Figure 5D:
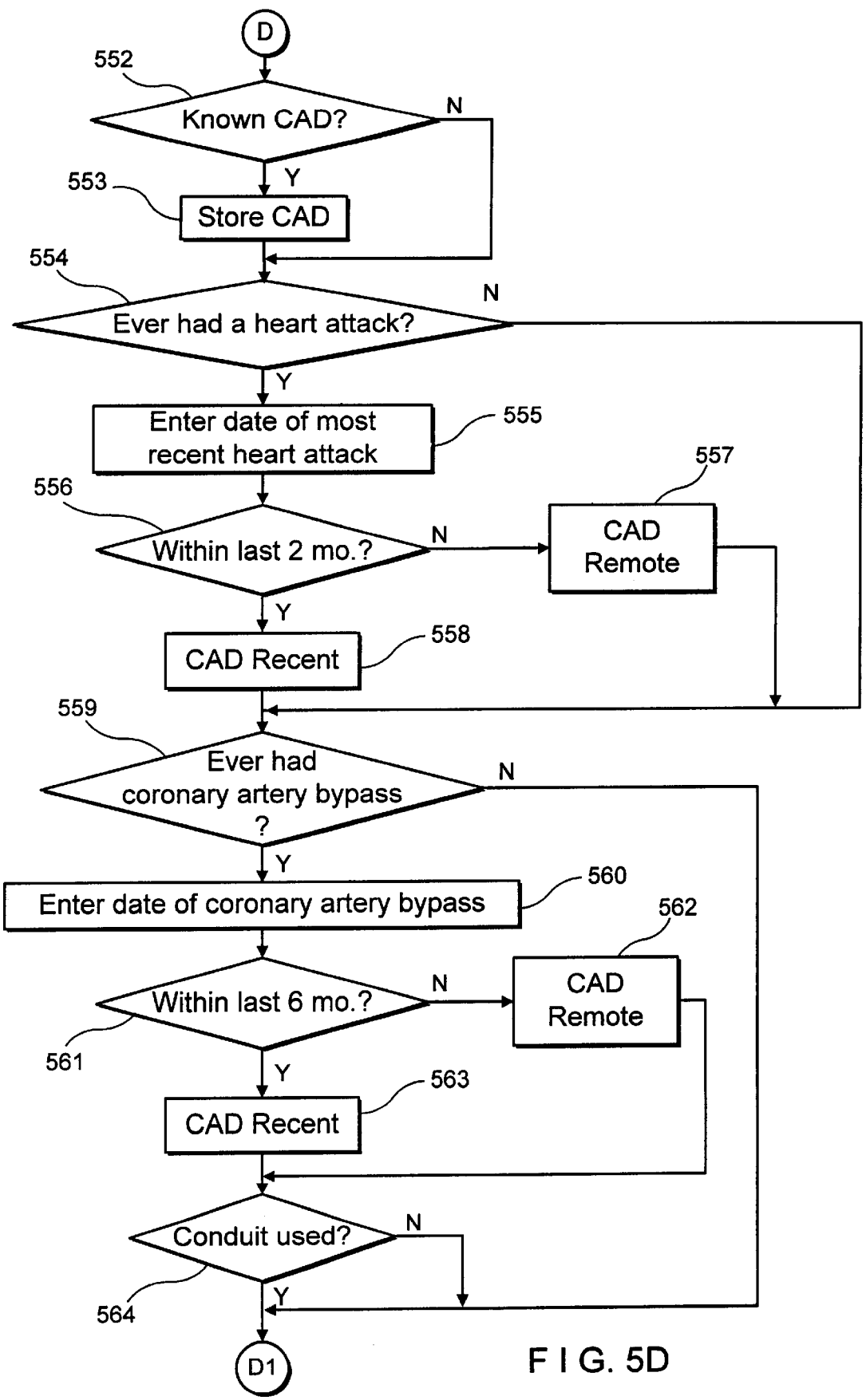
FIG. 5D illustrates a fourth section of a flow chart for the risk factor collection section shown in FIG. 2.

Referring to FIG. 5D, steps 552–570 determine whether a user has CAD. The user is queried whether the user has known CAD (step 552). If the user has known CAD, then it is stored that the user has CAD (step 553). Next, the user is queried whether the user has ever had a heart attack (step 554). If the user has had a heart attack, then in the user is prompted to enter the date of the most recent heart attack occurred (step 555). If the heart attack occurred within the last 2 months, then the heart attack is stored as a CAD recent event (step 558). If the heart attack did not occur within the last two months, then it is stored as a CAD remote event (step 557).

Next, the user is queried whether the user has ever had coronary artery bypass surgery (step 559). If the user has had coronary artery bypass surgery, then the user is prompted to enter the date that the user had the surgery (step 560). If the surgery took place within the last six months, then it is identified as a "CAD recent event" (step 563). If the coronary artery bypass surgery did not take place within the last six months, then the surgery is identified as a "CAD remote event" (step 562). Finally, if the user that has had coronary artery bypass surgery, then the user is queried which type of conduit, such as left internal mammary artery, right internal mammary artery, vein graft, or radial artery, was used (step 564).

Next, the user is queried whether the user has had angioplasty (step 565). If the user has had angioplasty, then the user is prompted to enter the date of the angioplasty (step 566). If the user has had angioplasty within the last 2 months, then the angioplasty is stored as a CAD recent event (step 569). If the user did not have the angioplasty within the last 2 months, then the angioplasty is stored as a CAD remote event (step 568). Finally, a user who has had angioplasty is queried whether a stent was used (step 570).

Figure 5E:
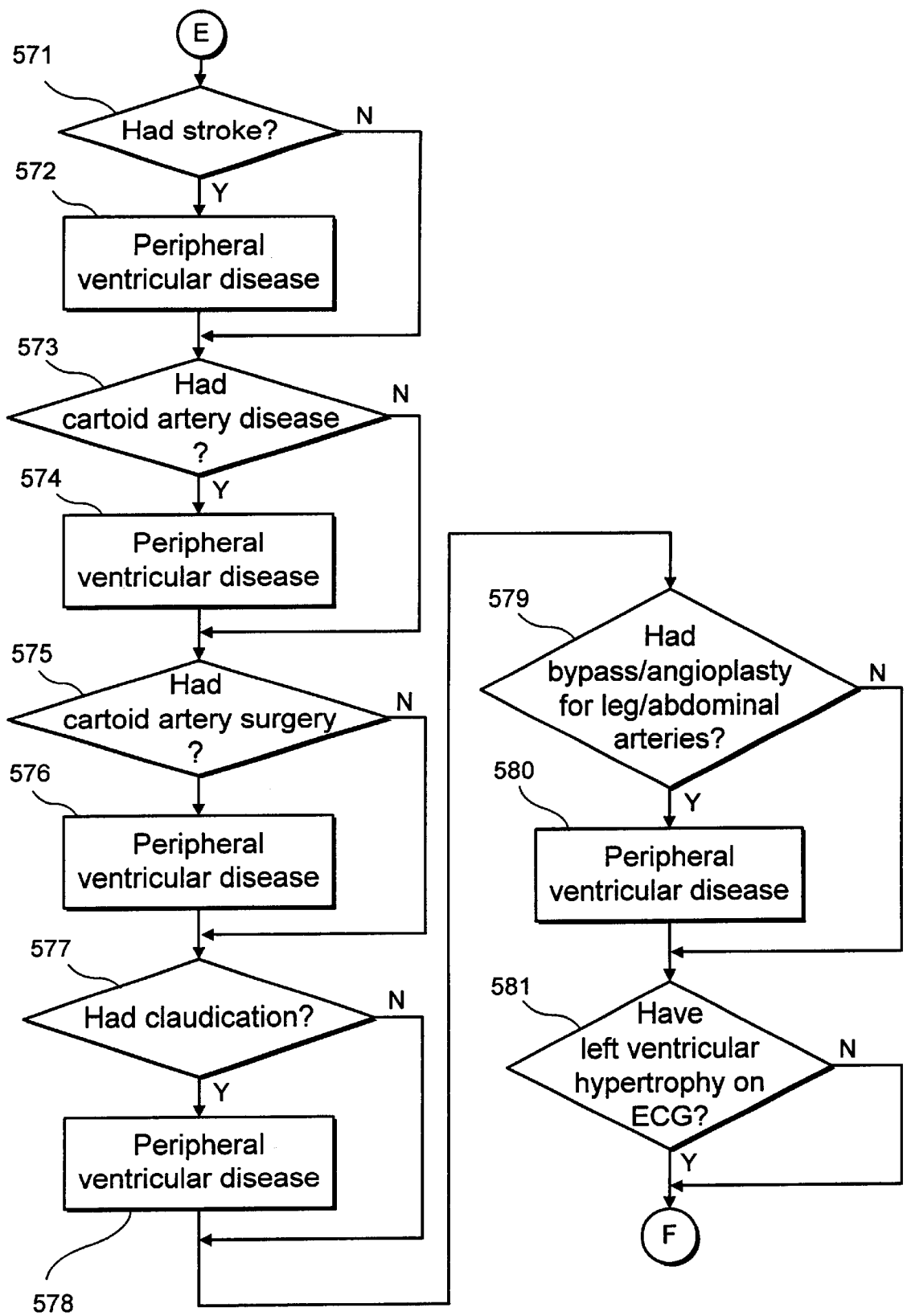
FIG. 5E illustrates a fifth section of a flow chart for the risk factor collection section shown in FIG. 2.
Figure 51:

Referring now to FIG. 5E, the user is queried regarding peripheral vascular disease in steps 571–580. First, the user is queried whether the user has ever had a stroke (step 571), cartoid artery disease (step 573), cartoid artery surgery (step 575), claudication (step 577), or bypass or angioplasty on his or her leg or abdominal arteries (step 579). If the user has had any of these conditions or procedures, it is recorded as peripheral vascular disease (steps 572, 574, 576, 578, 580). Next, the user is queried whether the user has left ventricular hypertophy on his or her electrocardiogram ("ECG") (step 581). Then, the user is prompted to enter his or her homocysteine level and lipoprotein level, if known (steps 582–583). Based on these levels, the user is advised whether these levels are risk factors.

In steps 584–585, the user is queried regarding his or her family history. First, the user is queried whether the user has a family history of premature coronary artery disease (step 584). Next, the user is queried whether family members have had heart attacks or died suddenly, and the age of those family members who have had heart attacks or died suddenly (step 585).

Next, the user is queried whether the user knows his or her lipid (cholesterol) profile (step 586). If the user knows his or her lipid profile, then the user is prompted to enter his or her total cholesterol, triglycerides, HDL and LDL (step 587). If the user is a first time user, then the risk factor collection section is exited to the program. Follow-up users are prompted to select another section to update or indicate that the user has finished updating his or her profile (step 589).

FIG. 5F shows an example embodiment of a screen display shown prior to the risk factor collection section shown in FIG. 2. The screen display explains that in order to determine the user's risk for CAD, the user must provide the program with information regarding the user's lifestyle, general health, and medical history.

FIG. 5G shows an example embodiment of a screen display for the collection of a user's physical characteristics. The user is prompted to enter his or her height in feet and inches (505a) or in centimeters (505b). The user is also prompted to enter his or her weight in either pounds or kilograms (506a). The user may calculate his or her BMI by clicking on the calculator (508).

FIG. 5H shows an example embodiment of a first screen display for the collection of a user's lifestyle information. The user's responses to the queries made in the preliminary assessment of chest pain section 400, the physical characteristics portion (steps 505–508) of the risk factor collection section 500, and step 514 are shown in FIG. 5H. Since, the user has responded yes to query 514 (whether the user smokes), the user is prompted to respond to a series of queries regarding the user's smoking habits (517–520).

FIG. 5I shows an example embodiment of a second screen display for the collection of a user's lifestyle information. The user's responses to the queries made in the lifestyle portion of the risk factor collection section 500, shown in FIG. 6C, are displayed. In this screen display, the user is prompted to respond to queries 526, 528 and 530 (vitamin and aspirin intake).

Process Risk Factor Summary

In process 600, based on the information the user provided during the collection of physical characteristics, lifestyle information, and medical history, a risk factor summary is generated. Positive risk factors are factors that indicate that a user may be at risk for a disease. Positive risk factors for CAD include, for example:

1. being a male;
2. being a female post menopausal or a female post menopausal with ovaries removed;
3. being a male over 40 years of age, being a female over 45 years of age;
4. having a BMI that indicates the user is overweight;
5. being a smoker;
6. having diabetes mellitus;
7. having elevated lipid levels;
8. having known CAD;
9. having known peripheral vascular disease;
10. not exercising;
11. having hypertension (high blood pressure);
12. having feelings of stress and anxiety;
13. having left ventricular hypertrophy (an enlarged heart);
14. not taking anti-oxidant vitamins;
15. having high homocysteine levels;
16. not getting the RDA of folate, vitamin B6 or vitamin B12;
17. having a high lipoprotein level;
18. having a low alcohol intake;
19. having a positive family history of coronary disease; and
20. not taking one aspirin per day.

FIG. 6A illustrates an example embodiment of a screen display of a personal risk factor summary. The first column lists the various risk factors. The risk factors may, for example, be divided and color coded by type. The types of risk factors include, for example, type A, B, C, and D. A type A risk factor is one for which intervention has been shown to reduce the incident of CAD. Type A risk factors include, for example, smoking, dyslipidemia, high blood pressure, left ventricular hypertrophy, and aspirin intake. A type B risk factor is one for which intervention has been shown to likely reduce the incident of CAD. Type B risk factors include for example, diabetes, dyslipidemia, obesity, physical exercise, and hormone replacement therapy. A type C risk factor is one for which intervention may reduce the incidence of CAD. Type C risk factors include, for example, anger and stress, dyslipdemia, lipoprotein levels, homocysteine levels, vitamin intake, and alcohol consumption. A type D risk factor is one which cannot be modified. Type D risk factors include, for example, age, family history, known coronary disease, and known vascular disease.

The second column states whether the user is at risk for the risk factor. Subsequent columns, provide the user's status during prior implementations of the program. For example, in FIG. 6, smoking is a current risk factor for the user (601), and also was a risk factor for the user a month ago (602). Currently, not taking an aspirin a day is not a risk factor for the user (603). A month ago, however, the user was at risk for not taking an aspirin a day (604).

FIG. 6B illustrates various advisor screens displayed when a user response indicates a positive risk factor or the user has selected a positive risk factor from the risk factor summary shown in FIG. 6. The positive risk factors illustrated are being a cigarette smoker (516), not consuming any alcoholic beverages (522), not taking anti-oxidant vitamins (527), not taking an aspirin each day (530), not exercising (532), having a moderate level of stress (535), being hypertensive (542) and having a high level of homocysteine (582). The advisor includes, for example, verbiage on how to modify the risk factor.

FIGS. 6C–6T illustrates screen displays of information about a particular risk factor. These screens are displayed when the user selects (clicks on) a risk factor displayed in the personal risk factor summary shown in FIG. 6A.

Risk Factor Calculation Section

As shown in FIG. 2 (i.e., process 700), after the user's positive risk factors are displayed, if the user had neither CAD nor chest pain, then his or her risk of developing CAD is determined. The user's risk of developing CAD is determined using, for example, a conventional method, such as, the Framingham method. The Framingham method is described in the paper entitled "Assessment of Cardiovascular Risk by Use of Multiple-RiskFactor Assessment Equations," published by the American Heart Association, Inc. and American College of Cardiology.

The Framingham method assigns risk points to various risk factors, for example, age, total cholesterol, HDL cholesterol, diabetes, and smoking. Based on the risk points the risk of an individual is determined based on information from the Framingham Heart Study.

Figure 7A:
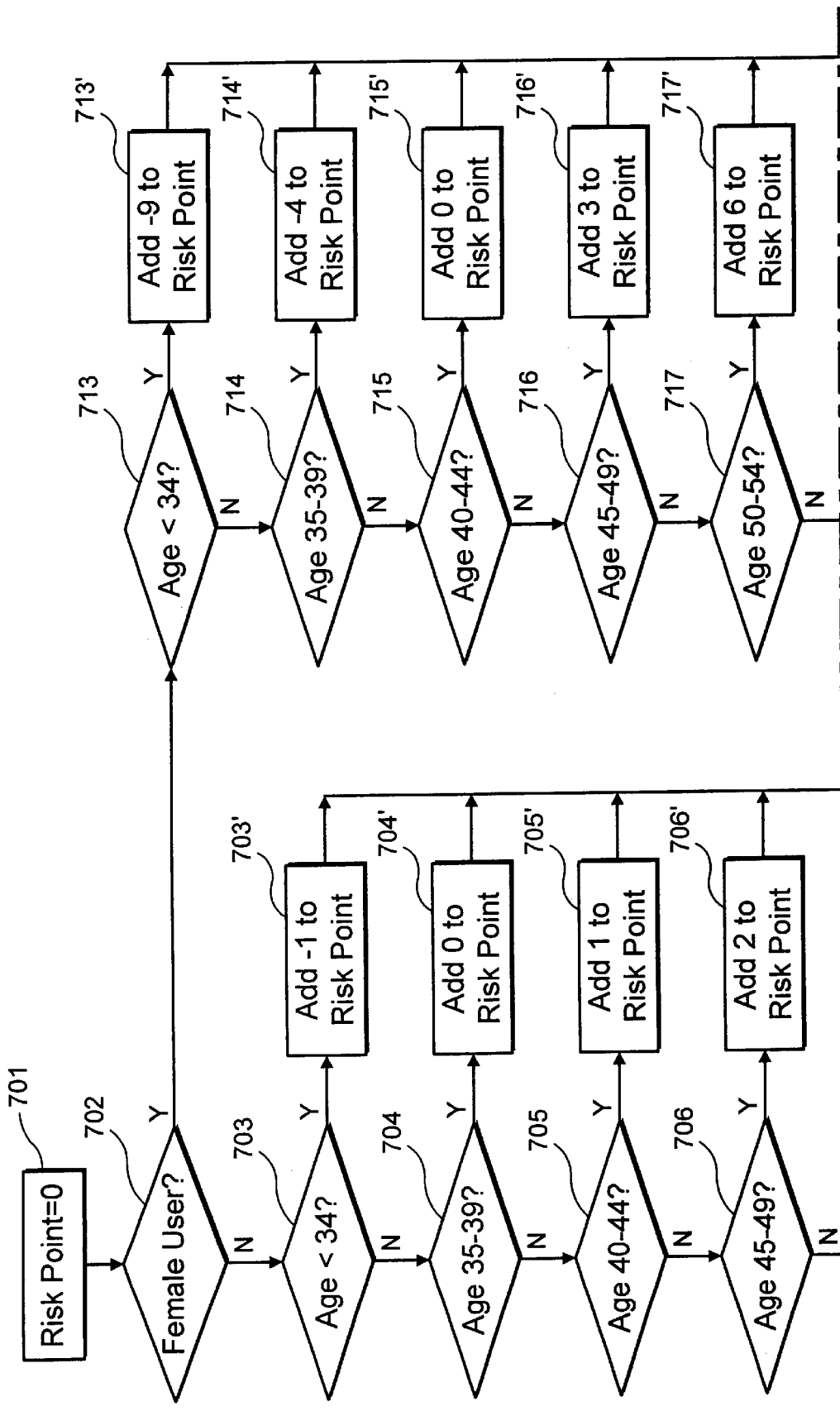
FIG. 7A illustrates a first section of a flowchart for the calculation of risk section shown in FIG. 2.

FIG. 7A illustrates a first section of a flowchart for the calculation of risk section shown in FIG. 2. First, the risk point total is set to zero (step 701). Next, based on the sex (step 702), and age (steps 703–711, 713–721), risk points are added to the risk point total (steps 703'–711', 713'–721'). For example, a male 41 six years old would have 1 point added to the risk point total (steps 705, 705').

Figure 7B:
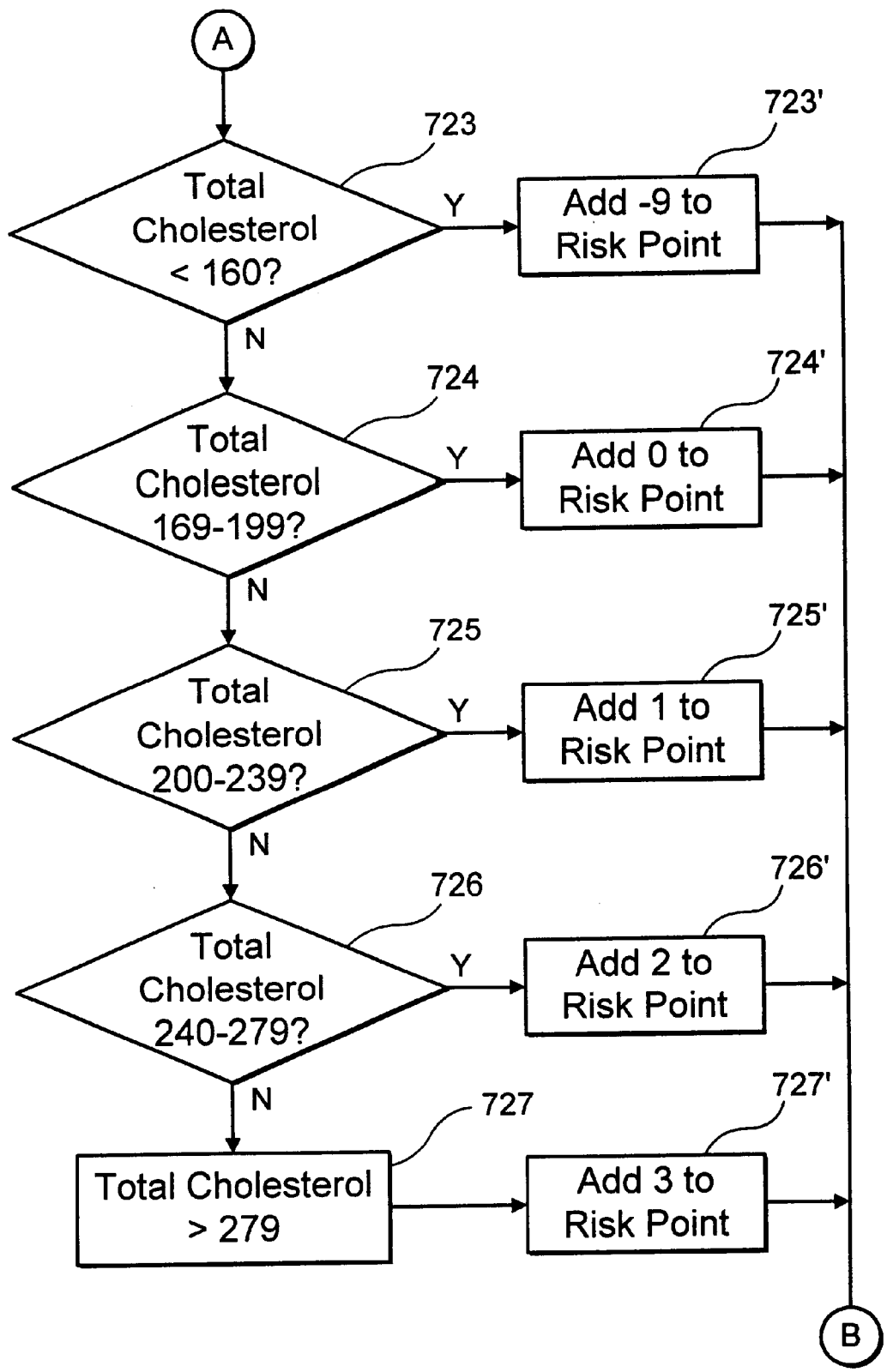
FIG. 7B illustrates a second section of a flowchart for the calculation of risk section shown in FIG. 2.

FIG. 7B illustrates a second section of a flowchart for the calculation of risk section shown in FIG. 2. After risk points are added based on age, risk points are added (steps 723'–727', 728'–732') to the risk point total based on the user's total cholesterol (steps 723–727, 728–732). For example, a male with a total cholesterol number of 245 would have 2 points added to his risk point total (steps 726, 726'). Thus, the 41 year old male with a total cholesterol of 245 would have a risk point total of 3 thus far.

Figure 7C:
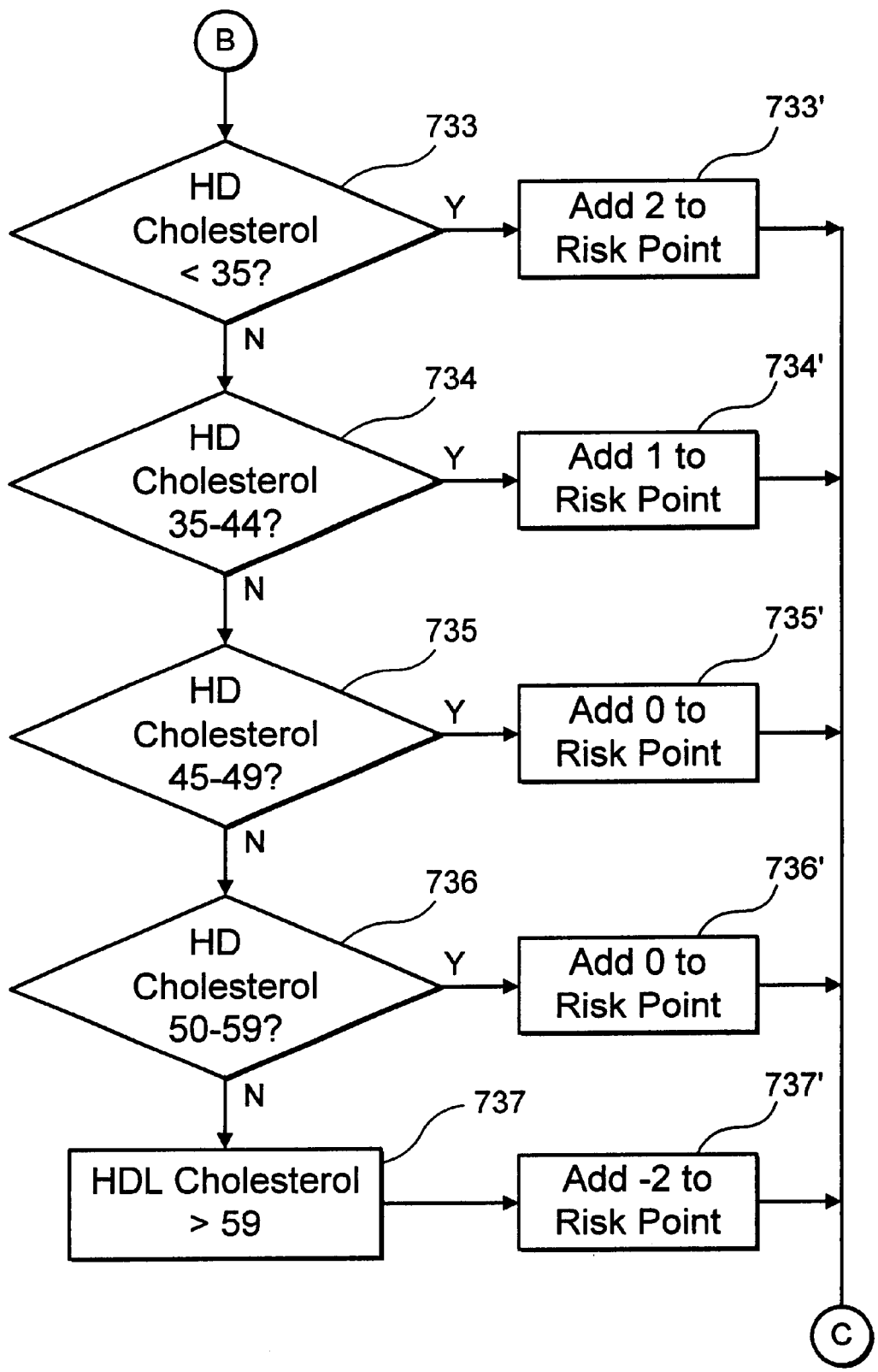
FIG. 7C illustrates a third section of a flowchart for the calculation of risk section shown in FIG. 2.

FIG. 7C illustrates a third section of a flowchart for the calculation of risk section shown in FIG. 2. After adding risk points based on total cholesterol number, risk points are added to the risk point total (steps 733'–737', 738'–742') based on HDL cholesterol (steps 733–737, 738–742). For example, a male with an HDL cholesterol number of 45 (step 735) would add 0 risk points to his risk point total (step 735'). Thus, the 41 year old male, with a total cholesterol of 245 and an HDL cholesterol number of 45 would have a risk point total of 3 thus far.

Figure 7D:
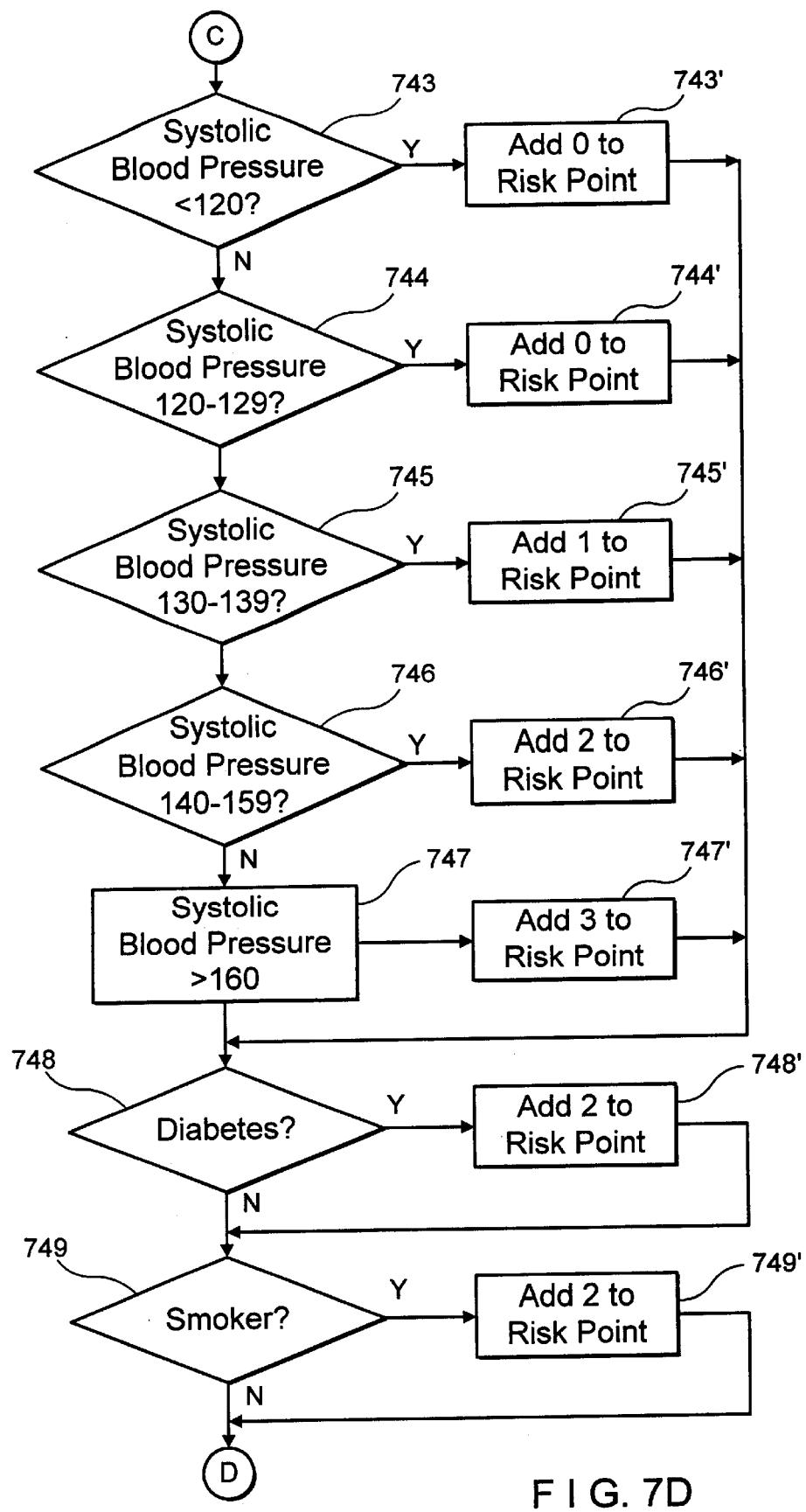
FIG. 7D illustrates a fourth section of a flowchart for the calculation of risk section shown in FIG. 2.

FIG. 7D illustrates a fourth section of a flowchart for the calculation of risk section shown in FIG. 2. In this portion of the flow chart, risk points are added based on the user's blood pressure (steps 743–747, 743'–747', 750–754, 750–754'), whether the user has diabetes (steps 748, 748', 755, 755'), and whether the user is a smoker (steps 749, 749', 756, 756'). For example a male user that has a blood pressure of 125 (step 744), has diabetes (step 748) and smokes (step 749) would add 4 points (steps 744', 748', 749'). Thus, a 41 year old smoking male with a total cholesterol of 245, an HDL cholesterol number of 45, a blood pressure of 125, and diabetes would have a risk point total of 7.

Figure 7E:
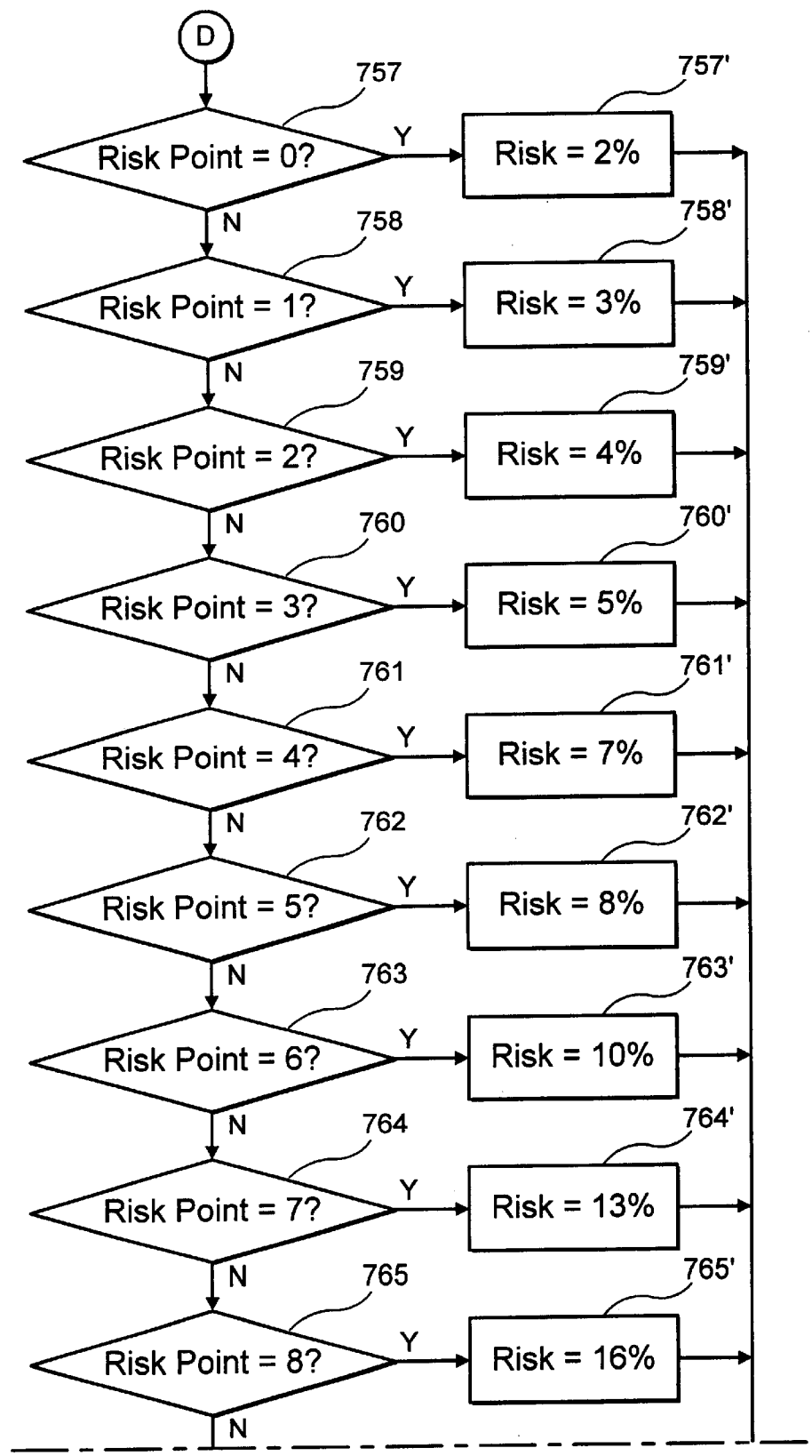
FIG. 7E illustrates a fifth section of a flowchart for the calculation of risk section, shown in FIG. 2, for a male.
Figure 7E:
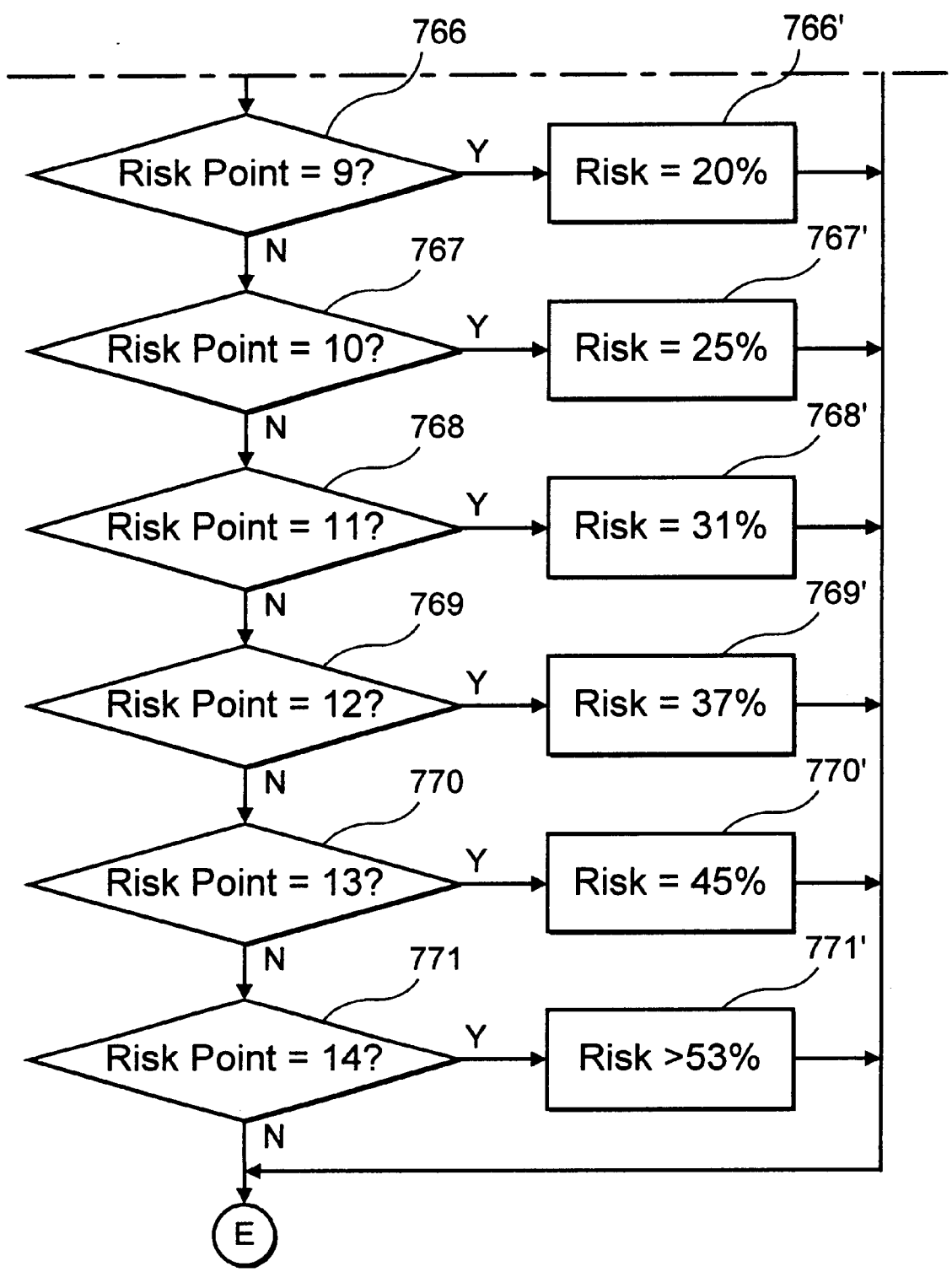

FIG. 7E illustrates a fifth section of a flowchart for the calculation of risk section, shown in FIG. 2, for a male user. After the risk point total is calculated, the user's risk is determined and compared with a low risk population. Referring to FIG. 7E, based on the risk point total (steps 757–771) calculated in FIGS. 7A–7D the risk is determined (steps 757'–771'). Using the previous example where the risk point total was 7 for a 41 year old male, his risk of developing CAD is 13% (steps 764, 764'). In steps 772–779 and 772'–779', this risk is compared with the low risk population. Thus, this user 13% risk is 4.3 times the risk of a low risk population of 41 year old males.

Figure 7F:
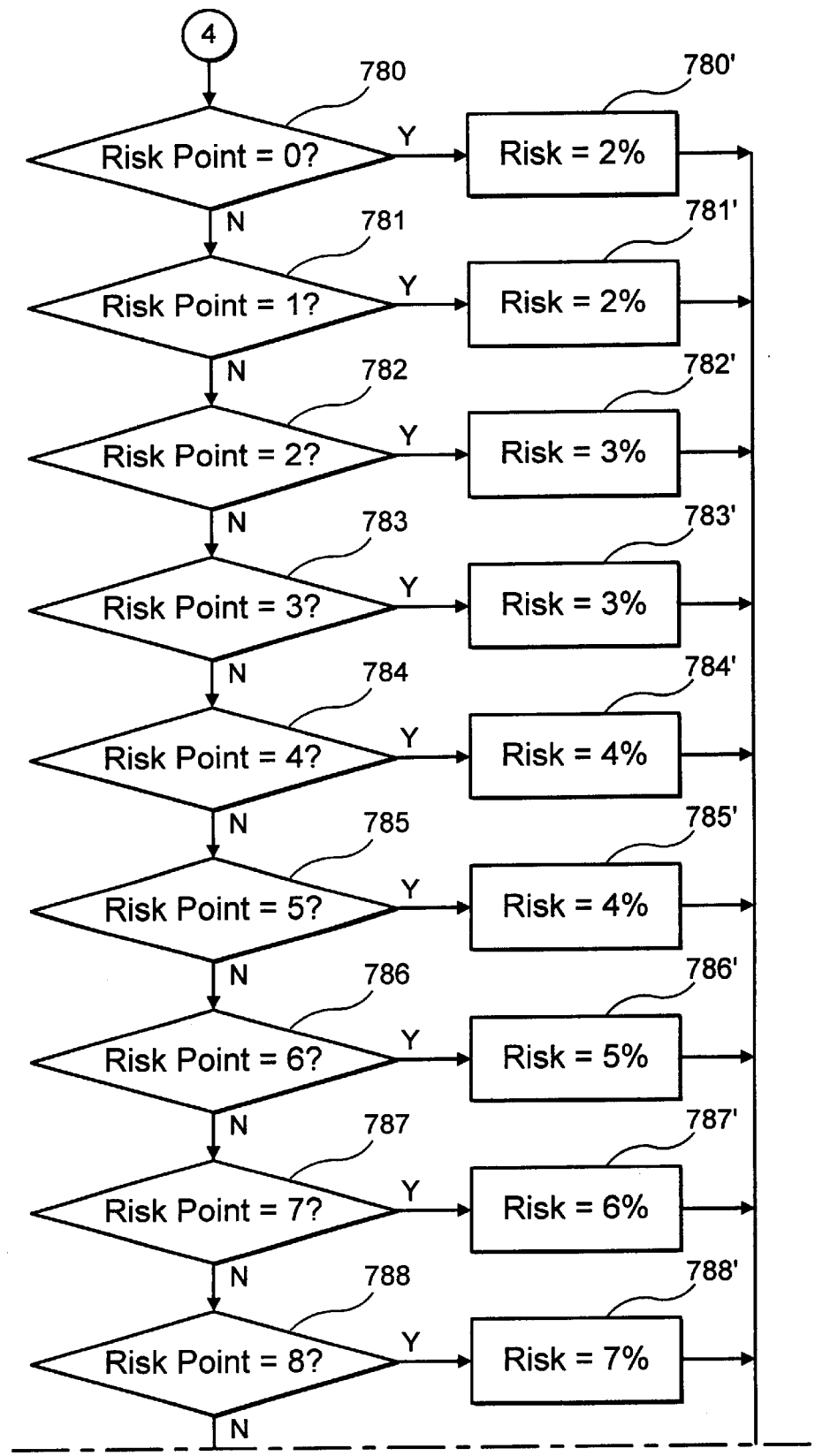
FIG. 7F illustrates a fifth section of a flowchart for the calculation of risk section, shown in FIG. 2, for a female.

FIG. 7F illustrates a fifth section of a flowchart for the calculation of risk section, shown in FIG. 2, for a female user. FIG. 7F determines the risk that a female will develop CAD (steps 780–797, 780'–797') and compares the risk with the low risk population (steps 701"–710"). For example, a 41 year old female user with a risk point total of 7 has a 6% chance of developing CAD (steps 787, 787'). This risk is 3 times the risk of a low risk population of 41 year old females (step 701", 706").

Probability of Diagnosis Section

Figure 8:
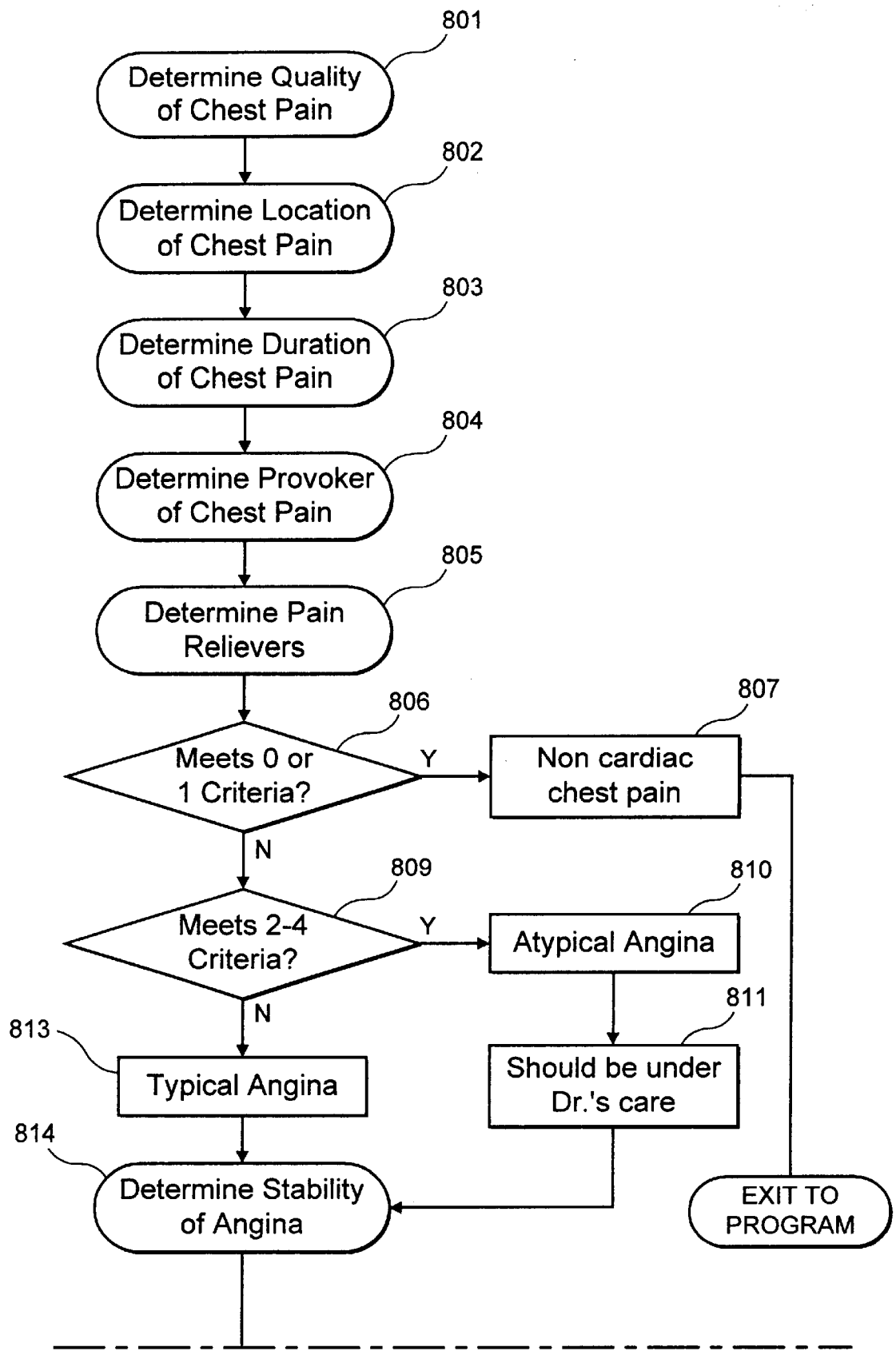
FIG. 8 illustrates a flow chart for the probability diagnosis section shown in FIG. 2.
Figure 8:
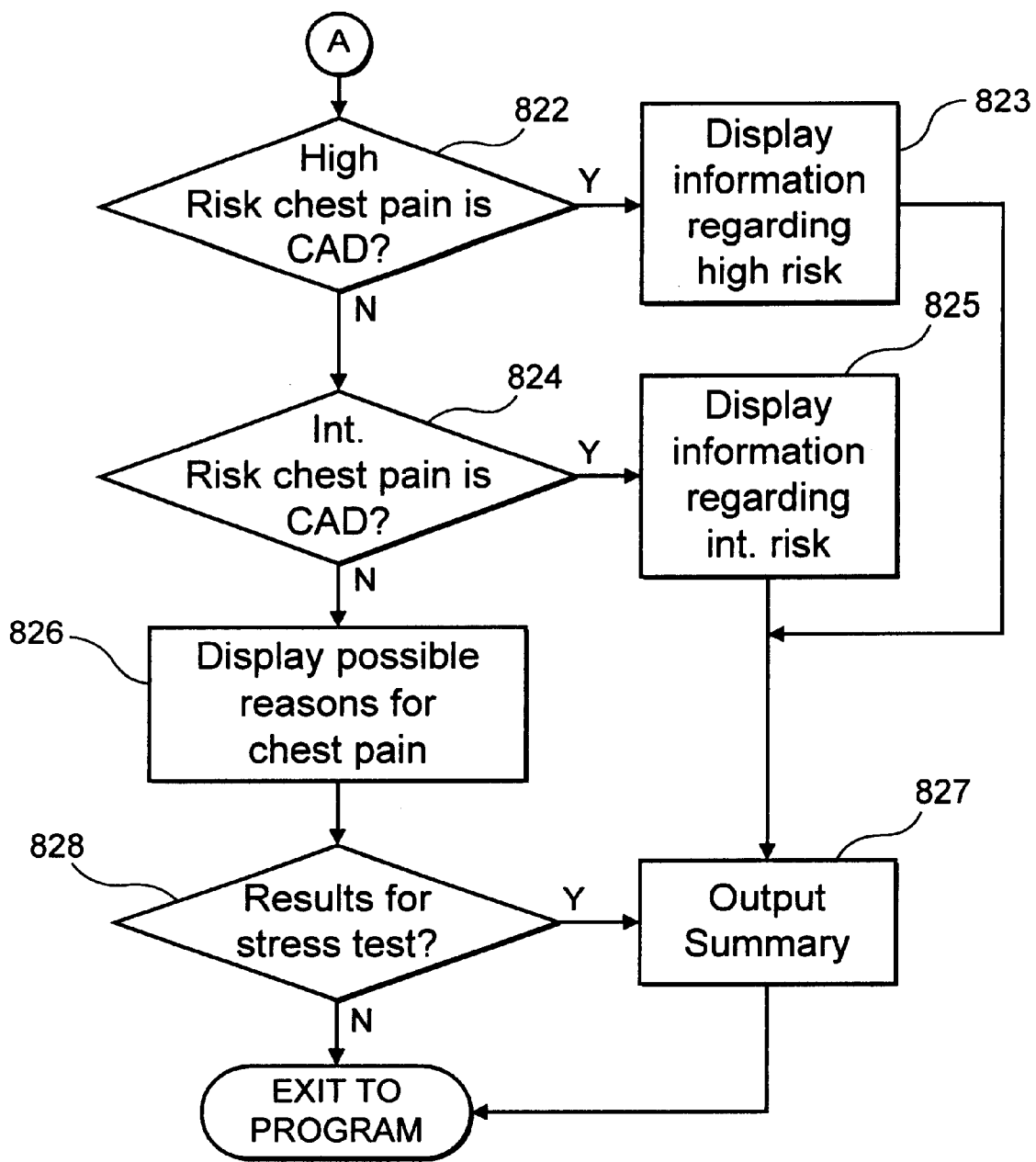

FIG. 8 illustrates a flow chart of a probability of diagnosis (process 800) section shown in FIG. 2. This section is executed when the user opts to discuss chest pain, and determines the likelihood that the user has CAD. Information provided by the user in this section may be stored, for example, in a probability of diagnosis database. In steps 801–805, the quality, location, duration, and instigators of, and pain relievers for the chest pain are determined. Each of these determinations may trigger one of five criteria. If one or none of the criteria is met, then the chest pain is classified as non-cardiac chest pain (step 807) and step 213 is executed. If two, three or four of the criteria are met (step 809), then the user's chest pain is classified as atypical angina (step 810) and the user is advised that the user should be under a physicians care (step 811). If the user's angina meets all five of the criteria, then the user's chest pain is classified as typical angina (step 813). If a user has atypical or typical angina, then the stability of the angina is determined (step 814). If it is determined that the user's angina is unstable and not low risk unstable angina, then the user's risk of having a heart attack is determined, as described below (step 816). If it is determined in step 816 that the user has a high or intermediate risk of having a heart attack (steps 817–818), then the probability of diagnosis section 800 is exited to the main program. If the user has stable angina, low risk unstable angina (step 815), or a low risk of having a heart attack (steps 817–818), then the risk that the chest pain is CAD is determined (step 819).

Next, using the fasting blood sugar, lipid levels, and left ventricular hypertophy information collected during the medical history collection, and using hemoglobin and resting ECG information collected in step 820, a more accurate risk that user's chest pain is CAD is determined for those users that have diabetes and hyperlipidemia (step 821).

If there is a high risk that the user's chest pain is CAD (step 822), then information regarding the options available to the user's physician is displayed (step 823). If there is an intermediate risk that the user's chest pain is CAD (step 824), then the need for further testing is explained to the user (step 825). In the case of either a high or an intermediate risk (step 822, 824), a summary of the information provided by the user is outputted (step 827) and the probability of diagnosis section 800 is exited to the main program.

If there is a low risk that the user's chest pain is CAD (step 822–824), then possible causes for the chest pain are displayed (step 826). If the user has the results from a stress test (step 827), then step 827 is executed as described above. If the user does not have the results from a stress test, then probability of diagnosis section 800 is exited to the main program.

Figure 8A:
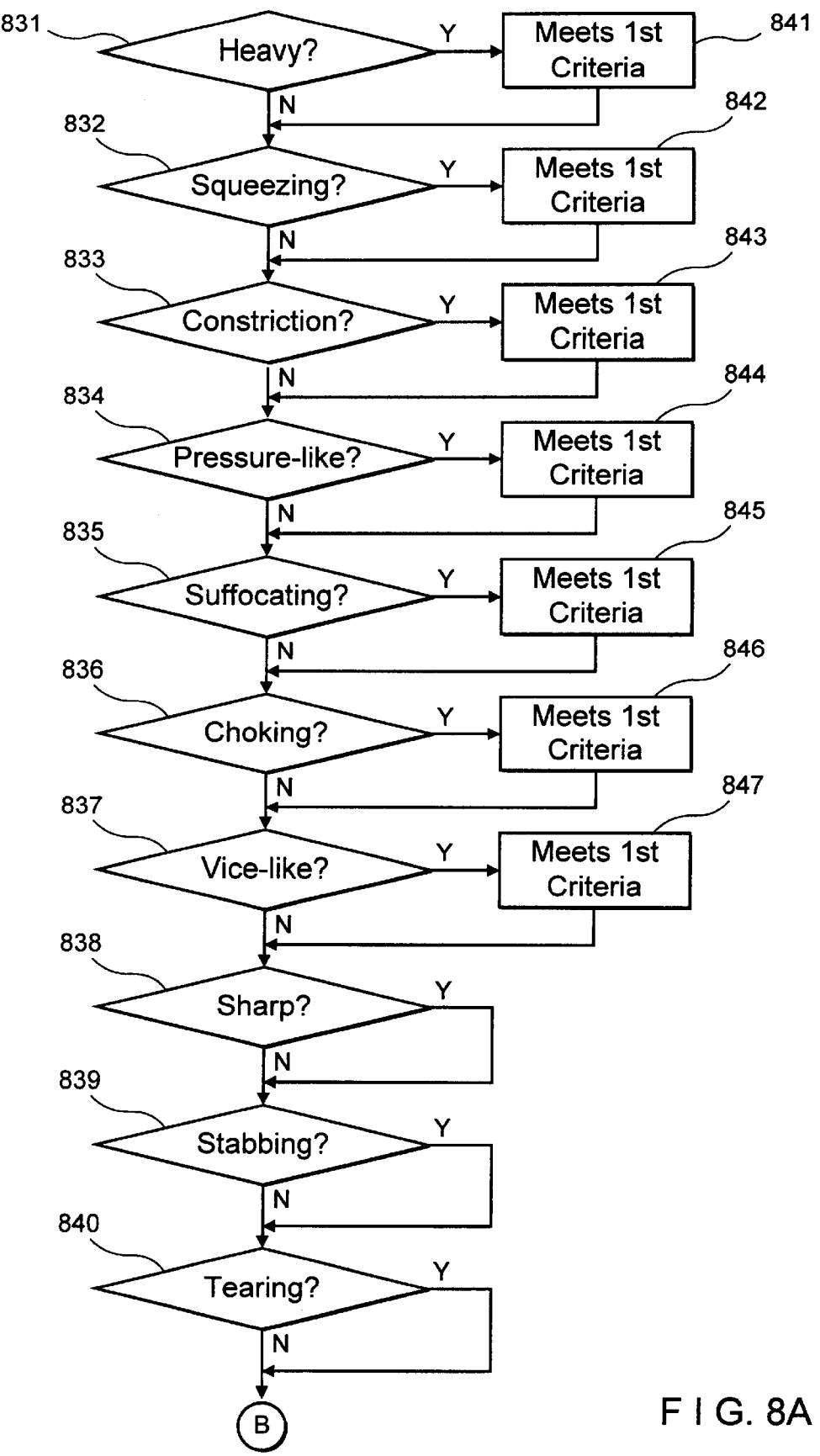
FIG. 8A illustrates a flow chart for determining the quality of a chest pain.

FIG. 8A illustrates a flow chart for determining the quality of a chest pain. The user is queried whether the chest pain is heavy, squeezing, constricting, pressure-like, suffocating, choking, vice-like, sharp, stabbing or tearing (steps 831–840). If the chest pain is heavy squeezing, constricting, pressure-like, suffocating, choking and/or vice-like, then the first of the five criteria has been met (steps 841–847).

Figure 8B:
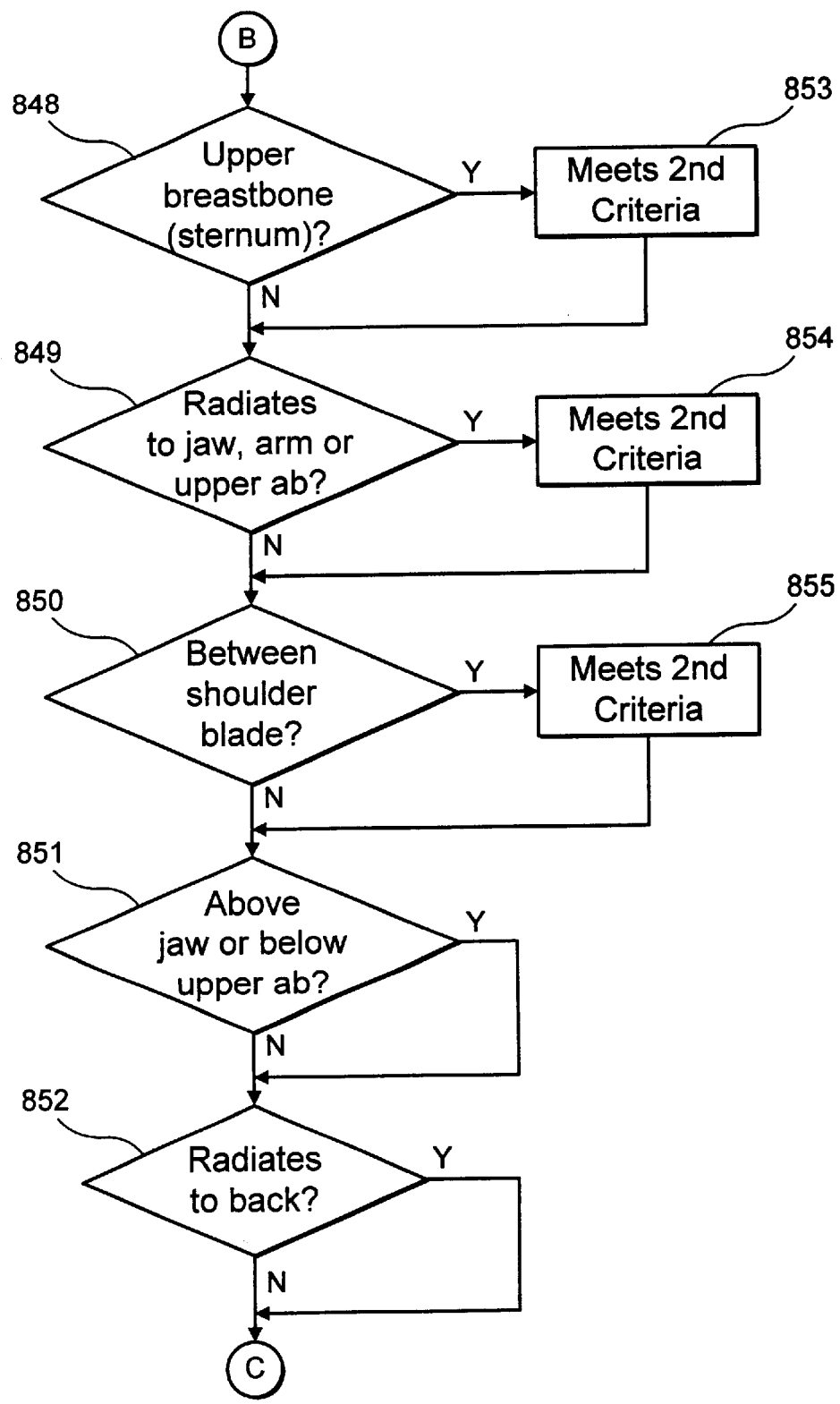
FIG. 8B illustrates a flow chart for determining the location of a chest pain.

FIG. 8B illustrates a flow chart for determining the location of a chest pain. The user is queried whether the chest pain is:

1. Located in the upper breast bone (sternum) (step 848).
2. Radiating to the jaw, or upper abdomen (step 849).
3. Located between the shoulder blades (step 850).
4. Located above the jaw or below the upper abdomen (step 851).
5. Radiating to the back (step 852).

If 1, 2, and/or 3 is true, then the second of the five criteria has been met (steps 853–855).

Figure 8C:
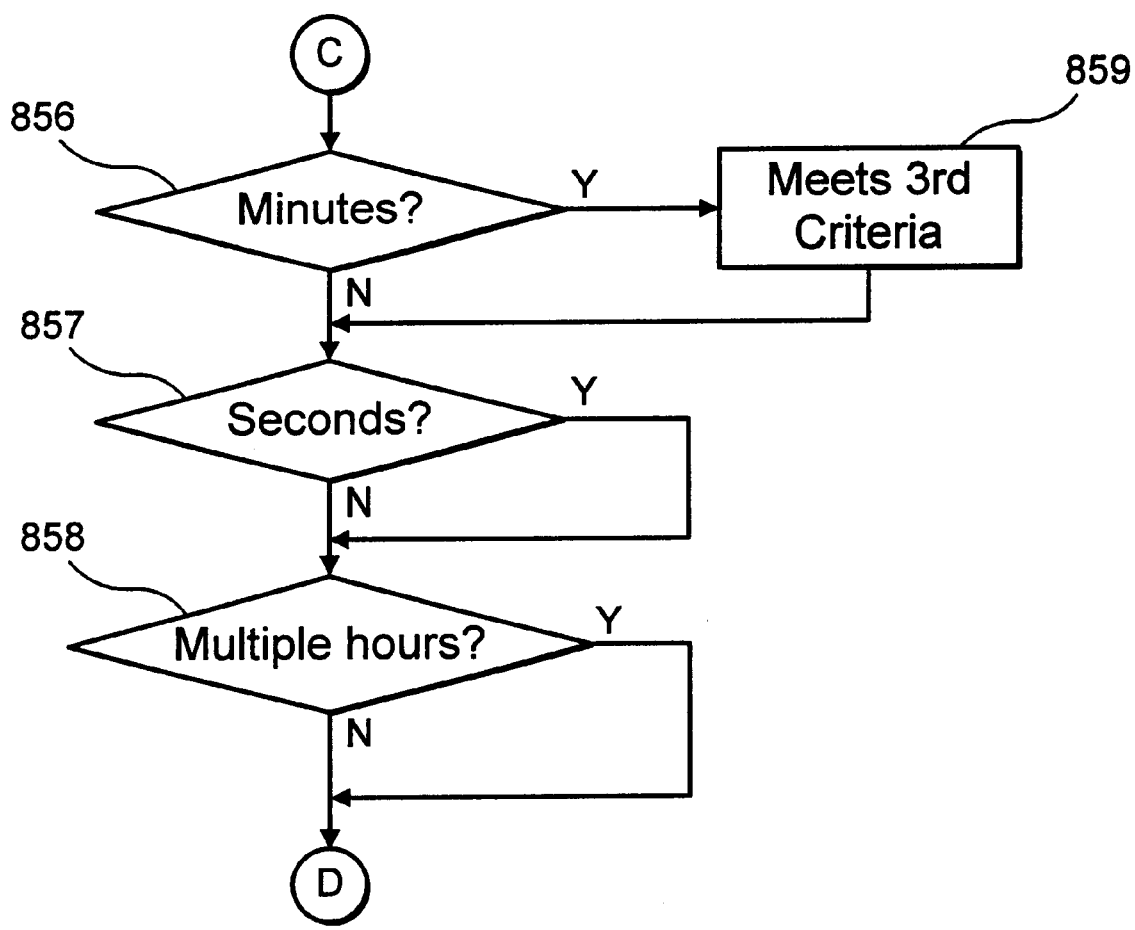
FIG. 8C illustrates a flow chart for determining the duration of a chest pain.

FIG. 8C illustrates a flow chart for determining the duration of a chest pain. The user is queried whether the chest pain lasts minutes, seconds, or multiple hours (steps 856–858). If the chest pain last minutes, then the third of the five criteria has been met (step 859).

Figure 8D:
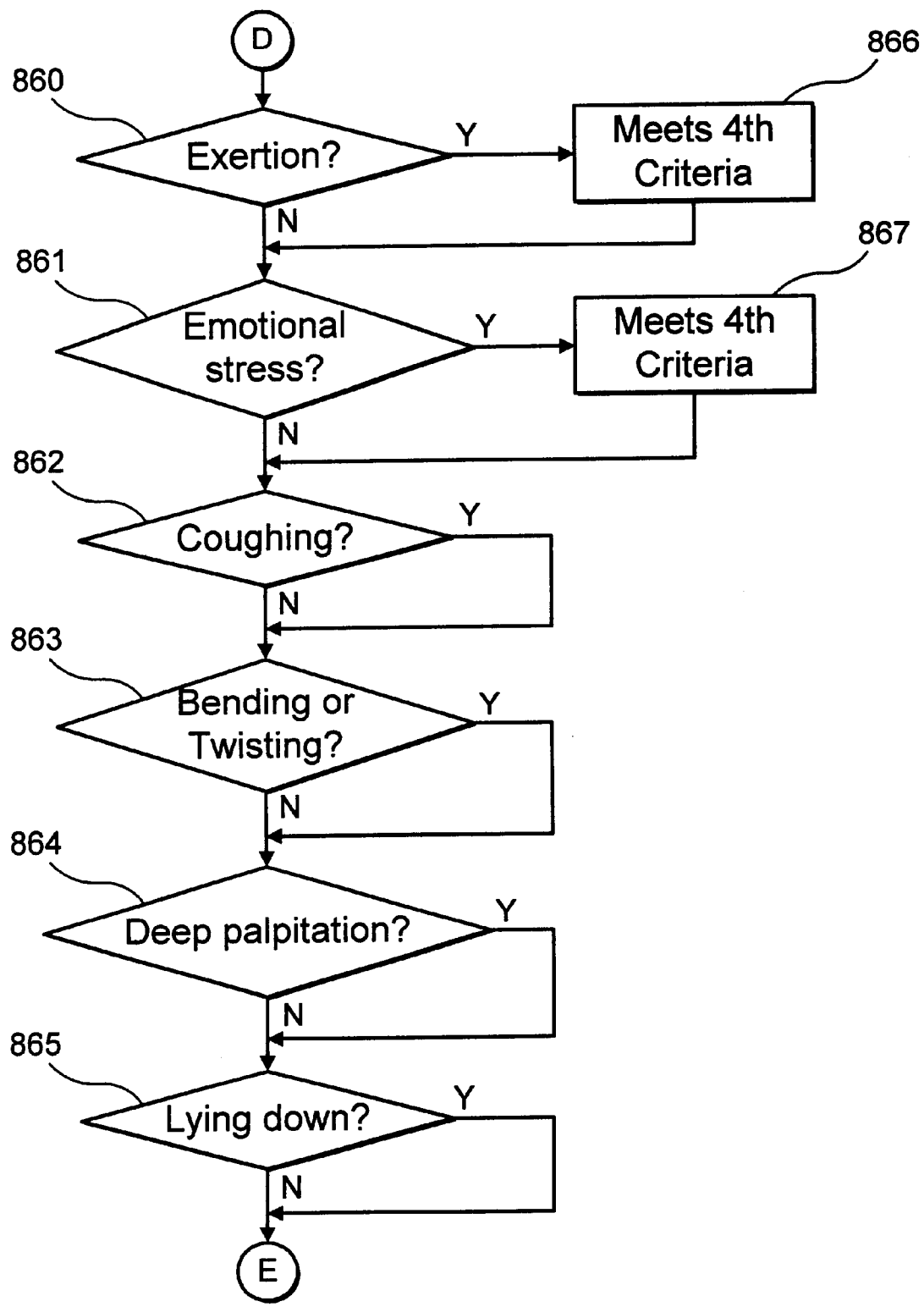
FIG. 8D illustrates a flow chart for determining what provokes a chest pain.

FIG. 8D illustrates a flow chart for determining what provokes a chest pain. The user is queried whether exertion, emotional stress, coughing, bending or twisting, deep palpation and/or lying down provokes the chest pain (steps 860–865). If the user responds that exertions and/or emotional stress provokes the chest pain, then the fourth of the five criteria has been met (steps 866–867).

Figure 8E:
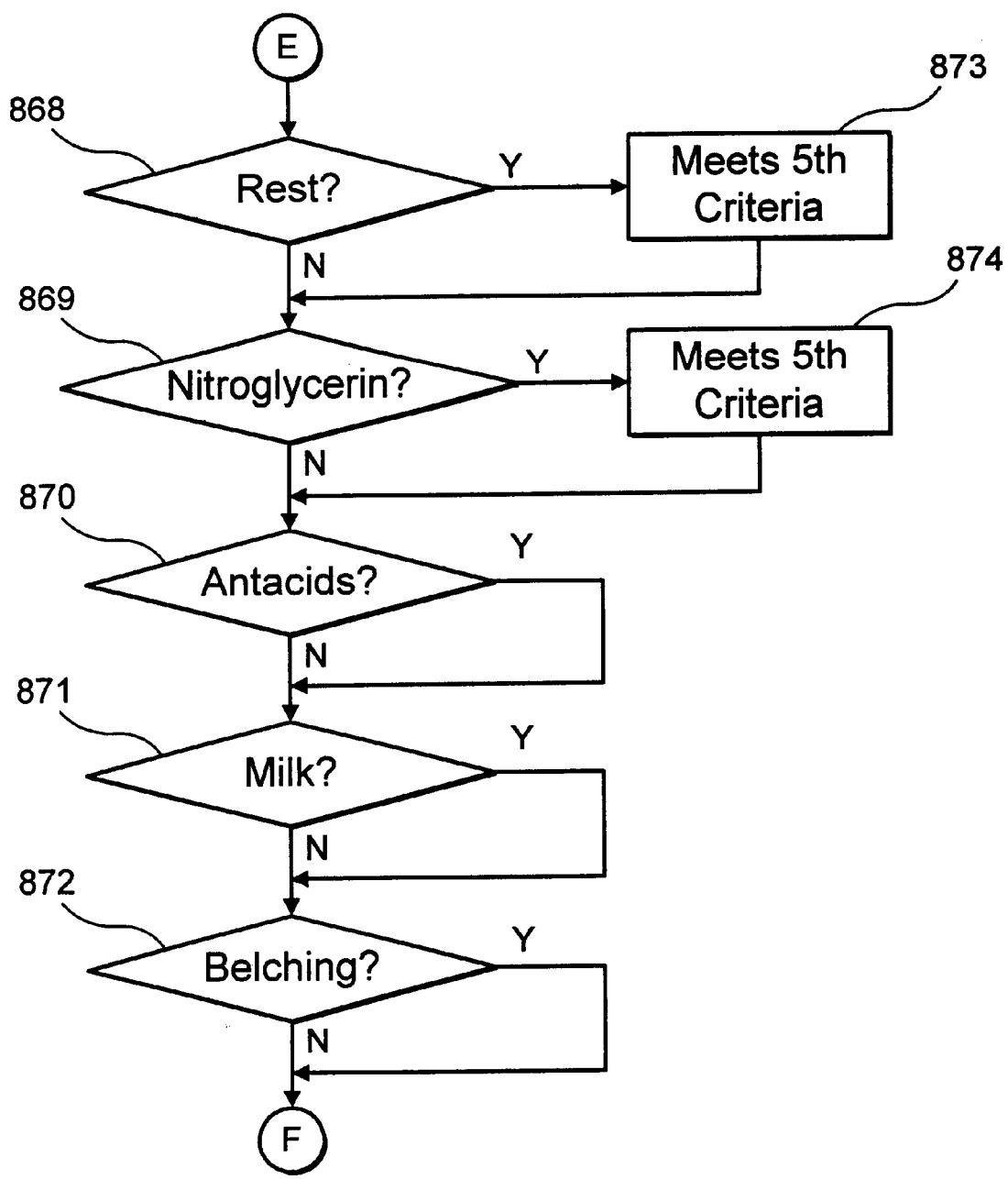
FIG. 8E illustrates a flow chart for determining what provides pain relief for a chest pain.

FIG. 8E illustrates a flow chart for determining what provides relief for a chest pain. The user is queried whether rest, nitroglycerine, antacids, and/or belching offer pain relief (steps 868–872). If rest and/or nitroglycerine offer pain relief for the chest pain, then the fifth of the five criteria has been met (steps 873–874).

Figure 8F:
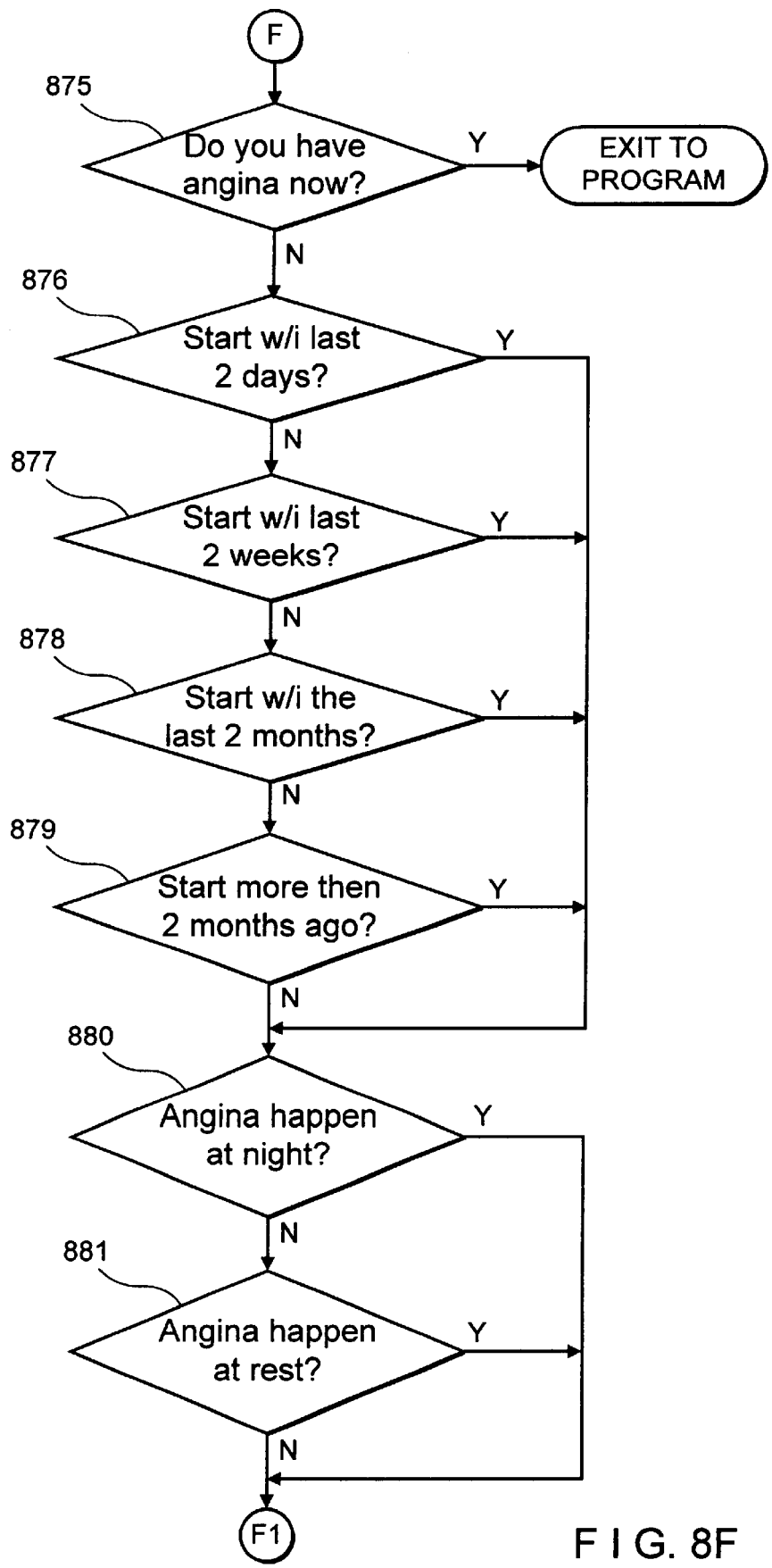
FIG. 8F illustrates a flow chart for determining the stability of angina.

FIG. 8F illustrates a flow chart for determining the stability of angina (chest pain). First, the user is queried whether the user has angina now (step 875) If the user has angina, the probability of diagnosis section is exited tot he main program. If the user does not have angina now, the user is queried about when the angina first started (steps 876–879. Next, the user is queried whether his or her angina happens at night or at rest, and while the user is moving around (steps 880–882). The user is queried whether his or her angina lasts at least 15–20 minutes (step 883). Next, the user is queried whether his or her angina is increasing, makes him breathless or lightheaded, and limits his or her lifestyle (steps 883–886). Based on the user's responses in steps 875–886, the user's angina is classified as stable or unstable, and the risk of the angina leading to a heart attack is determined using Clinical Practice Guideline, Number 10, "Unstable Angina: Diagnosis and Management" published by the U.S. Department of Health and Human Services Agency for Healthcare Policy and Research.

Figure 8G:
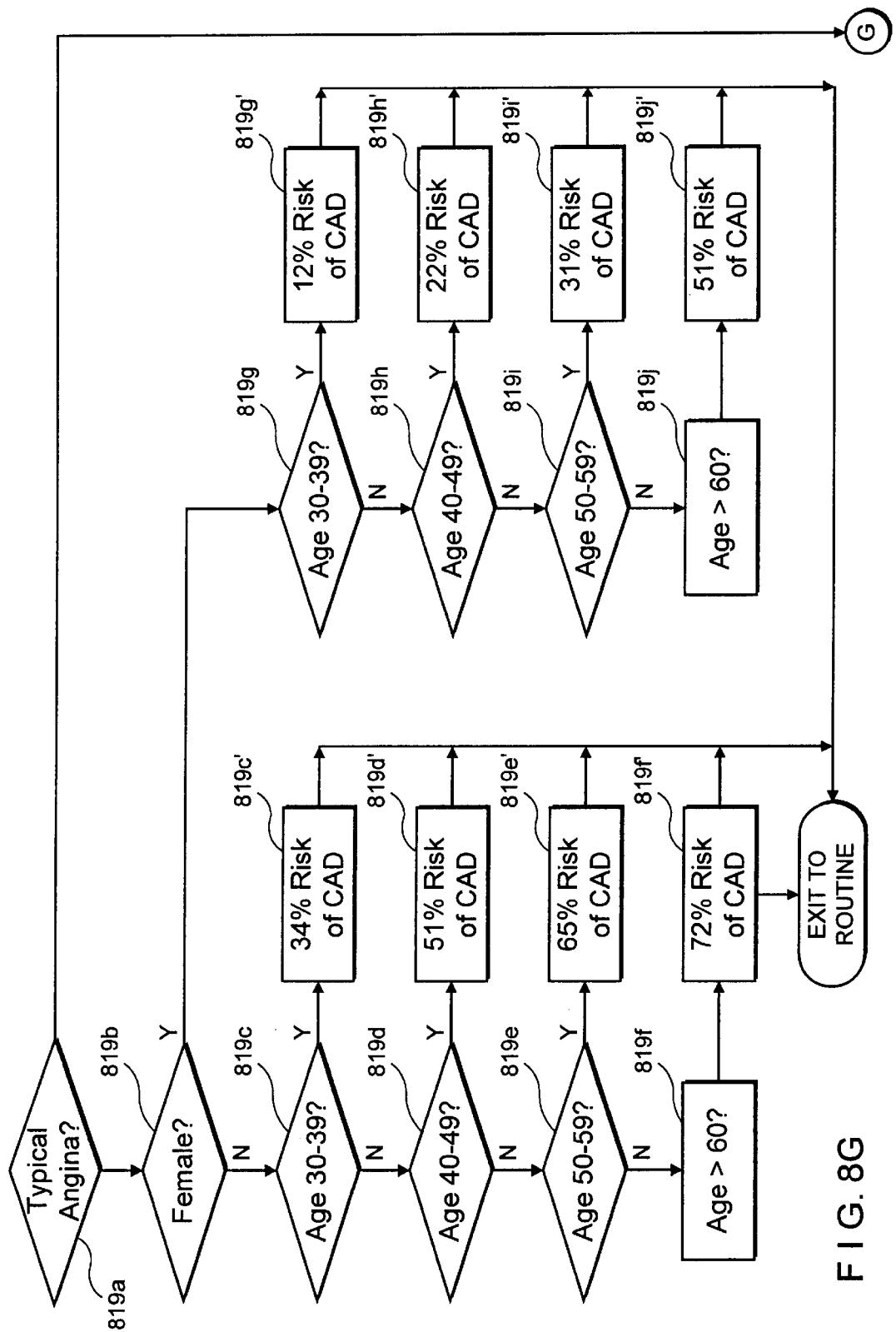
FIG. 8G illustrates a flow chart for determining the risk that the angina is CAD.

FIG. 8G illustrates a flow chart of the step of determining the risk that the angina is CAD. The risk is determined based on information described in Table 9 of the paper entitled "ACC/AHA/ACP-ASIM Guidelines for the Management of Patients with Chronic Stable Angina" published in the Journal of the American College of Cardiology. If the user is a male with atypical angina, then he has:

a 34% risk if he is 30–39 years old (steps 819c, 819c'),
a 51% risk if he is 40–49 years old (steps 819d, 819d'),
a 65% risk if he is 50–59 years old (steps 819e, 819e'), and
a 72% risk if he is over 60 years old (steps 819f, 819f').
If the user is a female with atypical angina, then she has:
a 12% risk if she is 30–39 years old (steps 819g, 819g'),
a 22% risk if she is 40–49 years old (steps 819h, 819h'),
a 31% risk if she is 50–59 years old (steps 819i, 819i'), and
a 51% risk if she is over 60 years old (steps 819j, 819j').
If the user is a male with typical angina, then he has:
a 78% risk if he is 30–39 years old (steps 819l, 819l'),
a 87% risk if he is 40–49 years old (steps 819m, 819m'),
a 93% risk if he is 50–59 years old (steps 819n, 819n'), and
a 94% risk if he is over 60 years old (steps 819o, 819o').
If the user is a female with typical angina, then she has:
a 26% risk if she is 30–39 years old (steps 819p, 819p'),
a 55% risk if she is 40–49 years old (steps 819q, 819q'),
a 73% risk if she is 50–59 years old (steps 819r, 819r'), and
a 86% risk if she is over 60 years old (steps 819s, 819s').

Figure 8H:
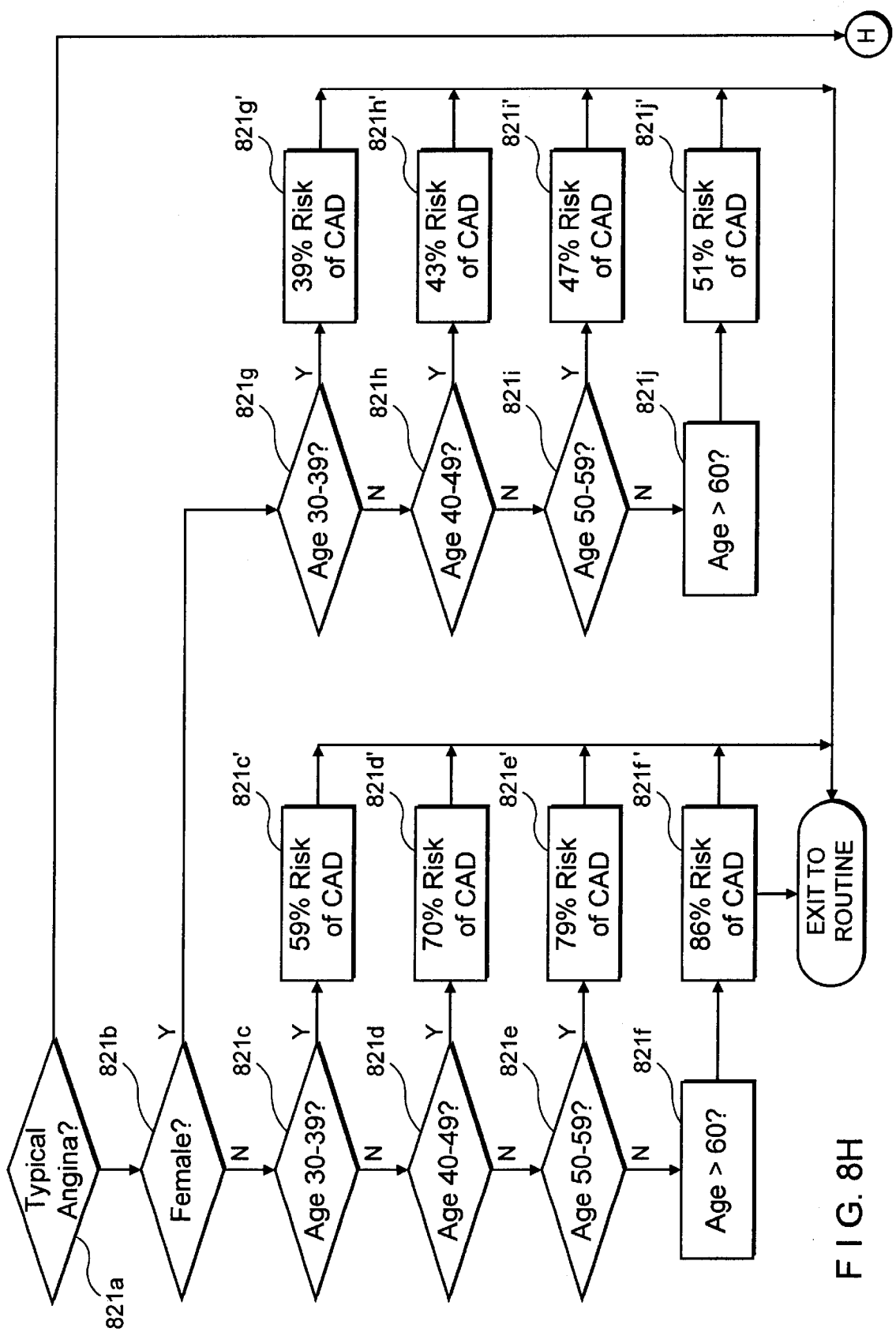
FIG. 8H illustrates a flow chart for determining the risk that angina is CAD for an individual that smokes and has diabetes and hyperlipidemia.

FIG. 8H illustrates a flow chart for determining the risk that angina is CAD for a user that smokes and has diabetes and hyperlipidemia. The risk is determined based on information described in Table 10 of the paper entitled "ACC/AHA/ACP-ASIM Guidelines for the Management of Patients with Chronic Stable Angina" published in the Journal of the American College of Cardiology. If the user is a male with atypical angina, then he has:

a 59% risk if he is 30–39 years old (steps 821c, 821c'),
a 70% risk if he is 40–49 years old (steps 821d, 821d'),
a 79% risk if he is 50–59 years old (steps 821e, 821e'), and
a 86% risk if he is over 60 years old (steps 821f, 821f').
If the user is a female with atypical angina, then she has:
a 39% risk if she is 30–39 years old (steps 821g, 821g'),
a 43% risk if she is 40–49 years old (steps 821h, 821h'),
a 47% risk if she is 50–59 years old (steps 821i, 821i'), and
a 51% risk if she is over 60 years old (steps 821j, 821j').
If the user is a male with typical angina, then he has:
a 88% risk if he is 30–39 years old (steps 821l, 821l'),
a 92% risk if he is 40–49 years old (steps 821m, 821m'),
a 95% risk if he is 50–59 years old (steps 821n, 821n'), and
a 97% risk if he is over 60 years old (steps 821o, 821o').
If the user is a female with typical angina, then she has:
a 78% risk if she is 30–39 years old (steps 821p, 821p'),
a 79% risk if she is 40–49 years old (steps 821q, 821q'),
a 82% risk if she is 50–59 years old (steps 821r, 821r'), and a 84% risk if she is over 60 years old (steps 821s, 821s'),

Doctor's Section

Figure 9:
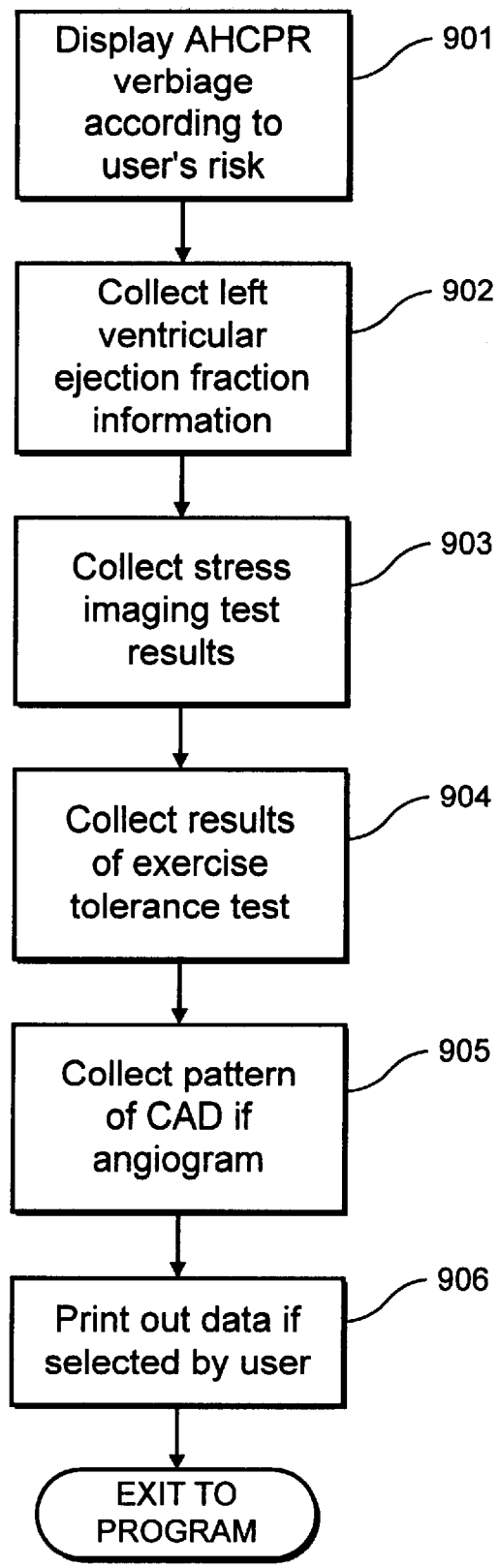
FIG. 9 illustrates a flow chart for the doctor section shown in FIG. 2.

FIG. 9 illustrates a flow chart of the doctor's section (process 900) shown in FIG. 2. This section is implemented if the user has an intermediate or high risk that his or her chest pain is CAD or the user's doctor wants a stress test. This section requires a physician's assistance for the user to complete. The user is queried regarding invasive and non-invasive testing. Invasive testing may include, for example, an angiogram. Noninvasive testing may include, for example, a stress test. In the first step, information regarding the user's risk of developing CAD is displayed (step 901). This information includes, for example, AHCPR information about the user's risk. Next, the user is prompted to enter information regarding left ventricular ejection fraction, stress imaging test results, exercise tolerance test results, and/or pattern of CAD if an angiogram was performed (steps 902–905).

Course of Action Section

Figure 10:
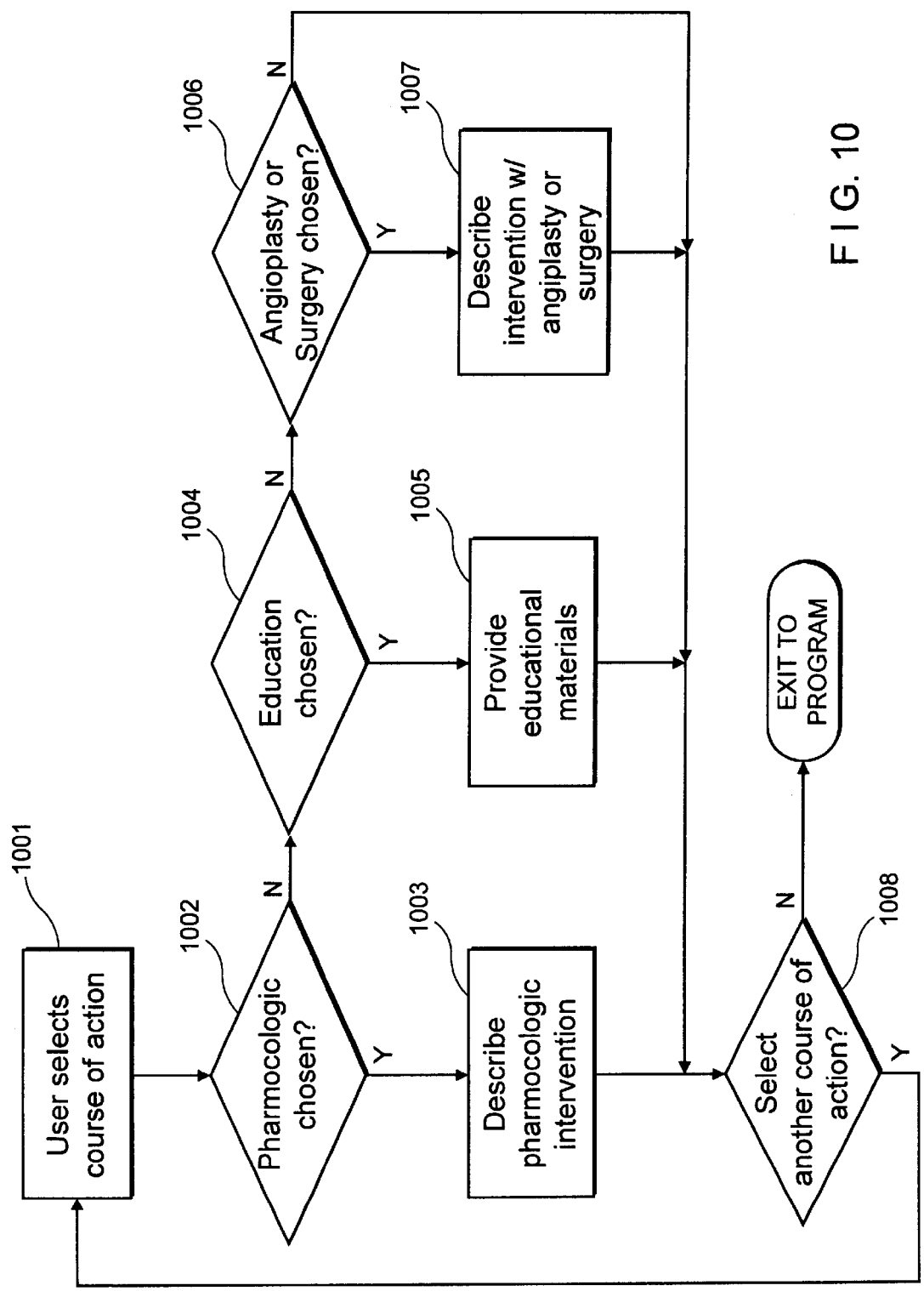
FIG. 10 illustrates a flow chart for the course of action section shown in FIG. 2.

FIG. 10 illustrates a flow chart for the course of action section shown in FIG. 2. In this section, the different courses of action, for example, pharmacological therapy, educational information, and angioplasty or surgery, are described for an individual that has CAD. The user is prompted to select a course of action (step 1001). Based on the course of action selected and the information provided by the user in doctor's section 900, a detailed description of that course of action is displayed to the user (steps 1003–1007). The detailed information includes information from, for example, the treatment section of "ACC/AHA/ACP-ASIM Guidelines for the Management of Patients with Chronic Stable Angina," and "ACC/AHA Guidelines for Coronary Artery Bypass Graft Surgery." After the user has finished viewing the requested course of action, the user may select another course of action to view (step 1008).

Risk Factor Modification Section

Figure 11A:
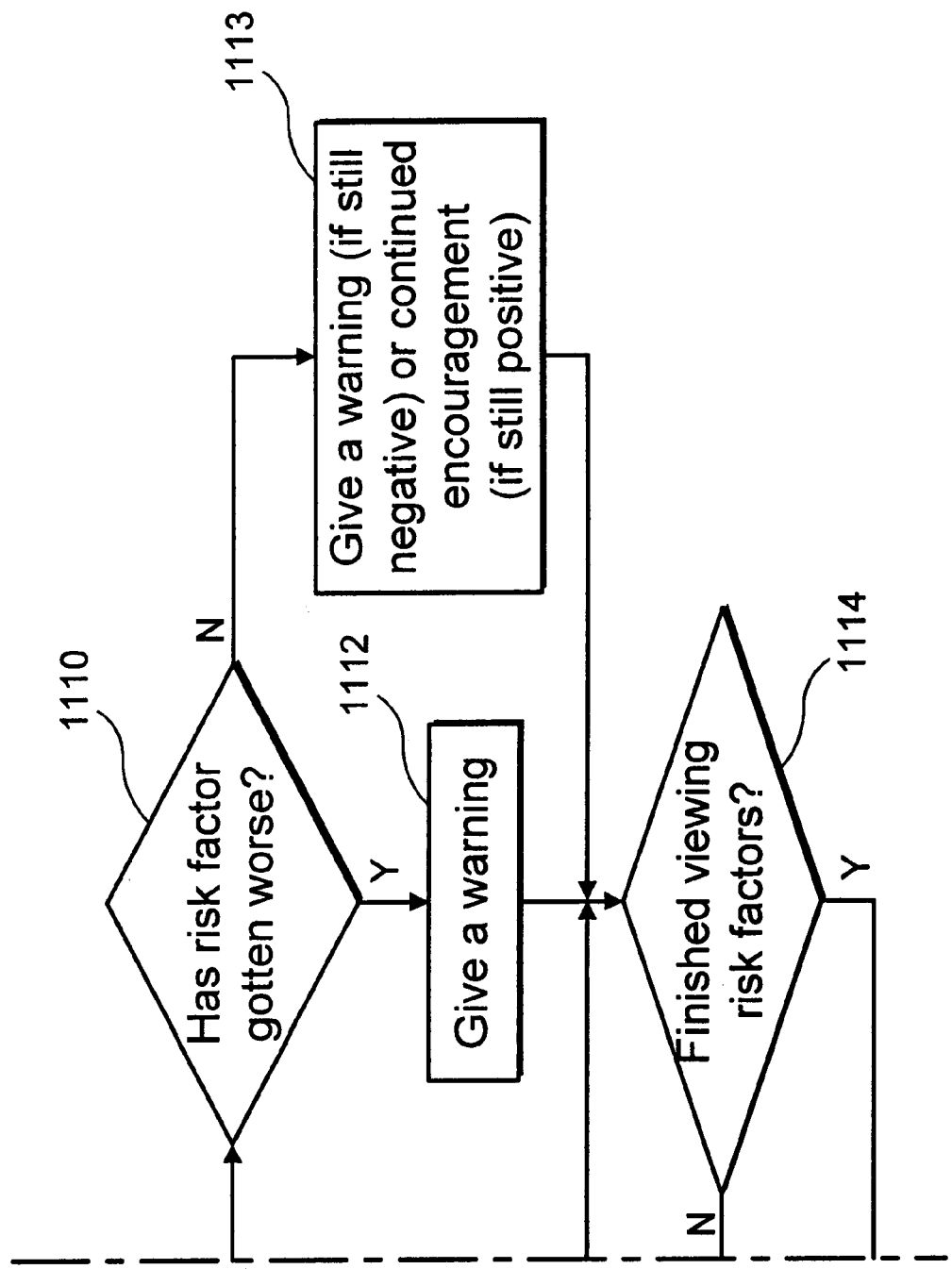
FIG. 11 illustrates a flow chart for the risk factor modification (RFM) section shown in FIG. 2.

FIG. 11 illustrates a flow chart for the risk factor modification (RFM) section shown in FIG. 2. In this section, the user is advised how to modify his or her risk of developing CAD. In step 1101, RFM is described and the user is prompted to proceed to a table of personal risk factors (FIG. 6A). If the user is a first time user (step 1102), a list of personal risk factors is displayed and the user is prompted to select a risk factor for a detailed display (step 1103). If the first-time user has selected a risk factor, a detailed description of the risk factor is displayed (step 1105). If the user is not a first time user, then an interactive table of the user's personal risk factors for the current and previous sessions is displayed and the user is prompted to select a risk factor for detailed display (step 1107). If the follow-up user selects a risk factor (step 1108), then based on the current status of the risk factor as compared with the previous status of the risk factor (steps 1109, 1110), encouragement (steps 1111, 1113) or a negative warning is given (step 1112). For example if a risk factor is currently negative and was positive (step 1109), the user is encouraged to keep up the good work (step 1111). If the risk factor is currently positive and was negative (step 1110), the user is given a warning (step 1112). If the risk factor is currently negative and was negative, the user is given a warning (step 1113). If the risk factor is currently positive and was positive, the user is given continued encouragement (step 1113). After viewing a risk factor, the user can view more risk factors or continue with the remainder program (steps 1106, 1114).

911 Section

FIG. 12 illustrates a flow chart for the 911 section shown in FIG. 2. If the user has acute chest pain (angina now) or high risk unstable angina (step 1201), then the user is advised to call 911 (step 1202) and provided with emergency information (step 1203). The emergency information may include, for example, the nearest hospital with a cardiac care center, a list of cardiologists, and instructions to take aspirin. If the user has intermediate risk unstable angina (step 1204), then the user is advised to contact a physician (step 1205) and provided with the emergency information (step 1203). The program is exited after step 1203.

In sum, the present invention provides an effective method and system for determining an individual's risk of developing a disease. The present invention determines the risk using a user's responses to detailed question, and if the individual already has the disease, the risks associated with the disease are provided to the user. Based on the responses and established practice guidelines, the user is provided with contemporaneous feedback whether a response indicates a positive risk factor for the disease. The user is also provided with detailed information on the individual's progress on subsequent implementations of the present invention.

What is claimed is:

1. An interactive computerized method for determining the risk of an individual developing a disease and the consequences of developing the disease, comprising the steps of:

transmitting questions to a user pertaining to risk factors for the disease via a processor;

receiving responses to the questions from the user via the processor;

transmitting substantially contemporaneous feedback to the responses via the processor;

if the individual does not have the disease, determining the risk of the individual developing the disease using at least one of the responses and practice guidelines for the disease;

if the individual does have the disease, determining associated consequences of the disease using at least one of the responses and the practice guidelines for the disease;

transmitting a summary of positive risk factors and risk modification information to the user via the processor;

tracking changes in the responses and the positive risk factors for the individual over time.

2. The method according to claim 1, wherein:

the disease includes coronary artery disease.

3. The method according to claim 1, wherein:

the questions include questions about at least one of physical characteristics, lifestyle, and medical history.

4. The method according to claim 3, wherein:

at least one of:

the physical characteristics include age, gender, race, height and weight;

the lifestyle questions include questions about at least one of smoking habits, drinking habits, vitamin intake, and stress; and the medical history Questions include questions about at least one of blood pressure, diabetes, menopause, ovary removal, hormone replacement, CAD, heart attack, coronary artery bypass surgery, angioplasty, peripheral vascular disease, left ventricular hypertophy, family history, lipid profile, stress tests, and angiograms.

5. The method according to claim 1, further comprising the step of:

determining the risk factors for the disease using the practice guidelines.

6. The method according to claim 1, wherein:

the processor operates in one of a LAN environment, WAN environment, the WWW and the Internet.

7. The method according to claim 1, wherein:

the step of receiving the responses includes storing the responses in memory.

8. The method according to claim 7, wherein:

the memory includes at least one database.

9. The method according to claim 1, wherein:

the contemporaneous feedback includes at least one of general information about at least one risk factor, and whether the risk factor is positive for the individual.

10. The method according to claim 1, wherein:

the practice guidelines include practice guidelines published by at least one of the American College of Cardiology and American Heart Association, U.S. Department of Health and Human Services Agency for Healthcare Policy and Research, and the National Heart Lung and Blood Institute.

11. The method according to claim 1, wherein:

the associated consequences include at least one of invasive intervention and noninvasive intervention.

12. The method according to claim 11, wherein:

at least one of:
the invasive intervention includes at least one of surgery and angioplasty; and
the noninvasive intervention includes at least one of pharmacological therapy and education.

13. The method according to claim 1, wherein:

the positive risk factors include being a male, being one of a postmenopausal female and a postmenopausal female with ovaries removed, being a male over 40 years of age, being a female over 45 years of age, having a BMI that indicates the user is overweight or obese, being a smoker, having diabetes mellitus, having elevated lipid levels, having known CAD, having known peripheral vascular disease, not exercising, having hypertension, having feelings of stress and anxiety, having left ventricular hypertrophy, not taking antioxidant vitamins, having high homocysteine levels, not getting the RDA of folate, vitamin B6 or vitamin B12, having a high lipoprotein level, having a low alcohol intake, having a positive family history of coronary disease, and not taking one aspirin per day.

14. The method according to claim 1, wherein:

the risk factor modification information includes information about how to change the positive risk factors to negative risk factors.

15. The method according to claim 1, wherein:

the step of tracking includes advising the user when there has been one of a change and no change in a risk factor.

* * * * *